(12) United States Patent
Suzuki et al.

(10) Patent No.: US 7,271,952 B2
(45) Date of Patent: Sep. 18, 2007

(54) MICROSCOPE IMAGING APPARATUS AND BIOLOGICAL-SPECIMEN EXAMINATION SYSTEM

(75) Inventors: Yoshimasa Suzuki, Kawasaki (JP); Kayuri Muraki, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/655,512

(22) Filed: Jan. 18, 2007

(65) Prior Publication Data
US 2007/0121199 A1    May 31, 2007

(51) Int. Cl.
G02B 21/00    (2006.01)
(52) U.S. Cl. ................. 359/368; 250/458.1; 250/459.1
(58) Field of Classification Search ..................... None
See application file for complete search history.

(56) References Cited

U.S. PATENT DOCUMENTS

| | | |
|---|---|---|
| 6,429,897 B2 | 8/2002 | Derndinger et al. |
| 6,496,309 B1 | 12/2002 | Bliton et al. |
| 6,640,014 B1 | 10/2003 | Price et al. |
| 6,819,416 B2 | 11/2004 | Maeda et al. |
| 2001/0012069 A1 | 8/2001 | Derndinger et al. |
| 2002/0167604 A1 | 11/2002 | Ban et al. |
| 2003/0222197 A1 | 12/2003 | Reese et al. |
| 2004/0101210 A1 | 5/2004 | Weinstein et al. |
| 2004/0106862 A1 | 6/2004 | Kohama |
| 2004/0263829 A1 | 12/2004 | Ikeda |
| 2005/0168730 A1 | 8/2005 | Sakai et al. |
| 2005/0270639 A1 | 12/2005 | Miki |
| 2006/0082782 A1 | 4/2006 | Ogawa et al. |

FOREIGN PATENT DOCUMENTS

| | | |
|---|---|---|
| JP | 08-292198 | 11/1996 |
| JP | 09-037005 | 2/1997 |
| JP | 09-236750 | 9/1997 |
| JP | 10-325711 | 12/1998 |
| JP | 10-326587 | 12/1998 |
| JP | 11-196225 | 7/1999 |
| JP | 11345585 A | * 12/1999 |
| JP | 2002-039960 | 2/2002 |
| JP | 2002-165138 | 6/2002 |
| JP | 2002-535717 | 10/2002 |
| JP | 2002-334326 | 11/2002 |
| JP | 2003-158669 | 5/2003 |
| JP | 2003-319249 | 11/2003 |
| WO | WO 03/014400 | 2/2003 |

* cited by examiner

*Primary Examiner*—Mark A. Robinson
*Assistant Examiner*—Lee Fineman
(74) *Attorney, Agent, or Firm*—Kenyon & Kenyon LLP

(57) ABSTRACT

A microscope imaging apparatus and a biological-specimen examination system that can accurately carry out measurement even for an object under examination having substantial brightness non-uniformity are provided. The microscope imaging apparatus includes a stage that holds the object under examination, an illumination unit that illuminates the object under examination, an image-acquisition unit that acquires images of the object under examination, and a motion unit that moves the stage and the image-acquisition unit relative to each other. The image-acquisition unit includes an imaging device capable of image acquisition using a time delay integration method. When acquiring a plurality of images of the object under examination, the exposure time during which accumulated charge is produced in the imaging device is made different for each of the acquired images, and the plurality of images are combined into a single image.

4 Claims, 43 Drawing Sheets

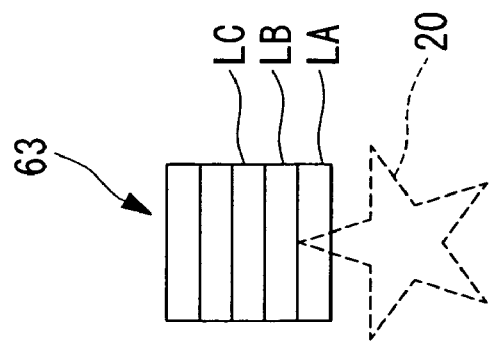
FIG. 2A                    FIG. 2B                    FIG. 2C

FIG. 32
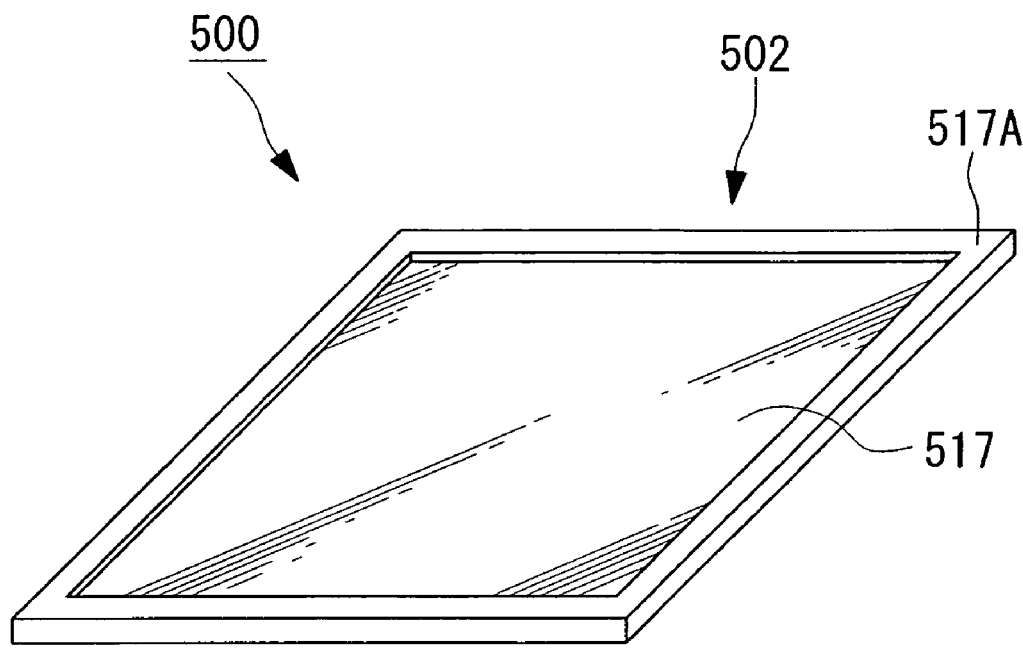
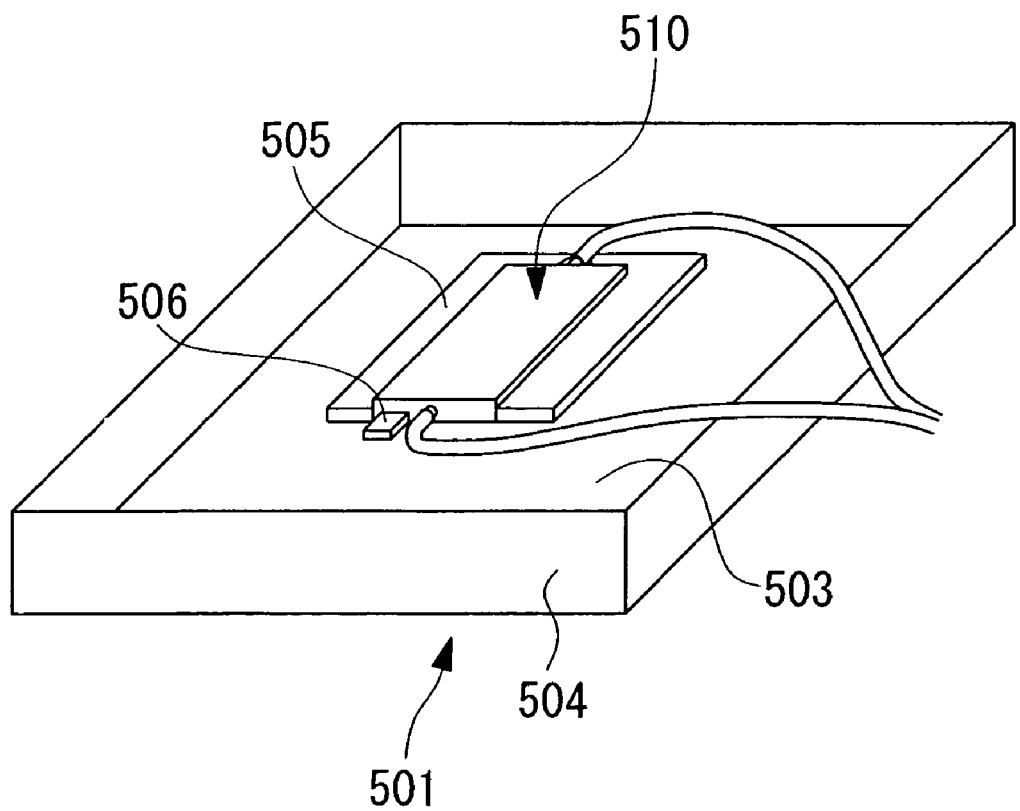

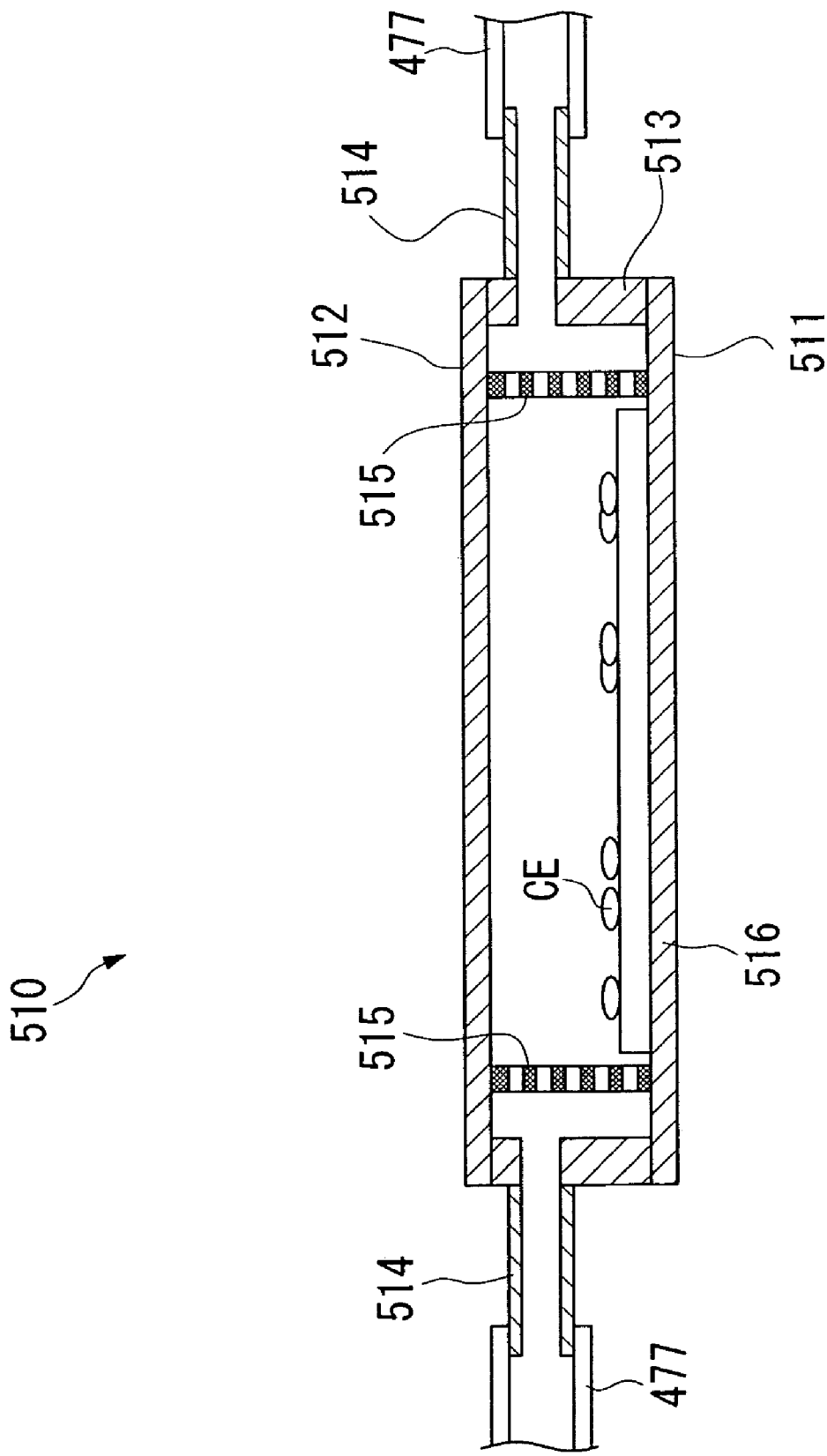

MICROSCOPE IMAGING APPARATUS AND BIOLOGICAL-SPECIMEN EXAMINATION SYSTEM

BACKGROUND OF THE INVENTION

1. Field of the Invention

The present invention relates to a microscope imaging apparatus and to a biological-specimen examination system using the same.

2. Description of the Related Art

A known apparatus for measuring fluorescence and so on of a biological specimen uses a microplate. Since the fluorescence intensity of a biological specimen is extremely dark, it is necessary to capture the fluorescence using a long exposure time. Also, since the microplate has a shape that is larger than the field of view of a microscope, it takes some time to examine the entire microplate.

One method of imaging such fluorescence is a method in which measurement is carried out with a CCD (charge coupled device) while the microplate is repeatedly moved and stopped. A plurality of wells are provided in the microplate, and the specimens are held in these wells. Therefore, by repeatedly moving and stopping the microplate, the fluorescence from the specimen in each well can be measured. The microplate is moved by means of a moving stage.

Another known method of imaging the fluorescence is a method using TDI (time delay integration) imaging devices (for example, see patent document 1). The imaging devices using the TDI method are constituted by a plurality of optoelectronic devices. Fluorescence from the specimen is incident on the optoelectronic devices, and a charge corresponding to the incident fluorescence is produced in the optoelectronic devices by optical-to-electrical conversion. This charge is then transferred between optoelectronic devices as the microplate moves. Since the motion of the microplate is associated with the motion of the charge, fluorescence from the same position on the specimen is incident again on the optoelectronic devices after they have been moved. As a result, the charge builds up. Thus, the charge is progressively accumulated when using the TDI method.

The feature of the TDI method is that charge corresponding to the fluorescence is accumulated while being transferred. Therefore, compared to the case where a one-dimensional line sensor is used for image acquisition, the speed at which the stage is moved can be increased according to the number of charge transfer lines. As a result, the measurement time can be shortened.

BRIEF SUMMARY OF THE INVENTION

A microscope imaging apparatus according to the present invention comprises:
a stage that holds an object under examination;
an illumination unit that illuminates the object under examination;
an image-acquisition unit that acquires images of the object under examination;
a motion unit that moves the stage and the image-acquisition unit relative to each other; and
a control unit that controls the image-acquisition unit and the motion unit,
wherein the image-acquisition unit includes an imaging device that is capable of acquiring images with the time delay integration method, and
when image acquisition of the object under examination is carried-out a plurality of times, the control unit makes the exposure times of the imaging device different for each image acquisition.

Another microscope imaging apparatus according to the present invention comprises:
a stage that holds an object under examination;
an illumination unit that illuminates the object under examination;
an image-acquisition unit that acquires images of the object under examination;
a motion unit that moves the stage and the image-acquisition unit relative to each other; and
a control unit that controls the image-acquisition unit and the motion unit,
wherein the image-acquisition unit includes an imaging device that is capable of acquiring images with a time delay integration method, and
by performing a prescan of the object under examination to obtain a detected intensity of the object under examination, the control unit determines an exposure time for image acquisition after the prescan on the basis of the detected intensity.

Another microscope imaging apparatus according to the present invention comprises:
a stage that holds an object under examination;
an illumination unit that illuminates the object under examination;
an image-acquisition unit that acquires images of the object under examination;
a motion unit that moves the stage and the image-acquisition unit relative to each other; and
a control unit that controls the image-acquisition unit and the motion unit,
wherein the image-acquisition unit includes an imaging device that is capable of image acquisition using two methods;
the control unit includes:
an examination-object-parameter input unit for inputting information about the object under examination as an examination-object parameter;
a calculation unit that calculates a time for the relative motion on the basis of the examination-object parameter which has been input; and
a switching unit that switches the image-acquisition method of the imaging device on the basis of the calculation result; and
the two image-acquisition methods are a time delay integration method and a two-dimensional imaging method in which accumulated charge is produced by a single exposure.

A biological-specimen examination system according to the present invention comprises:
a culture unit for culturing a biological specimen; and
a detection unit disposed adjacent to the culture unit, wherein the detection unit includes:
an above-described microscope imaging apparatus; and
a preserving unit for preserving the biological specimen in a predetermined state.

BRIEF DESCRIPTION OF THE SEVERAL VIEWS OF THE DRAWINGS

FIGS. 2A to 2C depict the transfer of signal charge in the TDI method.

FIG. 32 is a perspective view of an incubator box used in the biological-specimen examination system shown in FIG. 30.

FIG. 33 is a cross-sectional view of a chamber in the incubator box shown in FIG. 32.

DETAILED DESCRIPTION OF THE INVENTION

A microscope imaging apparatus will be described below with reference to FIGS. 1A to 6.

First, an image-acquisition operation according to a time delay integration (TDI) method will be described using FIGS. 1A to 1C.

Figure 1A:
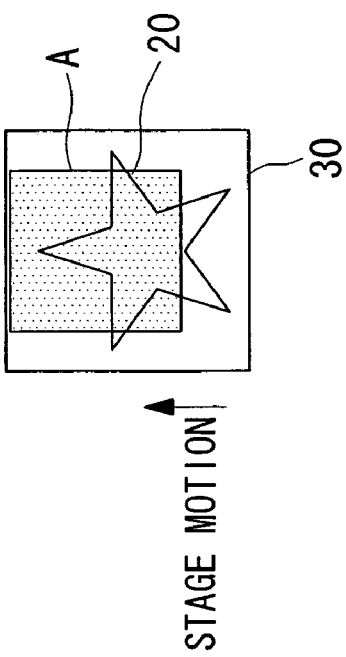
FIGS. 1A to 1C depict an image acquisition operation using the TDI method.
Figure 1B:
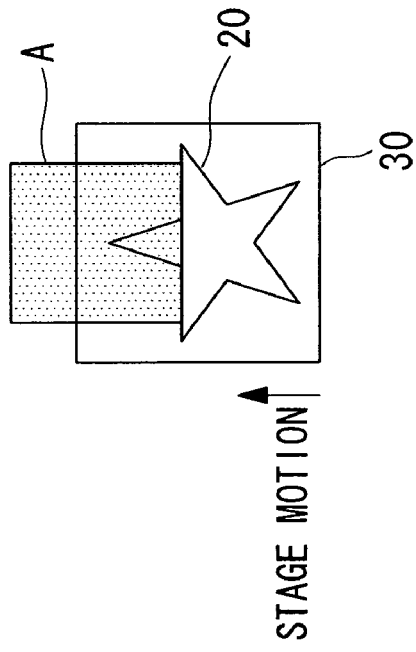
Figure 1C:
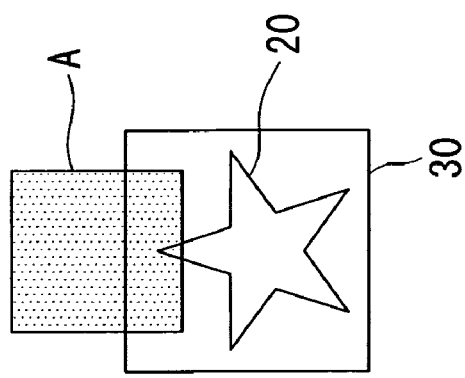
Figure 3A:
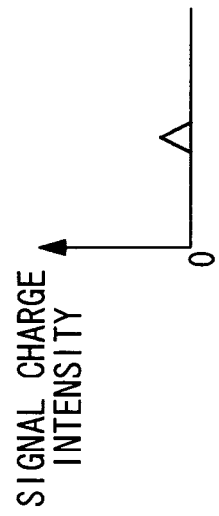
FIGS. 3A to 3C show the intensity of signal charge accumulated in horizontal lines.
Figure 3B:
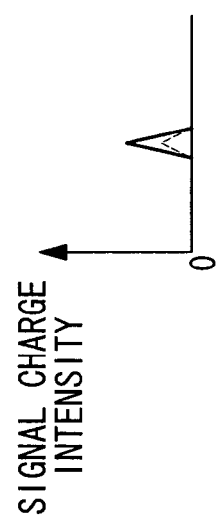
Figure 3C:
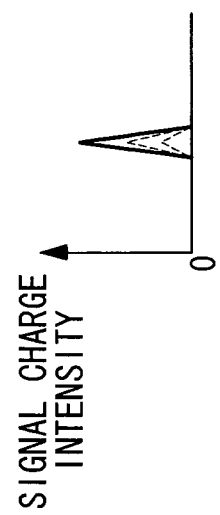

FIGS. 1A, 1B, and 1C depict the TDI image-capturing operation. FIGS. 2A, 2B, and 2C depict the transfer of signal charge in the TDI method. FIG. 3A shows the level of signal charge accumulated in a horizontal line LA, FIG. 3B shows the level of signal charge accumulated in a horizontal line LB, and FIG. 3C shows the level of signal charge accumulated in a horizontal line LC.

For the sake of simplifying the explanation, a star-shaped specimen is assumed here. However, the shape of the specimen is not particularly limited to this shape.

The positional relationship between a specimen (subject under examination) 20 and an imaging area S of an imaging device 63 is shown in FIG. 1A. Image-acquisition begins when the top of the specimen 20 and the bottom of the imaging area S overlap each other. Thus, initially, only the tip of the upward-facing point of the star projects onto the imaging device 63. At this time, as shown in FIG. 2A, the image of the tip of the upward-facing point is acquired by the horizontal line LA of the imaging device 63. As shown in FIG. 3A, signal charge with a level corresponding to the light intensity (brightness) from the specimen 20 is accumulated in the horizontal line LA.

Subsequently, a stage 30 is moved with a predetermined timing. As shown in FIG. 1B, the stage 30 is moved in the positive Y direction by a distance corresponding to one horizontal line of the imaging device 63. By doing so, the entire upward-facing point of the specimen 20 is imaged.

At this point, as shown in FIG. 2B, the signal charge accumulated in the horizontal line LA is transferred to the horizontal line LB in synchronization with the motion of the stage 30. Thus, the image of the specimen 20 is acquired by the horizontal lines LA and LB of the imaging device 63.

Therefore, as shown in FIG. 3B, the signal charge accumulated during this image acquisition is added to the signal charge accumulated in the previous acquisition. In other words, the signal charges obtained due to the previous and current image acquisition are accumulated in the horizontal line LB. As a result, the signal charge level is twice as high as that measured in one line.

In this way, charge transfer is carried out from the state shown in FIG. 2A to the state shown in FIG. 2B. The time interval at which this charge transfer is carried out is called the TDI line transfer rate.

The stage 30 is then moved further at the predetermined timing. That is, as shown in FIG. 1C, the stage 30 is again moved in the positive Y direction by an amount corresponding to one horizontal line of the imaging device 63. By doing so, image-acquisition of the specimen 20 proceeds.

At this point, as shown in FIG. 2C, the signal charge accumulated in the horizontal line LB is transferred to the horizontal line LC in synchronization with the motion of the stage 30. In addition, the signal charge accumulated in the horizontal line LA is transferred to the horizontal line LB. Thus, the image of the specimen 20 is acquired by the horizontal lines LA, LB, and LC.

Therefore, as shown in FIG. 3C, the signal charge obtained during this image-acquisition is added to the horizontal line LC. Thus, the signal charges obtained by the previous-but-one image-acquisition, the previous image-acquisition, and the current image-acquisition are accumulated in the horizontal line LC. In other words, the level of signal charge is three times higher than that measured with a single line. The signal charge obtained in the previous image-acquisition and the current image-acquisition are accumulated in the horizontal line LB.

By continuing with the above-described operation, the same number of image-acquisition operations as the number of horizontal scanning lines is performed. Accordingly, a signal charge for the same part of the specimen 20 is accumulated corresponding to the number of image-acquisition operations. Thus, with the TDI method, the image of the specimen 20 projected onto the imaging surface is shifted along with the motion of the stage 30, and the signal charge accumulated in the imaging device 63 is shifted in synchronization therewith.

Next, the exposure time used when carrying out image-acquisition in the TDI method will be discussed.

The exposure time in the TDI method is the time it takes for the signal light returning from the specimen 20 to be accumulated as the signal charge. In other words, the exposure time in the TDI method can be expressed as the product of the TDI line transfer rate and the cumulative number of pixels. Therefore, to change the exposure time, the TDI line transfer rate can be made faster to lengthen the exposure time or the TDI line transfer rate can be slowed down to shorten the exposure time.

For example, when using a CCD camera having 1,000 pixels in the Y direction as the imaging device 63, to acquire images with an exposure time of 0.2 s, the line transfer rate is set to 5 kHz (0.2 ms transfer time) according to the calculation shown below:

$$0.2s/1000=0/2ms.$$

Next, the stage scanning speed used in the TDI method will be discussed.

The stage 30 is moved in synchronization with the transfer of the signal charge. Therefore, the speed at which the stage 30 is moved can be expressed as the pixel size on the stage 30 divided by the TDI line transfer rate. The pixel size on the stage 30 can be obtained from the pixel size of the imaging device 63 (for example, a CCD) and the projection magnification.

For example, with a projection magnification of 10, a pixel size in the imaging device 63 of 6.45 µm, and a TDI line transfer rate of 5 kHz, the speed of the stage is 3.23 mm/s, according to the calculation shown below:

$$6.45 \times 10^{-3} \text{ mm}/10 \times 5 \times 10^{3} \text{ Hz} = 3.23 \text{ mm/s}.$$

Next, the structure of a microscope imaging apparatus will be described.

Figure 4:
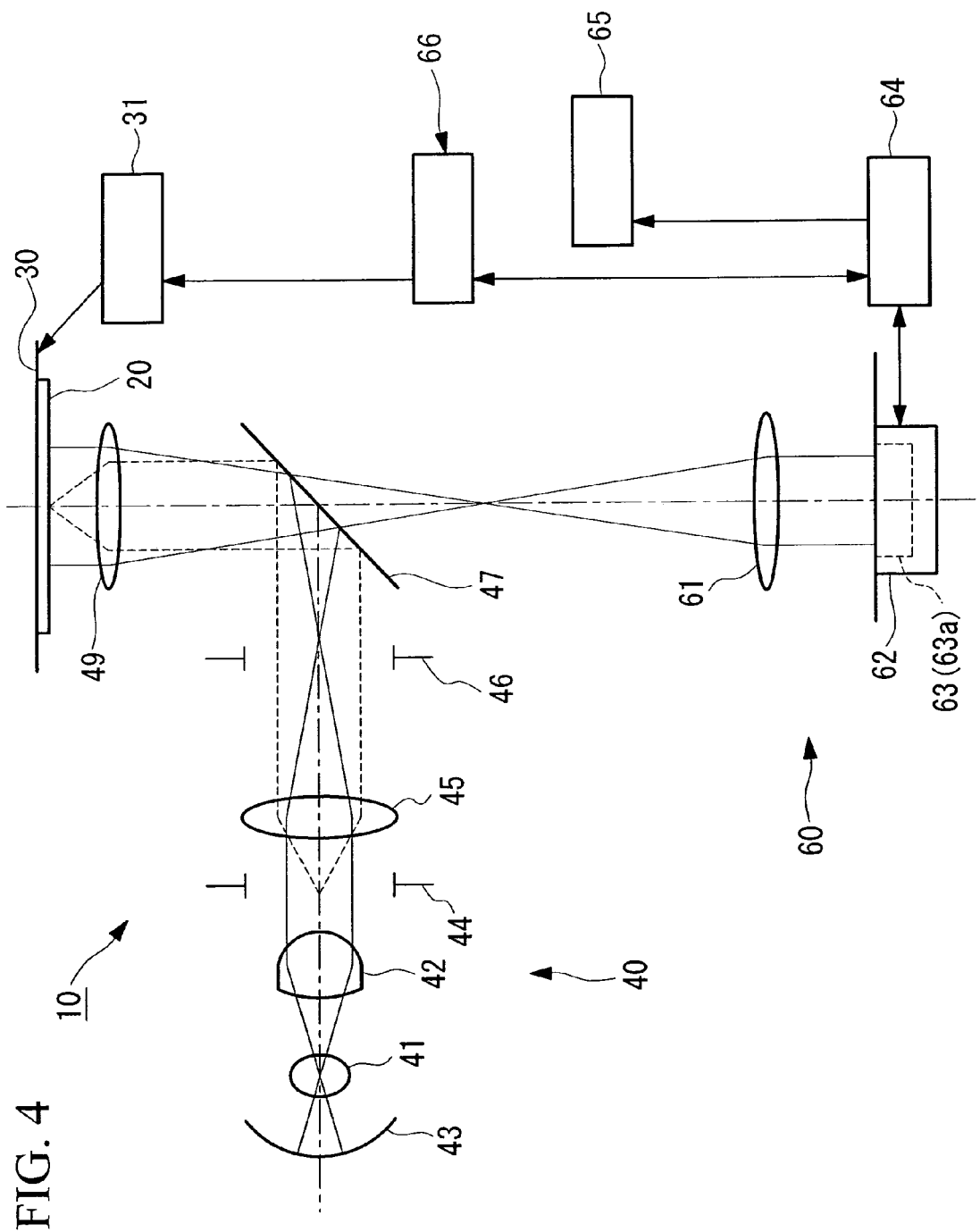
FIG. 4 shows the overall configuration of a microscope imaging apparatus.

FIG. 4 shows the overall configuration of a microscope imaging apparatus 10. The microscope imaging apparatus 10 shown in FIG. 4 is used in the first to third embodiments of the present invention described below.

As shown in FIG. 4, the microscope imaging apparatus 10 includes the stage 30, an illumination unit 40, and an image-acquisition unit 60. The stage 30 holds the specimen (object under examination) 20 thereon and is moveable. The illumination unit 40 radiates illumination light onto the specimen 20. The image-acquisition unit 60 acquires signal light emitted from the region irradiated with the illumination light and measures it.

The illumination unit 40 includes components capable of Kohler illumination. Specifically, these are a lamp 41, a collector lens 42, a reflecting mirror 43, a field stop 44, and a lens 45. A gas discharge lamp or the like, such as a halogen lamp, xenon lamp, or mercury lamp, is used at the light source lamp 41. The collector lens 42 collects light emitted from the lamp 41. The reflecting mirror 43 reflects light traveling backwards from the lamp 41 back towards the lamp 41 again. The field stop 44 is disposed after the collector lens 42. This field stop 44 is disposed at a conjugate position with respect to the focal point of an objective lens 49 described below. The diameter of the opening of this field stop 44 is adjustable. A lens 45 is disposed after the field stop 44. The lens 45 images the field stop 44 at infinity.

An aperture stop 46 is disposed after the lens 45, at the focal plane thereof. The diameter of the opening of this aperture stop 45 can be varied. By doing so, the size of the beam diameter at the exit-pupil position of the objective lens 49 can be adjusted. A mirror 47 is disposed after the aperture stop 46. A dichroic mirror that reflects light from the lamp 41 and that transmits return light (fluorescence) from the specimen 20 is used as the mirror 47. A half-mirror may be used instead of a dichroic mirror.

The objective lens 49 is disposed after the mirror 47. The stage 30 is disposed at a position facing the objective lens 49.

A stage driving mechanism (motion unit) 31 for driving the stage 30 is provided. The stage driving mechanism (motion unit) 31 drives the stage 30 in the X and Y directions on the basis of a signal output from a computer described below. Known technology, for example, a sliding motion mechanism, may be used as the stage driving mechanism 31. It is not particularly limited to a sliding motion mechanism, however.

An imaging lens 61 and a detector 62 are provided in the image-acquisition unit 60. Return light (fluorescence) from the specimen 20 is incident on the imaging lens 61, and the imaging lens 61 focuses (images) the incident light at a predetermined position. The detector 62 is disposed at a predetermined position and detects the return light from the specimen 20. The imaging device 63, which can acquire images by the TDI method, is provided in the detector 62. As described above, the imaging device 63 accumulates signal charge in each horizontal line in response to the movement of the stage 30.

The output of the detector 62 is connected to an image processing unit 64, which processes the output signal from the detector 62. A monitor 65 for displaying the processed signal is connected to the image processing unit 64. Also, the image processing unit 64 is connected to the computer 66. The stage driving mechanism 31 is also connected to the computer 66.

The computer (calculating unit) 66 calculates the exposure time in the main measurement. This calculation is carried out on the basis of information obtained during a prescan, as described above. This information is the brightness in each sample located portion (described below).

Figure 5B:
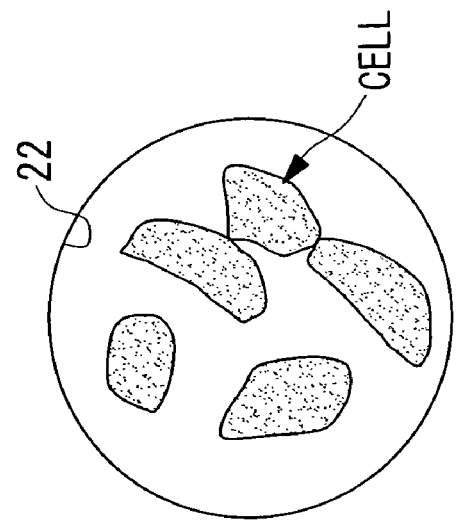
FIGS. 5A and 5B show the structure of a specimen.
Figure 5A:
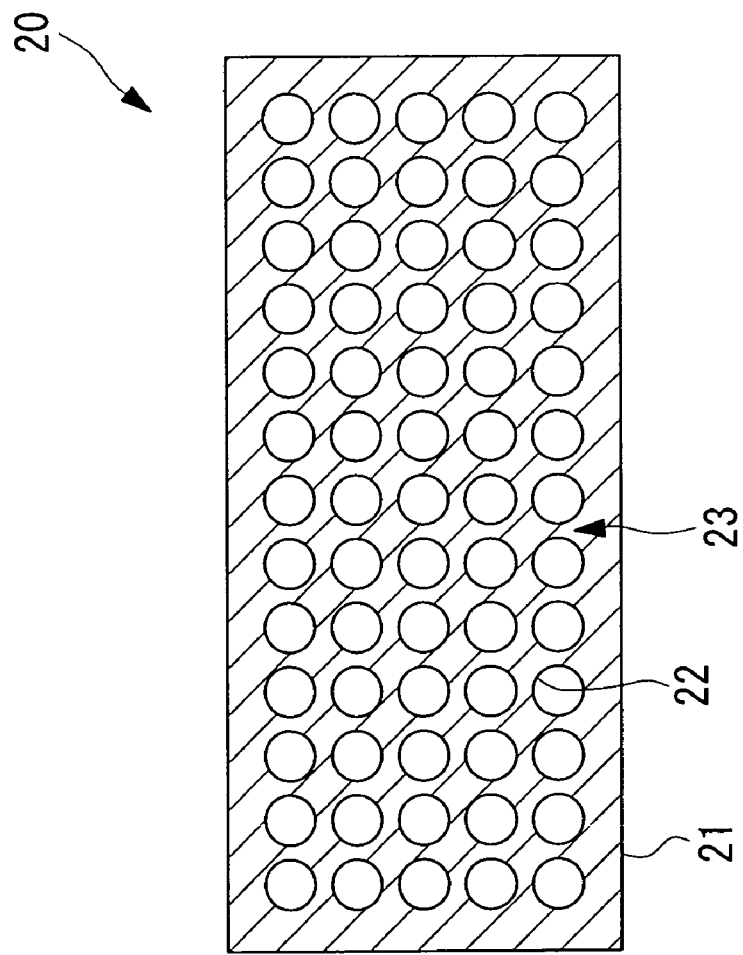

FIG. 5A depicts the shape of the specimen 20. FIG. 5B is a magnified view showing a sample located portion 22 of the specimen 20.

As shown in FIG. 5A, the specimen 20 includes a transparent substrate 21. This transparent substrate 21 is formed of, for example, a glass plate or a plastic plate. The sample located portions 22 are formed in a matrix on the transparent substrate 21. That is, a two-dimensional patterned portion 23 is formed by the plurality of sample located portions 22.

The sample located portions 22 have a substantially circular shape with a diameter of a few millimeters in plane view and have a concave profile in cross-section. As shown in FIG. 5B, cells, serving as the objects to be measured, are disposed in the sample located portions 22. The cells are cultured inside the sample located portions 22.

Next, stage scanning in the TDI method will be described.

Figure 6:
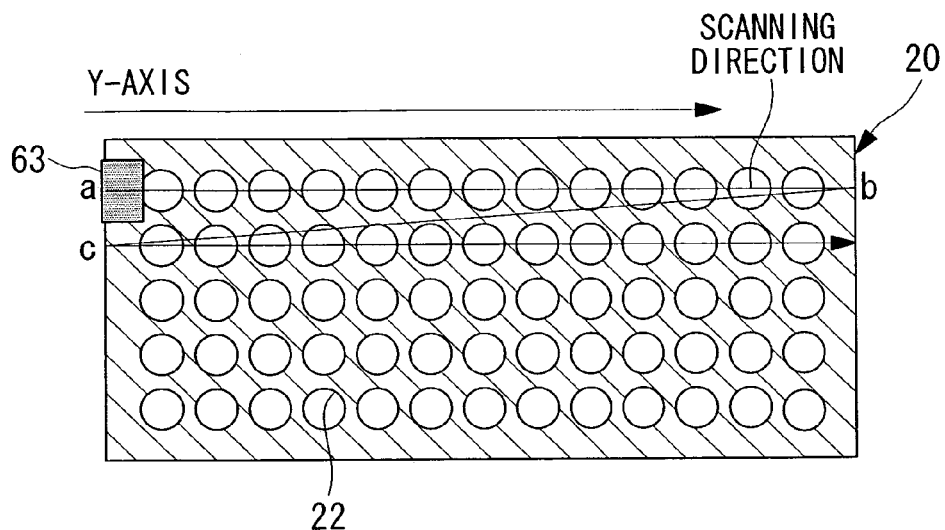
FIG. 6 depicts scanning in the TDI method.

FIG. 6 depicts the scanning in the TDI method. In this embodiment, the stage 30 is moved to perform scanning. However, in FIG. 6, for the sake of simplifying the drawing, the imaging device 63 is depicted as moving.

As shown in FIG. 6, when measuring the specimen 20 with the TDI method, the two-dimensional patterned portion 23 is completely scanned. This scanning is performed regardless of whether or not the sample located portions 22 are present.

When the stage 30 is scanned in the Y-axis direction, the stage 30 moves at constant velocity in the −Y direction. On the other hand, the imaging device 63 is capable of transferring charge only in one direction. Therefore, as shown in FIG. 6, measurement is carried out only while the stage 30 is advancing in the −Y direction. Measurement is not carried out while the stage 30 is advancing in the +Y direction. The motion in the +Y direction is for returning the stage to its initial position. The time required to return to the initial position may correspond to, for example, the time required for storing the acquired data in a hard disk of the computer 66.

First Embodiment

Next, a first embodiment of the present invention will be described. Here, a measurement procedure will be described using FIG. 7.

Figure 7:
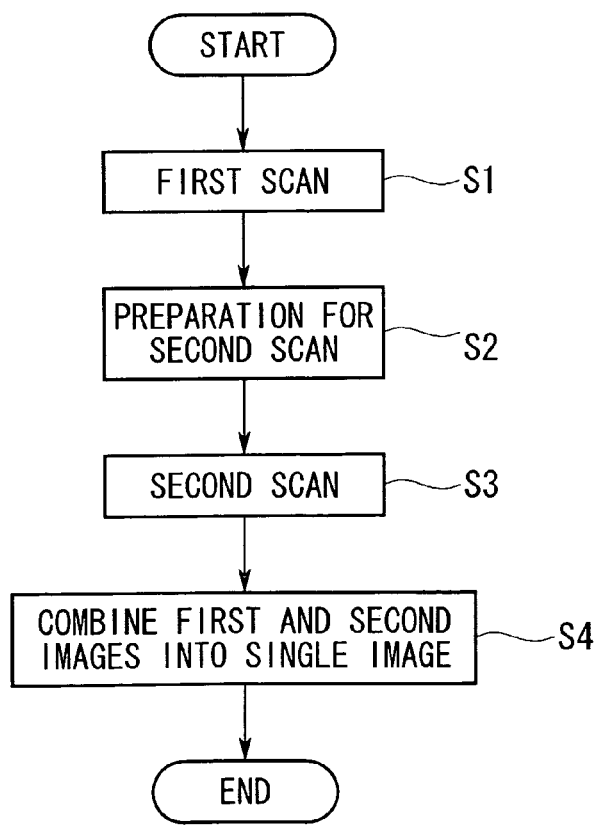
FIG. 7 is a flowchart showing a measurement procedure according to a first embodiment.
Figure 8A:
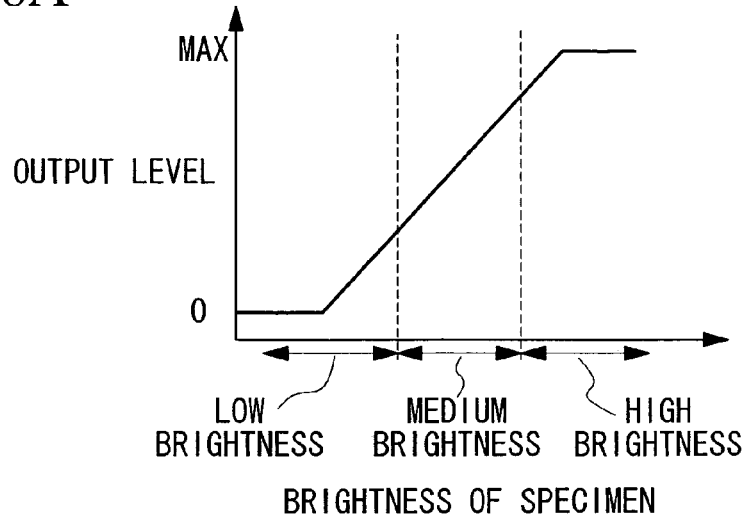
FIGS. 8A to 8C are graphs showing the relationship between specimen brightness and output level.
Figure 8B:
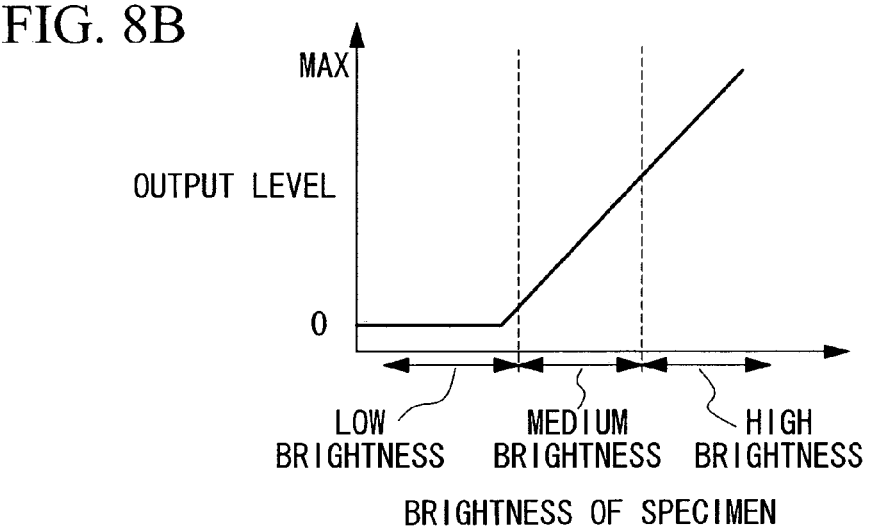
Figure 8C:
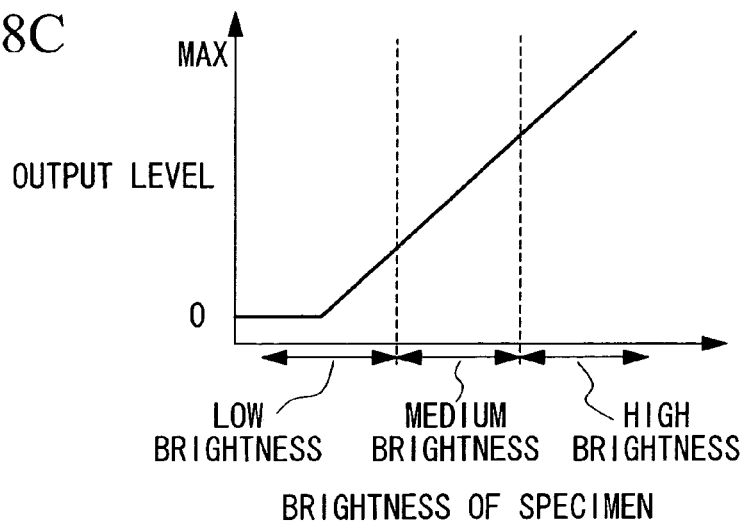

FIG. 7 is a flowchart showing the measurement procedure in this embodiment. FIGS. 8A to 8C show the relationship between the brightness of the specimen 20 and the output level from the imaging device 63. FIG. 8A shows the relationship between the brightness obtained in a first scan and the output level, FIG. 8B shows the relationship between the brightness obtained in a second scan and the output level, and FIG. 8C shows the dependency of the brightness obtained in the first and second scans no the output level.

First, the first scan (image acquisition) is performed to acquire an image of the specimen 20 (step S1). This corresponds to the prescan.

In this step, while the specimen 20 (stage 30) is moved from position a to position b shown in FIG. 6, the specimen 20 is imaged with a predetermined exposure time.

The image acquired in the first scan will be described in terms of the relationship between the brightness of the image and the output level from the imaging device 63. In this case, as shown in FIG. 8A, there is a region where the accumulated charge is saturated (hereinafter referred to as saturation-level region) and a region where the accumulated charge is low (hereinafter referred to as low-level region).

Next, preparation for the second scan is carried out (step S2).

The output levels of the saturation-level region and the low-level region are appropriately set. More specifically, exposure times of suitable length are set for each of these regions.

That is, when the saturation-level region is to be eliminated, the exposure time is set to be shorter than the exposure time in the first scan. At this time, the output level is set to utilize the entire dynamic range of the imaging device 63. When the low-level region is to be eliminated, the exposure time is set to be longer than the exposure time in the first scan. In this case too, the output level is set to utilize the entire dynamic range of the imaging device 63.

Simultaneously, the specimen 20 (stage 30) is moved from position b to position a.

This embodiment is described in terms of an example in which the saturation-level region is eliminated.

Next, a second scan (image acquisition) is performed to acquire an image of the specimen 20 again (step S3).

In this image acquisition, the exposure time determined in step S2 is used to acquire an image of the specimen 20 in the same way as in step S1.

The image acquired in the second scan is a graph indicating the relationship between the brightness of the acquired image and the output level of the imaging device 63. The image acquired in the second scan is shown in FIG. 8B. As shown in this figure, the saturation in the saturation-level region in the previous scan is eliminated, whereas the output level is increased in the low-level region.

Next, the images acquired in the first and second scans are combined into a single image (step S4). A predetermined image processing operation is carried out during this image combining.

In this step, the images acquired in steps S1 and S3 are combined. By doing so, a single image with wider dynamic range can be obtained.

Thus, in this embodiment, as shown in FIG. 8C, the image acquired in step S1 with the long exposure time and the image acquired in step S3 with the short exposure time are combined to form a single image.

Thereafter, the specimen 20 (stage 30) is moved from position b to position c, and the process proceeds to preparation for measuring the next line.

This embodiment has been described in terms of an example in which scanning of the same position is repeated twice. However, the number of scans is not limited to two.

For example, scanning may be repeated at the same position three or more times. In such a case, between the image acquisitions performed in each scan, preparation for the next scan is carried out, and the acquired images are combined at the end.

Instead of the imaging device 63 described above, an imaging device 63a having an electronic shutter may be used. Use of such an imaging device 63a is preferable since it can reduce the exposure time.

The electronic shutter is the type of shutter normally used in CCD digital cameras and mobile telephones with built-in cameras. Such an electronic shutter uses a phenomenon whereby charge is not accumulated if the CCD is not operating, even if exposed to light. Accordingly, the CCD function itself is one form of shuttering.

On the other hand, in a mechanical shutter used in a silver-halide camera, an opaque plate is placed between the lens and the film, and exposure is performed by opening and closing (moving) this plate. Thus, the electronic shutter is different from the mechanical shutter. The electronic shutter controls the exposure time without using a mechanical shutter.

Figure 9:
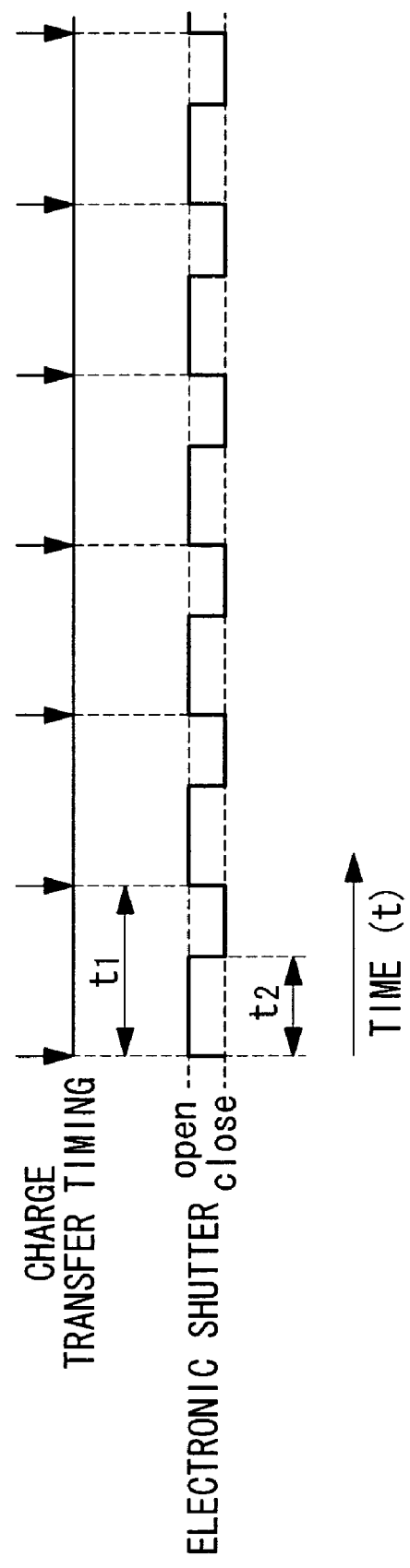
FIG. 9 is a timing chart for an electronic shutter used in the TDI method.

FIG. 9 is a timing chart for the electronic shutter in the TDI method.

As shown in FIG. 9, for example, when the maximum transfer rate in the TDI method is t1 (seconds), the charge is transferred to a neighboring horizontal line every t1 seconds. The timing of the transfers is indicated by the arrows in the figure.

The electronic shutter is open for a period of t2 seconds from each charge transfer, and charge accumulation is performed. In other words, the charge accumulation of the CCD is carried out for t2 seconds after every charge transfer. On the other hand, the exposure time when not using the electronic shutter is t1. Therefore, the ratio of the exposure time when using the electronic shutter to the exposure time when not using the electronic shutter is t2/t1.

For example, assume that the imaging device 63a has 1000 pixels in the Y direction and a maximum transfer rate (t1) of 10 kHZ (0.1 ms). When using this imaging device 63a to acquire images with an exposure time of 1 ms, the open time of the electronic shutter (t2) should be set to 0.001 ms, according to the calculation shown below:

1000×0.1 (ms)×(t2/0.1)=1 (ms)

t2=0.001 ms

When the electronic shutter is not used, the shortest exposure time is determined by the product of the maximum TDI transfer rate and the cumulative-number of pixels. Accordingly, by using an electronic shutter of the type described above, it is possible to increase the range of exposure times for which measurement is possible. Therefore, even a high-brightness specimen 20 can be accurately measured.

With the configuration described above, two images obtained by two scans with different exposure times in steps S1 and S3 are combined into a single image (S4). By doing so, it is possible to acquire an image with a wider dynamic range compared to an image acquired with a single exposure time. Therefore, it is possible to accurately carry out measurement even for a specimen 20 whose brightness variation is large.

Figure 10:
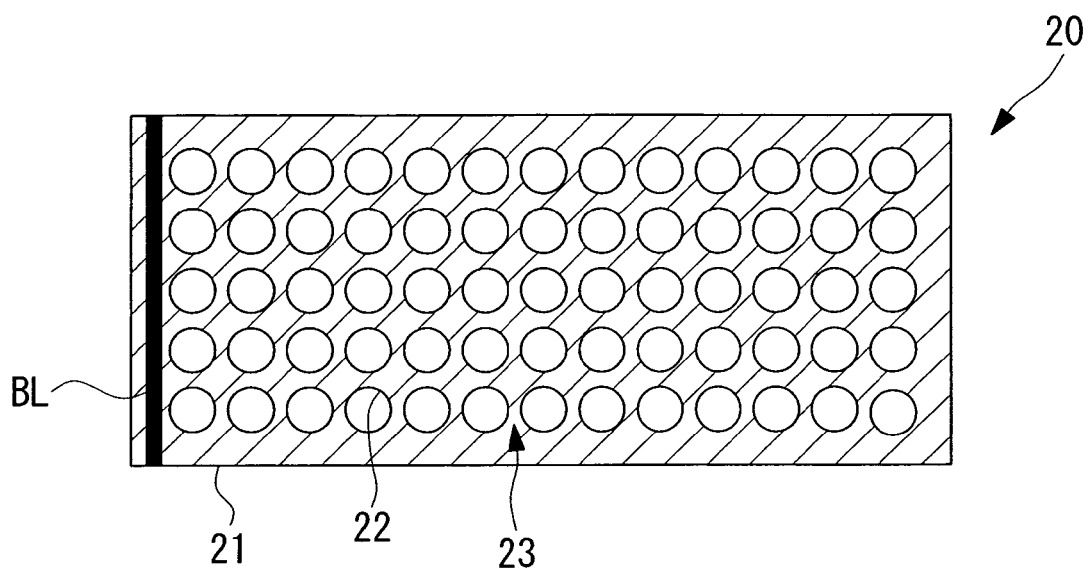
FIG. 10 shows another example of the structure of a specimen.

As shown in FIGS. 5A and 5B, the specimen 20 may include only the sample located portions 22 on the transparent substrate 21. Alternatively, as shown in FIG. 10, a reference line BL may also be formed in a region close to the left-hand side of the transparent substrate 21.

If the reference line BL is formed, it can serve as a reference when combining the images acquired in each scan. Accordingly, it is possible to simplify the image combining operation.

In this embodiment, since fluorescence examination is carried out, it is preferable that the reference line BL be formed of a material that fluoresces.

Second Embodiment

Next, a second embodiment of the present invention will be described with reference to FIGS. 11 to 13.

The basic structure of the microscope imaging apparatus of this embodiment is the same as that of the first embodiment, but the method of measuring the specimen is different from that in the first embodiment. Therefore, in this embodiment, only the method of measuring the specimen shall be described, using FIGS. 11 to 13, and a description of the TDI method and so on shall be omitted.

Figure 11:
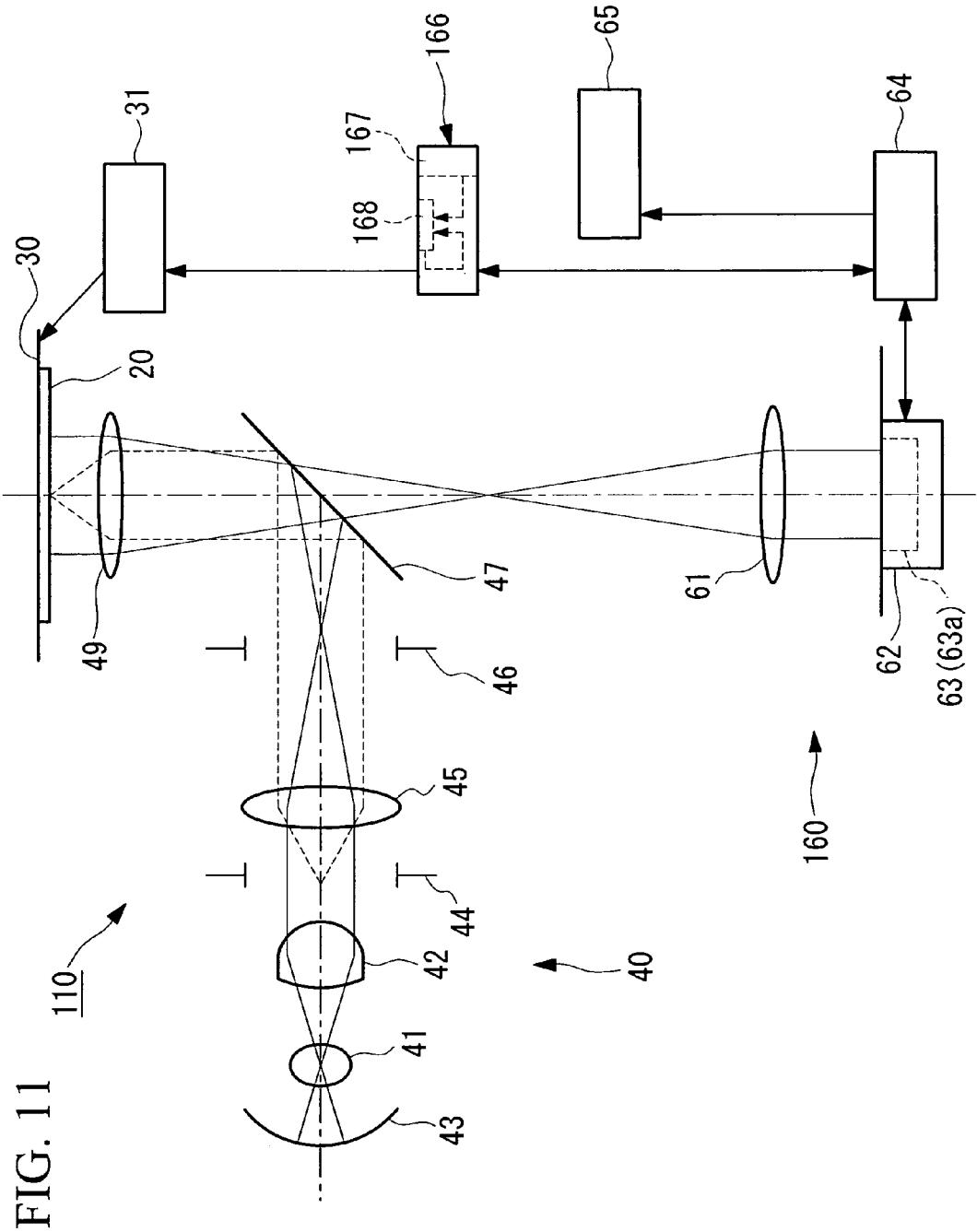
FIG. 11 shows the overall configuration of a microscope imaging apparatus according to a second embodiment.

FIG. 11 depicts the overall configuration of a microscope imaging apparatus 110 of this embodiment.

As shown in FIG. 11, the microscope imaging apparatus 110 includes a stage 30, an illumination unit 40, and an image-acquisition unit 160. The stage 30 holds a specimen 20 and is moveable. The illumination unit 40 irradiates the specimen 20 with illumination light. The image-acquisition unit 160 acquires signal light emitted from the region irradiated with illumination and measures it.

An imaging lens 61 and a detector 62 are provided in the image-acquisition unit 160. Return light from the specimen 20 is incident on the imaging lens 61, and the detector 62 detects the return light.

The detector 62 is connected to an image processing unit 64, which processes the output of the detector 62. The image processing unit 64, a monitor 65 for displaying the processed signal, and a stage driving mechanism 31 are connected to a computer 166.

An exposure-time input unit 167 and a setting unit 168 are provided in the computer 166. A maximum exposure time Tmax is input using the exposure-time input unit 167. This maximum exposure time Tmax is related to measurement of the specimen 20 and is set by the user. The setting unit 168 is used to set an exposure time Tmeasure used for image acquisition and measurement.

Next, the measurement procedure will be described.

Figure 12:
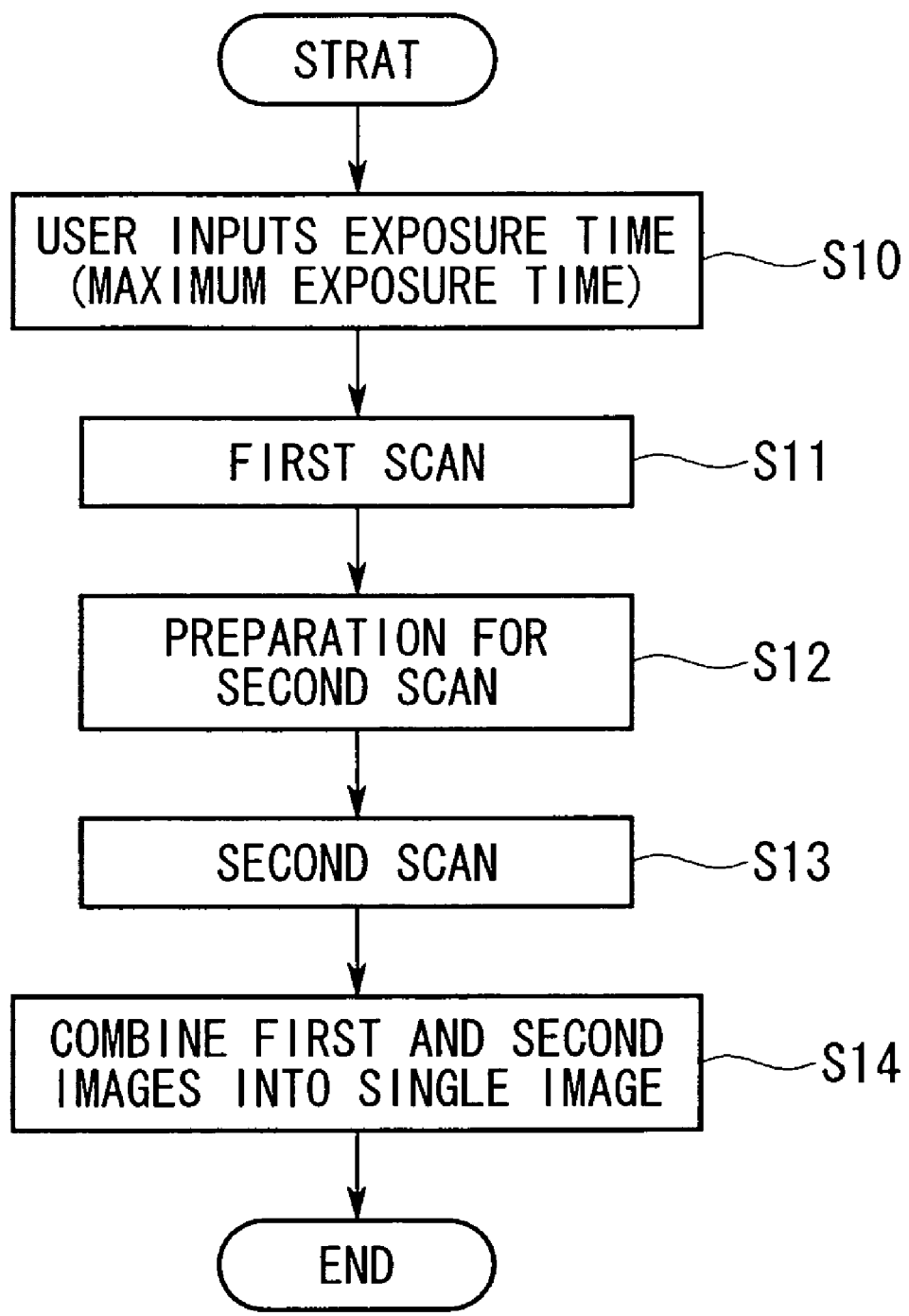
FIG. 12 is a flowchart showing a measurement procedure in the second embodiment.

FIG. 12 is a flowchart showing the measurement procedure in this embodiment.

First, the user sets the maximum exposure time Tmax (step S10) by inputting the maximum exposure time Tmax to the exposure-time input unit 167.

Next, a first scan (image acquisition) is performed to acquire an image of the specimen 20.

In this step, the maximum exposure time Tmax input to the setting unit 168 is set as the exposure time Tmeasure used for image acquisition and measurement. Therefore, an image of the specimen 20 is acquired with the maximum exposure time Tmax.

Next, preparation is arried out for a second scan (step S12).

In this step, the setting unit 168 sets the exposure time Tmeasure for the second scan on the basis of the magnitude (number of saturated pixels) in the saturation-level region.

Figure 13:
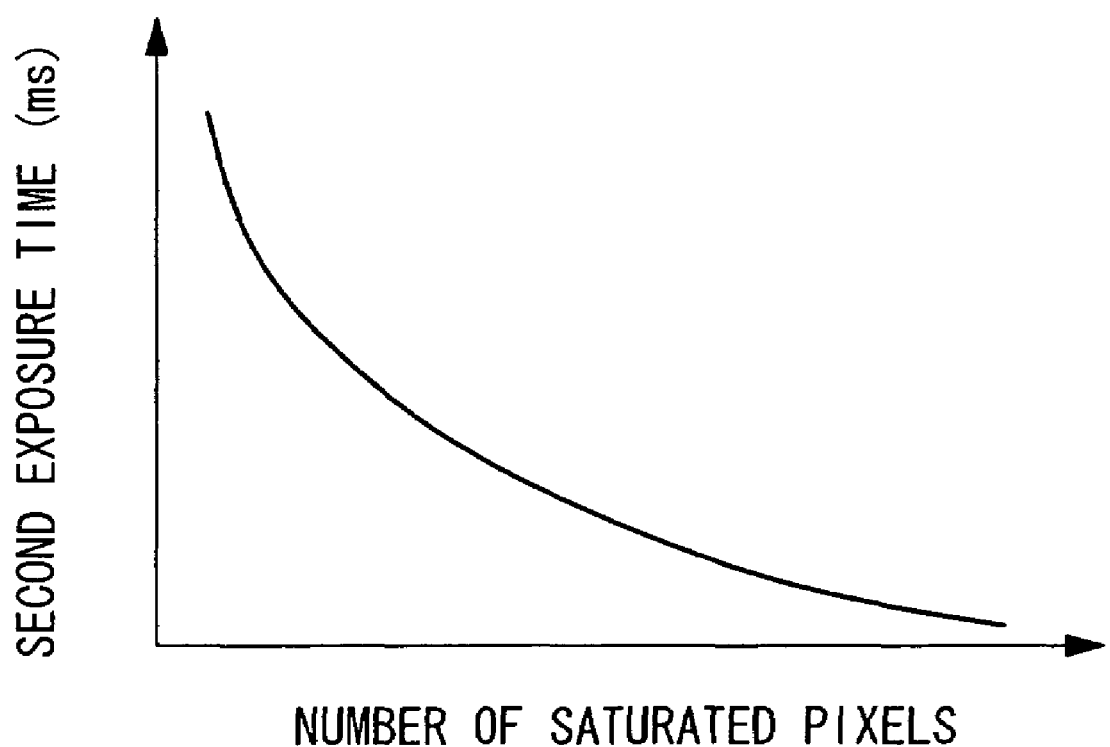
FIG. 13 is a graph showing the relationship between the number of saturated pixels and the exposure time used in the next image acquisition.

More specifically, as shown in FIG. 13, the relationship (table) between the number of saturated pixels and the exposure time in the next image acquisition is stored in the setting unit 168. On the basis of this table, the computer 66 sets the exposure time Tmeasure for the second scan. Thus, as the number of saturated pixels, for example, in each sample located portion 22 increases, the exposure time for the second scan decreases.

Saturated pixels shall now be explained. For example, if a 12-bit CCD is used as the imaging device 63, the maximum number of gradation levels is 4095 (=$2^{12}$, the maximum value that can be represented by 12 bits). Therefore, a saturated pixel is a pixel for which the imaging device outputs a value of 4095, in other words, a pixel whose output value reaches the upper limit.

Next, a second scan (image acquisition) is performed to acquire an image of the specimen 20 (step S13), and the images acquired in the first and second scans are combined to form a single image (step S14).

The measurement procedure after step S13 is the same as in the first embodiment, and therefore it is merely shown in FIG. 12, but a description thereof is omitted.

With the configuration described above, the user inputs the maximum exposure time Tmax in advance to the exposure-time input unit 167. By doing so, the exposure time can be reduced. Thus, image acquisition can be made more efficient, and it is possible to efficiently acquire images with a wider dynamic range.

This embodiment has been described in terms of an example in which the user sets the maximum exposure time. However, the time input to the exposure-time input unit 167 may be just the actual exposure time. In other words, it is not limited to the maximum exposure time.

Third Embodiment

Next, a third embodiment will be described with reference to FIGS. 14 and 15.

The basic configuration of the microscope imaging apparatus of this embodiment is the same as that in the first embodiment, but the configuration of the image-acquisition unit is different from the first embodiment. Therefore, in this embodiment only the image-acquisition unit will be described using FIGS. 14 and 15, and a description of the illumination unit and so on shall be omitted.

Figure 14:
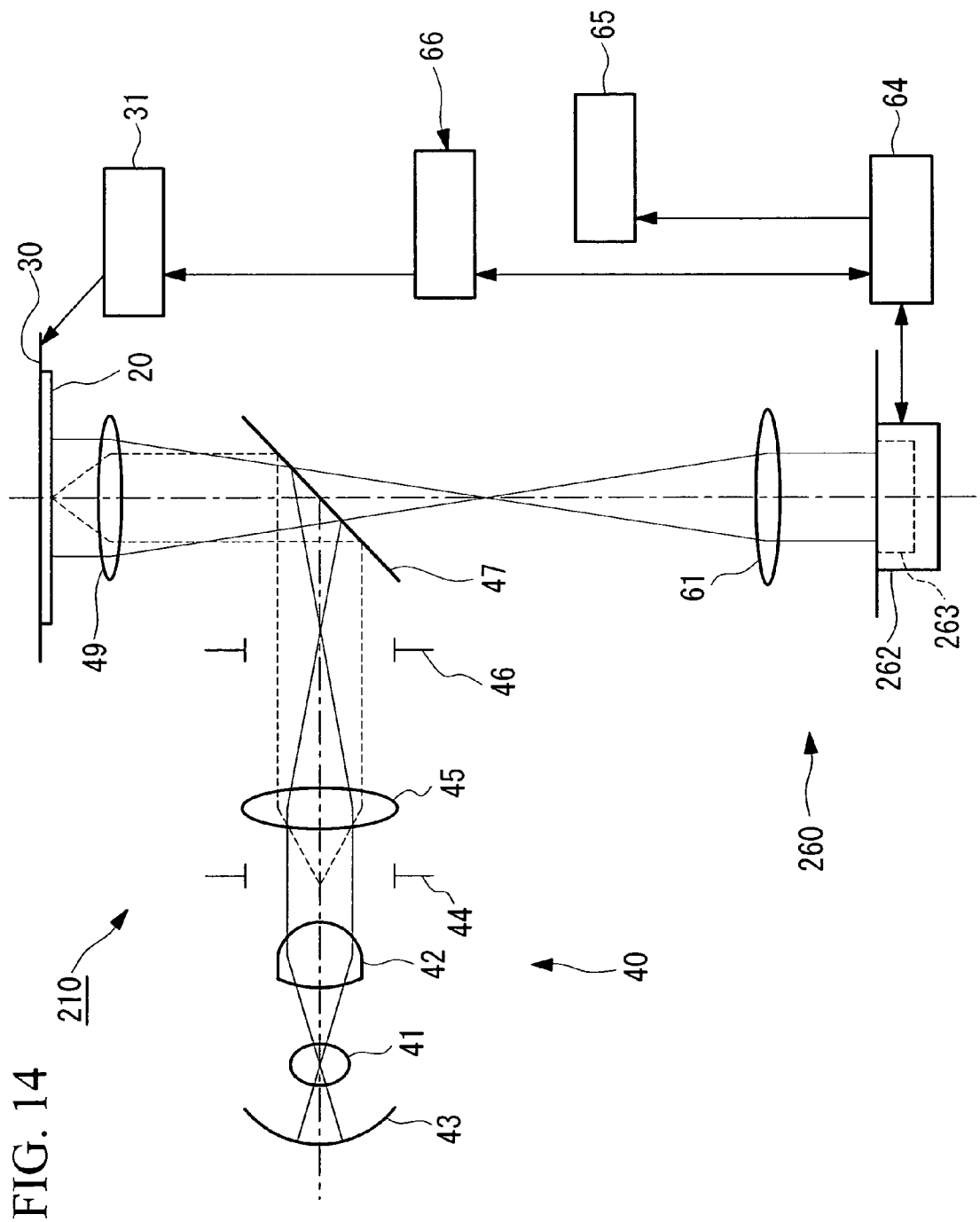
FIG. 14 shows the overall configuration of a microscope imaging apparatus according to a third embodiment.
Figure 15:
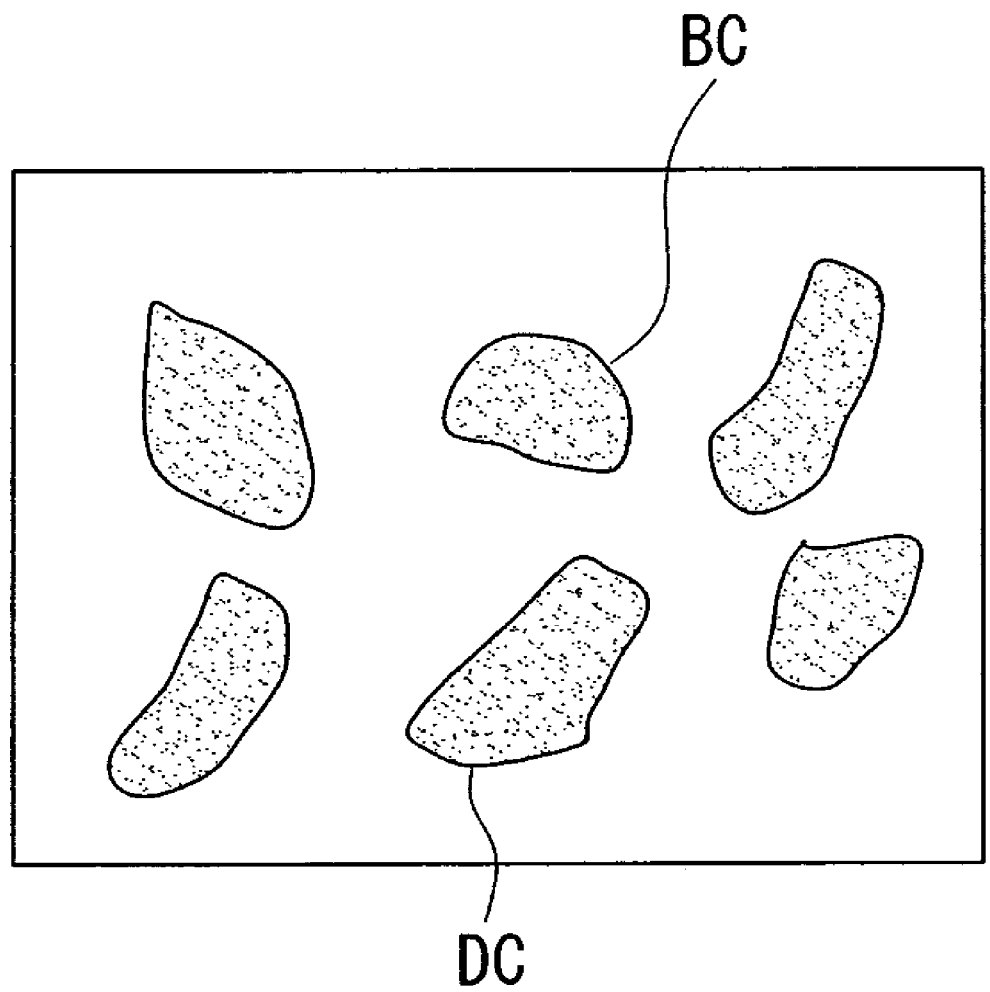
FIG. 15 depicts an image acquired in the third embodiment.

FIG. 14 shows the overall configuration of a microscope imaging apparatus 210 in this embodiment.

As shown in FIG. 12, the microscope imaging apparatus 210 includes a stage 30, an illumination unit 40, and an image-acquisition unit 260. The stage 30 holds a specimen 20 and is moveable. The illumination unit 40 irradiates the specimen 20 with illumination light. The image-acquisition unit 260 acquires signal light emitted from the region irradiated with the illumination light and measures it.

An imaging lens 61 and a detector 262 are provided in the image-acquisition unit 260. Return light from the specimen 20 is incident on the imaging lens 61, and the detector 262 detects the return light from the specimen 20. An imaging device 263 is disposed in the detector 262. The imaging device 263 has an anti-smear function and is capable of acquiring images on the basis of the TDI method. As described above, the TDI method is a technique in which, according to the motion of the stage 30, the signal charge in each horizontal line is accumulated in the imaging device 63.

Smearing is a phenomenon occurring in photoelectric conversion devices like CCDs (charge coupled devices). When an excessive signal above a certain level is input to a photoelectric conversion device, this phenomenon produces a false signal as a result of completely changing the signal in the longitudinal or transverse direction during signal processing.

That is, smearing is a phenomenon whereby, when a highly bright spot of light, for example, is incident on a photoelectric conversion device, a bright band of light extending in the longitudinal or transverse direction is produced.

It is possible to prevent the occurrence of smearing with the configuration described above. For example, as shown in FIG. 15, a cell BC of high brightness and a cell DC of low brightness are adjacent to each other. In this case, if the exposure time is long enough for the low-brightness cell (biological specimen) DC, smearing occurs in the image of the high-brightness cell BC. However, with the configuration described above, even if image acquisition is carried out with a long exposure time, which is suitable for the low-brightness cell DC, it is possible to prevent the occurrence of smearing. Therefore, it is possible to accurately measure both the high-brightness cell BC and the low-brightness cell DC.

When using an imaging device not having the anti-smear function, as described above, there is a risk of causing smearing at the low-brightness cell DC due to the high-brightness cell BC. As a result, it may not be possible to accurately measure the low-brightness cell DC.

With the microscope imaging apparatus of this embodiment, when acquiring a plurality of images of the object under examination, it is possible to acquire images with different exposure times. Then, these images are combined into a single image. By doing so, it is possible to accurately perform measurement even for an examination object having significant brightness variation.

Fourth Embodiment

Next, a fourth embodiment will be described. The microscope imaging apparatus shown in FIG. 4 is also used in this embodiment. The measurement procedure shall be described using FIG. 16.

Figure 16:
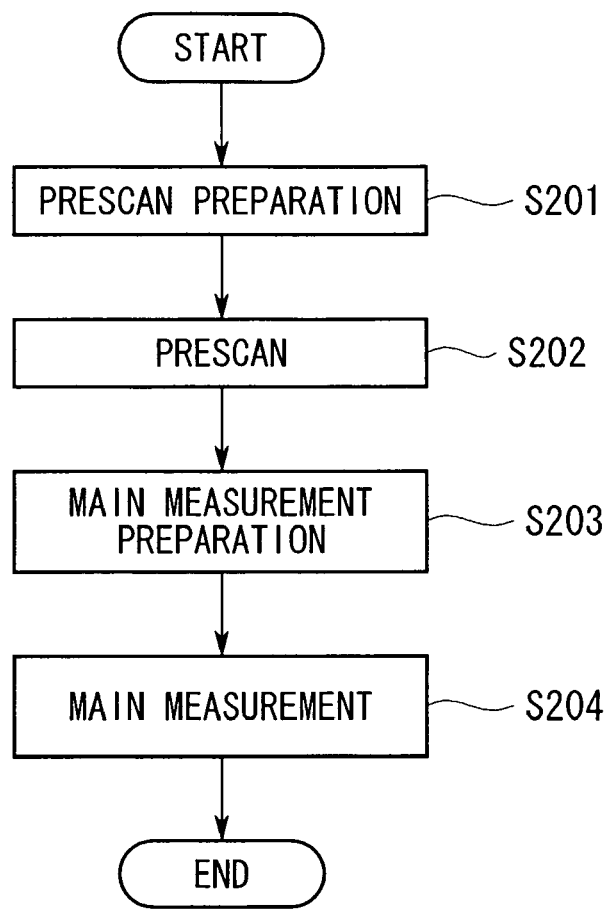
FIG. 16 is a flowchart showing a measurement procedure in a fourth embodiment.

FIG. 16 is a flowchart showing the measurement procedure in this embodiment.

First, when measurement commences, prescan preparation is carried out (step S201). In this step, the stage 30 moves to a measurement starting point (the point where the imaging device 63 and the specimen 20 have the positional relationship shown in FIG. 6).

Next, the prescan is carried out (step S202). Fluorescence, for example, is emitted from each of the sample located portions 22, and the prescan is performed to acquire the brightness distribution of this fluorescence. The exposure time used in the prescan is set to be sufficiently short so that the signal charge accumulated in the imaging device 63 is not saturated. As described above, the movement speed of the stage 30 is set according to the TDI line transfer rate.

Figure 17:
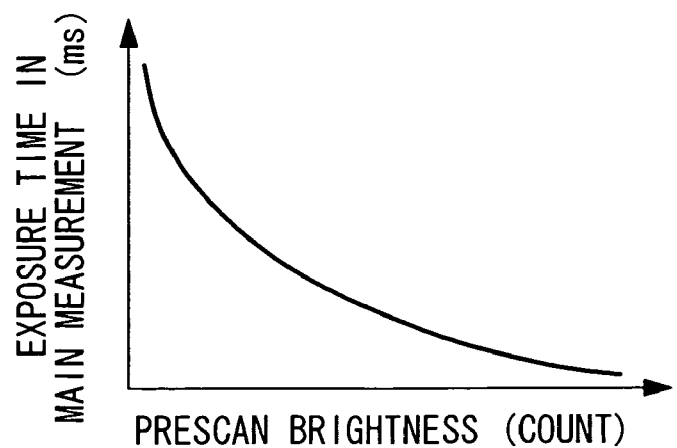
FIG. 17 is a graph showing the relationship between prescan brightness and exposure time of the main measurement.

FIG. 17 is graph showing the relationship between the prescan brightness and the exposure time in the main measurement.

When the prescan is completed, preparation for the main measurement of the specimen 20 is carried out (step S203). In this step, the stage 30 is moved back to the measurement starting point.

The brightness in each sample located portion 22 has already been acquired in the prescan (step S202). Therefore, from among the acquired brightnesses, the maximum value, that is, the maximum intensity value (count), is found. This maximum intensity value is the digital value output from the imaging device 63.

Then, on the basis of the maximum intensity value, the exposure time for each sample located portion 22 in the current measurement is determined. The exposure time is determined on the basis of the relationship between the prescan brightness and the exposure time for the main measurement, as shown in FIG. 17. The relationship shown in FIG. 17 is obtained in advance before measurement. (For example, the relationship shown in FIG. 17 is obtained by measurement or simulation.)

Once the exposure time has been determined, the main measurement (image acquisition) of the specimen 20 is carried out (step S204). In this step, the image of each sample located portion 22 is acquired on the basis of the exposure time found in the main-measurement preparation step (step S203). As described above, the exposure time is expressed by the TDI line transfer rate and the cumulative number of charged pixels. Also, the stage 30 is moved at a speed in synchronization with the TDI line transfer rate.

In this embodiment too, instead of the imaging device 63 described above, an imaging device 63*a* having an electronic shutter may be used. Use of such an imaging device 63*a* is beneficial in that it is possible to reduce the exposure time. The electronic shutter and the mechanical shutter are as described previously.

The TDI method is also used in this embodiment. The timing chart for the electronic shutter used in this TDI method is as shown in FIG. 9.

With the configuration described above, it is possible to obtain a suitable exposure time for measurement of the specimen 20 on the basis of the prescan performed before measurement of the specimen 20. Accordingly, on the basis of the prescan before measurement, a suitable exposure time can be determined even when measuring a specimen 20 whose brightness changes with time. As a result, the specimen can be accurately measured.

More concretely, setting an exposure time longer than the appropriate time can prevent the problem of saturation of the accumulated charge. Also, setting an exposure time shorter than the appropriate time can prevent the problem of insufficient charge accumulation (only accumulating the noise level).

Figure 18:
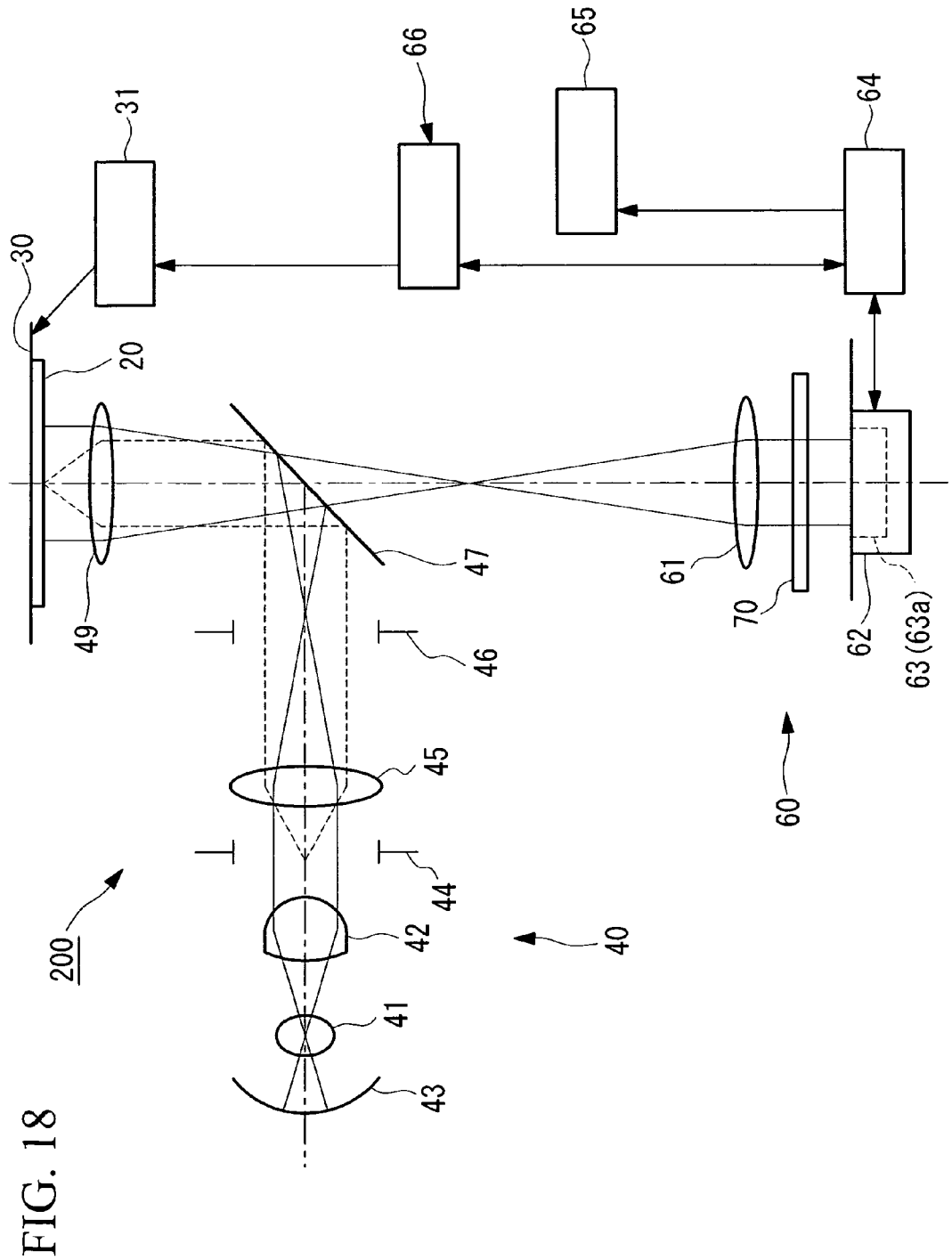
FIG. 18 shows another example of the microscope imaging apparatus in the fourth embodiment.

FIG. 18 shows an example of the configuration of another microscope imaging apparatus 200. As shown in FIG. 18, for example, a light control member 70 may be disposed between the imaging lens 61 and the detector 62 in the image-acquisition unit 60. For example, a neutral density (ND) filter or an electro-micro mirror device whose transmittance is varied by application of an electric potential may be used as the light control member 70.

With the configuration described above, the transmittance of the light control member 70 can be adjusted according to the exposure time obtained in the prescan. Thus, the range of possible exposure times for measurement can be increased. As a result, it is possible to accurately carry out measurement even for a specimen 20 having high brightness or low brightness.

Fifth Embodiment

Next, a fifth embodiment will be described with reference to FIG. 19.

The basic configuration of the microscope imaging apparatus of this embodiment is the same as that of the fourth embodiment, but the prescan method is different from that in the fourth embodiment. Therefore, in this embodiment, only the prescan method is described using FIG. 19, and a description of the main measurement method and so on is omitted.

Figure 19:
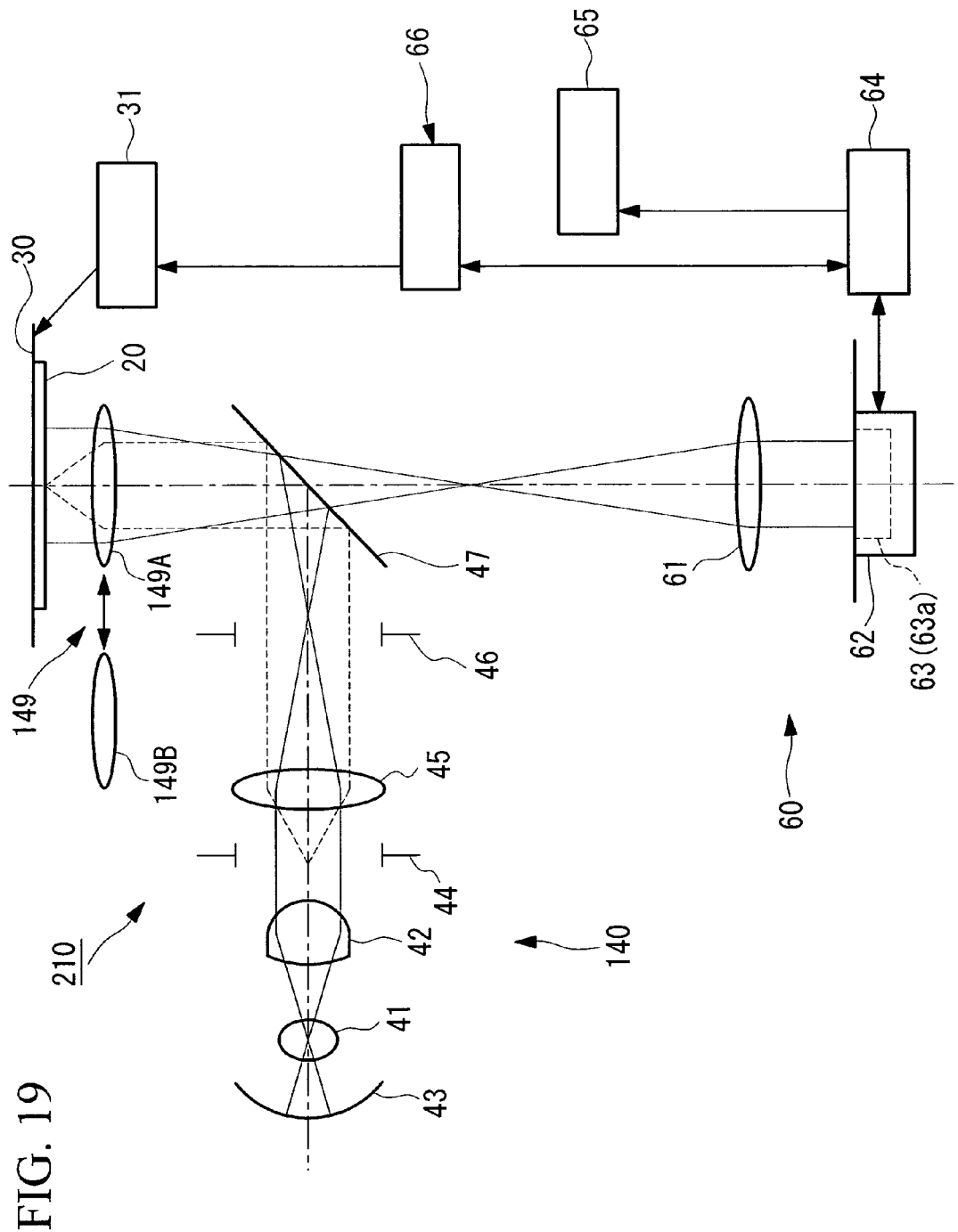
FIG. 19 shows the overall configuration of a microscope imaging apparatus in a fifth embodiment.

FIG. 19 shows the overall configuration of a microscope imaging apparatus 210 of this embodiment.

As shown in FIG. 19, the microscope imaging apparatus 210 includes a stage 30, an illumination unit 140, and an image-acquisition unit 60. The stage 30 holds a specimen 20 and is moveable. The illumination unit 140 irradiates the specimen 20 with illumination light. The image-acquisition unit 60 acquires signal light emitted from the region irradiated with the illumination light and measures it.

A light source lamp 41, a collector lens 42, a reflecting mirror 43, a field stop 44, a lens 45, an aperture stop 46, and a mirror 47 are provided in the illumination unit 140. The collector lens 42 collects light emitted from the lamp 41. The reflecting mirror 43 reflects backward-propagating light back to the lamp 41. The diameter of the opening of the field stop 44 can be adjusted. The lens 45 images the field stop 44 at infinity. The diameter of the opening of the aperture stop 46 can be adjusted. The mirror 47 selectively transmits light. An objective lens 149 forms an image of the specimen 20; however, since the objective lens 149 focuses the light from the lamp 41 on the specimen 20, it can also be considered part of the illumination unit 140.

A low-magnification objective lens 149A used in the prescan and a high-magnification objective lens 149B used in the main measurement are used as the objective lens 149. These objective lenses 149A and 149B are retained by a known switching mechanism such as a revolver or the like. Thus, it is possible to change the objective lens as required.

With the configuration described above, since it is possible to acquire a wide-field image during the prescan, the prescan time can be shortened.

For example, the high-magnification objective lens 149B used in the main measurement is a 20× lens, and the low-magnification objective lens 149A used in the prescan is a 4× lens. Thus, because the pixel pitch on the stage 30 is five times larger, the stage speed can be increased by a factor of five. Furthermore, because the field is five times wider, the number of line scans can be reduced to one fifth. Therefore, compared to the case where the prescan and the main measurement are carried out with the same magnification, the prescan time required for the entire surface of the specimen 20 can be reduced to ¹/25.

Also, the light (brightness) from the specimen may vary over time, depending on the specimen. In such a case, the appropriate exposure time also changes over time. Therefore, if the time required for the prescan can be reduced, as in this embodiment, it is possible to reduce the time interval from the prescan to the main measurement. As a result, it is possible to carry out measurement with the appropriate exposure time.

Sixth Embodiment

Next, a sixth embodiment will be described with reference to FIG. 20.

The basic configuration of the microscope imaging apparatus of this embodiment is the same as that of the fourth embodiment, but the image-acquisition unit is different from that in the fourth embodiment. Therefore, in this embodiment, only the image-acquisition unit is described using FIG. 20, and a description of the illumination unit and so on is omitted.

Figure 20:
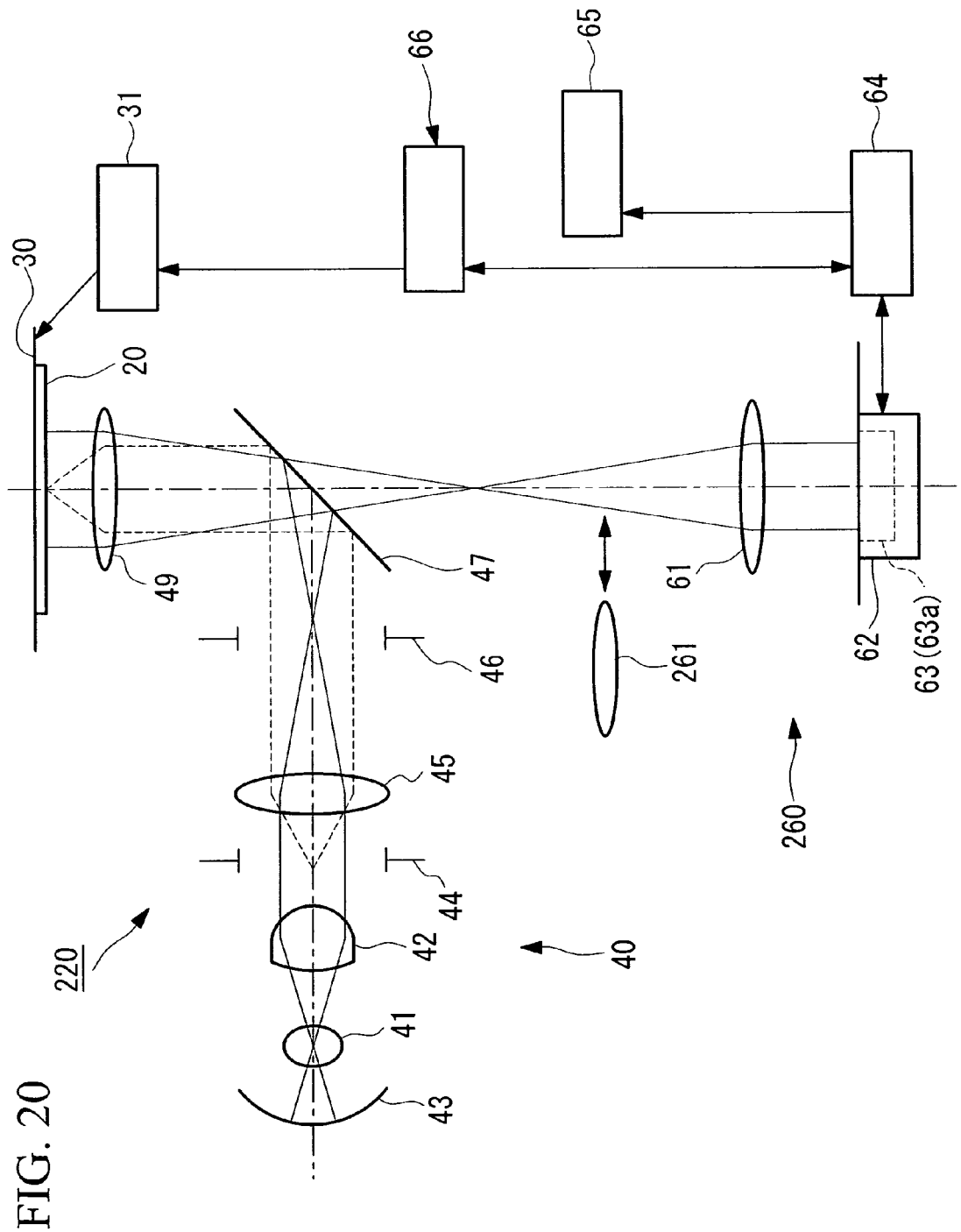
FIG. 20 shows the overall configuration of a microscope imaging apparatus in a sixth embodiment.

FIG. 20 shows the overall configuration of a microscope imaging apparatus 220 of this embodiment.

As shown in FIG. 20, the microscope imaging apparatus 220 includes a stage 30, an illumination unit 40, and an image-acquisition unit 260. The stage 30 holds a specimen 20 and is moveable. The illumination unit 40 irradiates the specimen 20 with illumination light. The image-acquisition unit 260 acquires signal light emitted from the region irradiates with the illumination light and measures it.

An imaging lens 61, a detector 62, and a scaling lens 261 are provided in the image-acquisition unit 260. Return light from the specimen 20 is incident on the imaging lens 61. The detector 62 detects the return light from the specimen 20. The scaling lens 261 can acquire images over a wide field.

The scaling lens 261 is inserted into the light path between the objective lens 49 and the detector 62. It may be capable of being inserted in and removed from the light path. Also, the scaling lens 261 may be retained by a known switching mechanism such as a revolver. By doing so, it is possible to switch between scaling lenses with different magnifications, as required.

With the configuration described above, by inserting the scaling lens 261 into the light path between the objective lens 49 and the detector 62 during the prescan, it is possible to acquire images over a wide field of view. Accordingly, the prescan time can be reduced.

Furthermore, since it is possible to reduce the time interval from the prescan to the main measurement, even for a specimen 20 whose brightness varies with time, it is possible to carry out measurement with the appropriate exposure time.

Seventh Embodiment

Next, a seventh embodiment will be described with reference to FIGS. 21 and 22.

The basic configuration of the microscope imaging apparatus of this embodiment is the same as that of the fourth embodiment, but the method of controlling the exposure time is different from that in the fourth embodiment. Therefore, only the method of controlling the exposure time is described using FIGS. 21 and 22, and a description of the structure and so on is omitted.

Figure 21:
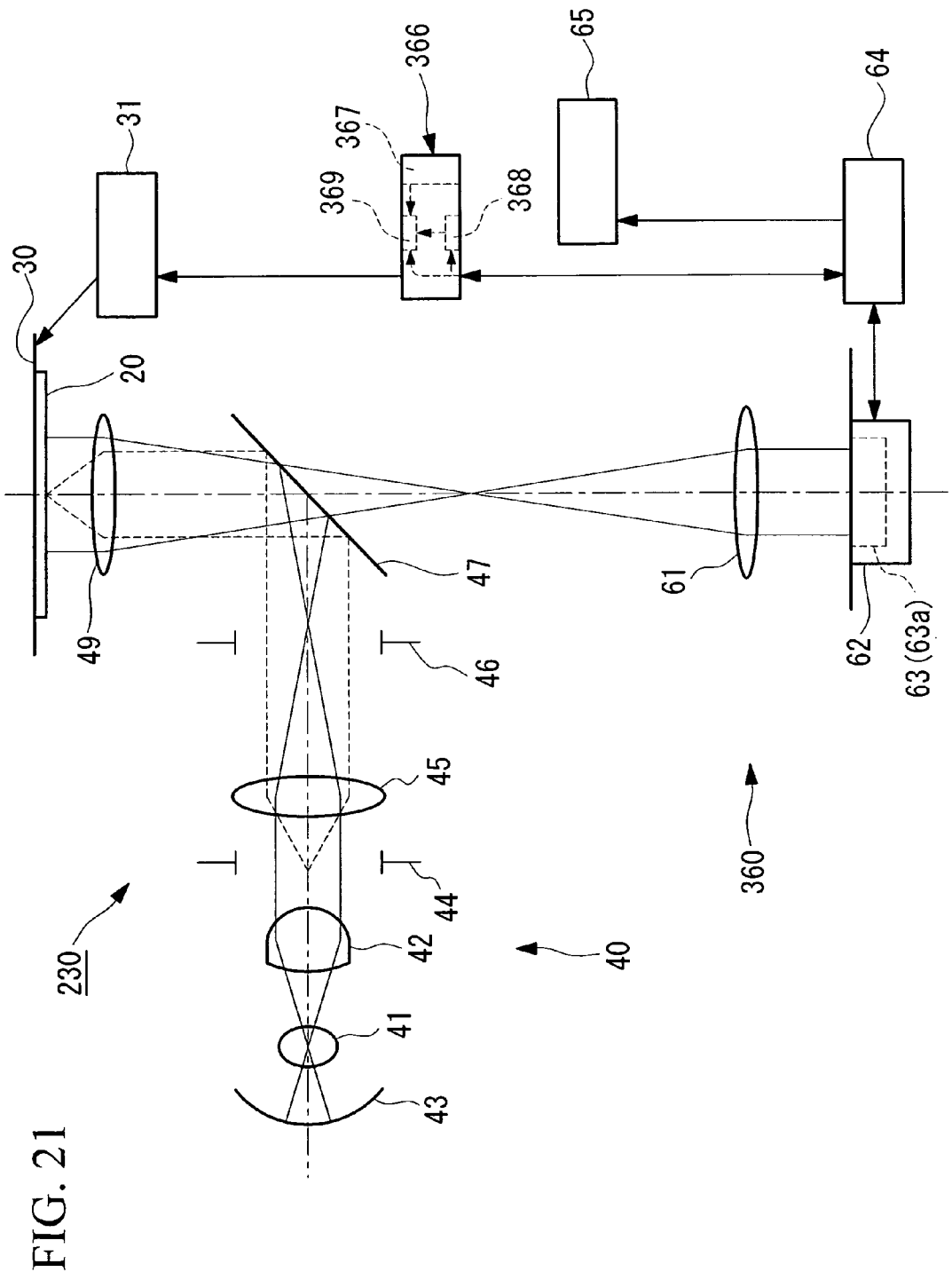
FIG. 21 shows the overall configuration of a microscope imaging apparatus in a seventh embodiment.

FIG. 21 shows the overall configuration of a microscope imaging apparatus 230 in this embodiment. FIG. 22 is a flowchart showing the measurement procedure in this embodiment.

As shown in FIG. 21, the microscope imaging apparatus 230 includes a stage 30, an illumination unit 40, and an image-acquisition unit 360. The stage 30 holds a specimen 20 and is moveable. The illumination unit 40 irradiates the specimen 20 with illumination light. The image-acquisition unit 360 acquires signal light emitted from the region irradiated with the illumination light and measures it.

An imaging lens 61 and a detector 62 are provided in the image-acquisition unit 360. Return light from the specimen 20 is incident on the imaging lens 61. The detector 62 detects the return light from the specimen 20.

The detector 62 is connected to an image processing unit 64, which processes the output from the detector 62. A monitor 65 for displaying the processed signal is connected to the image processing unit 64. A stage driving mechanism 31 is connected to a computer 366.

The computer 366 includes a maximum-exposure-time input unit 367, a calculating unit 368, and a selecting unit 369. A maximum exposure time Tmax for measuring the specimen 20 is input to the maximum-exposure-time input unit 367. The maximum exposure time Tmax is set by the user. The calculating unit 368 calculates an exposure time Tpre on the basis of information obtained in a prescan. The selecting unit 369 carries out comparison and selection of the exposure time Tpre and the maximum exposure time Tmax.

Next, the measurement procedure will be described.

Figure 22:
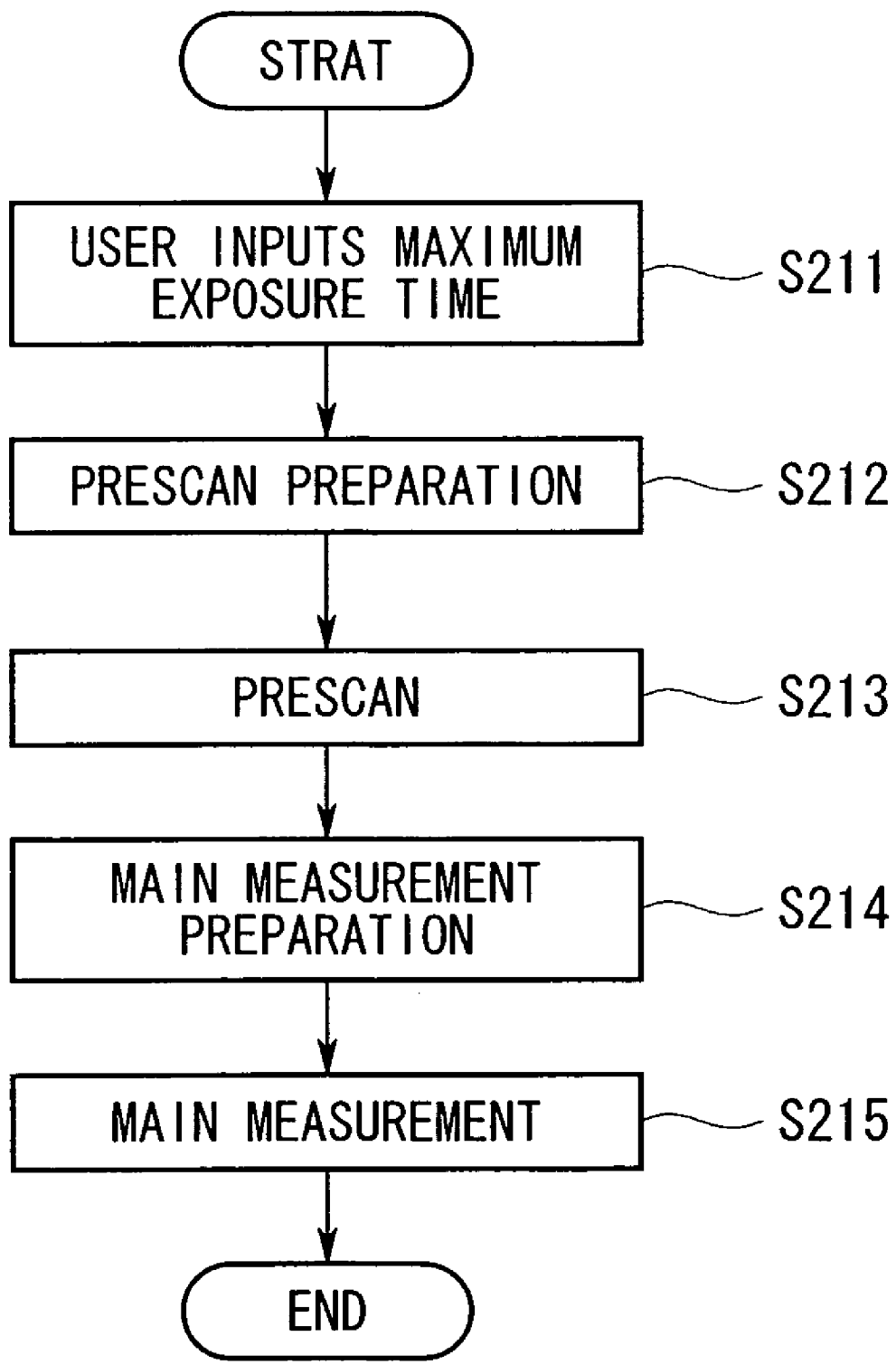
FIG. 22 is a flowchart showing a measurement procedure in the seventh embodiment.

As shown in FIG. 22, first, the user inputs the maximum exposure time Tmax for the main measurement (step S211). Then, measurement commences.

Next, prescan preparation is carried out (step S212). In this step, the stage 30 moves to a measurement starting point (the point where the imaging device 63 and the specimen 20 have the positional relationship shown in FIG. 6)

Next, the prescan is performed (step S213). Fluorescence, for example, is emitted from each sample located portion 22, and the prescan is performed to acquire brightness distribution information of this fluorescence. The exposure time in the prescan is set to a sufficiently short duration so that, for example, the signal charge accumulated in the imaging device 63 is not saturated. Also, as described above, the movement speed of the stage 30 is set according to the TDI line transfer rate.

Once the prescan has been completed, preparation for the main measurement of the specimen 20 is carried out (step S214). In this step, the stage 30 is moved back to the measurement starting point.

The brightness in each sample located portion 22 has already been acquired in the prescan (S213). Thus, a maximum value, that is, a maximum intensity value (count), is found from among the acquired brightnesses. This maximum intensity value is a digital value output from the imaging device 63.

Then, the exposure time Tpre for each sample located portion 22 is determined on the basis of the maximum intensity value found. The exposure time Tpre is determined on the basis of the relationship between the prescan brightness and the exposure time in the main measurement, as shown in FIG. 17. The relationship shown in FIG. 17 is determined in advance before the measurement. (For example, the relationship shown in FIG. 17 is determined by measurement or simulation.)

Here, the maximum exposure time Tmax and the exposure time Tpre are compared. On the basis of the comparison result, if the exposure time Tpre is shorter than the maximum exposure time Tmax, the exposure time Tpre is used as the exposure time for the main measurement. On the other hand, if the exposure time Tpre is longer than the maximum exposure time Tmax, the maximum exposure time Tmax is used as the exposure time in the main measurement.

When the exposure time has been determined, the main measurement (image acquisition) of the specimen 20 is carried out (S215). In this step, an image of each sample located portion 22 is acquired on the basis of the exposure time determined in the main measurement preparation (step S214). As described above, the exposure time is given by the TDI line transfer rate and the cumulative number of charged pixels. Also, the stage 30 is moved at a speed in synchronization with the TDI line transfer rate.

By setting the exposure time as described above, it is possible to prevent the exposure time from becoming too long when carrying out the main measurement of a specimen 20 having low brightness. Moreover, it is possible to measure a specimen 20 whose brightness varies over time using the appropriate exposure time.

Eighth Embodiment

Next, an eighth embodiment will be described with reference to FIGS. 23A and 23B.

The basic configuration of the microscope imaging apparatus of this embodiment is the same as that in the fourth embodiment, but the specimen is different from that in the fourth embodiment. Therefore, only the specimen is described using FIGS. 23A and 23B, and a description of the illumination unit and so on is omitted.

Figure 23A:
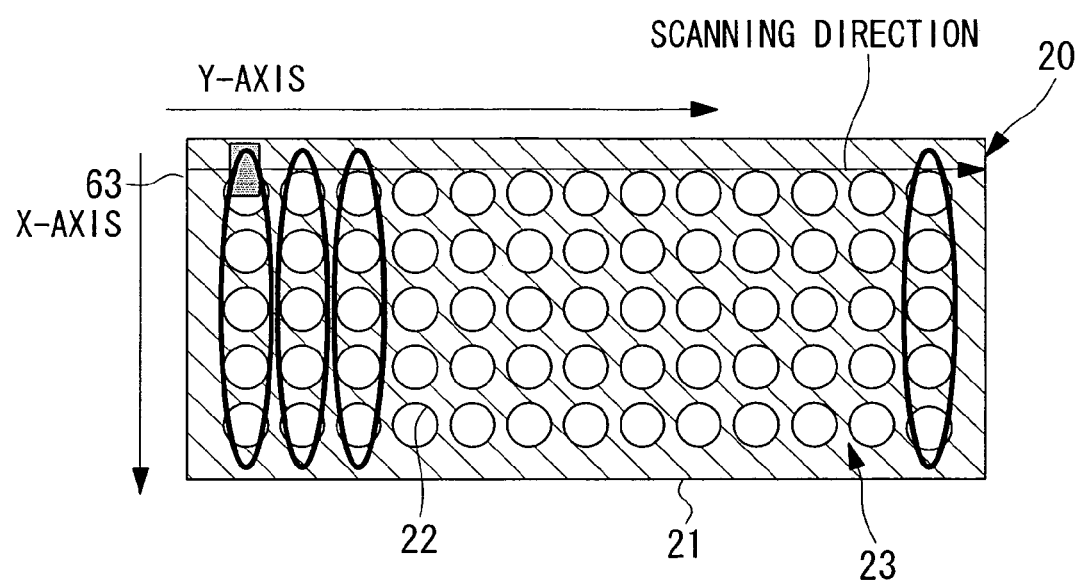
FIGS. 23A and 23B depict the structure of a specimen in an eighth embodiment.
Figure 23B:
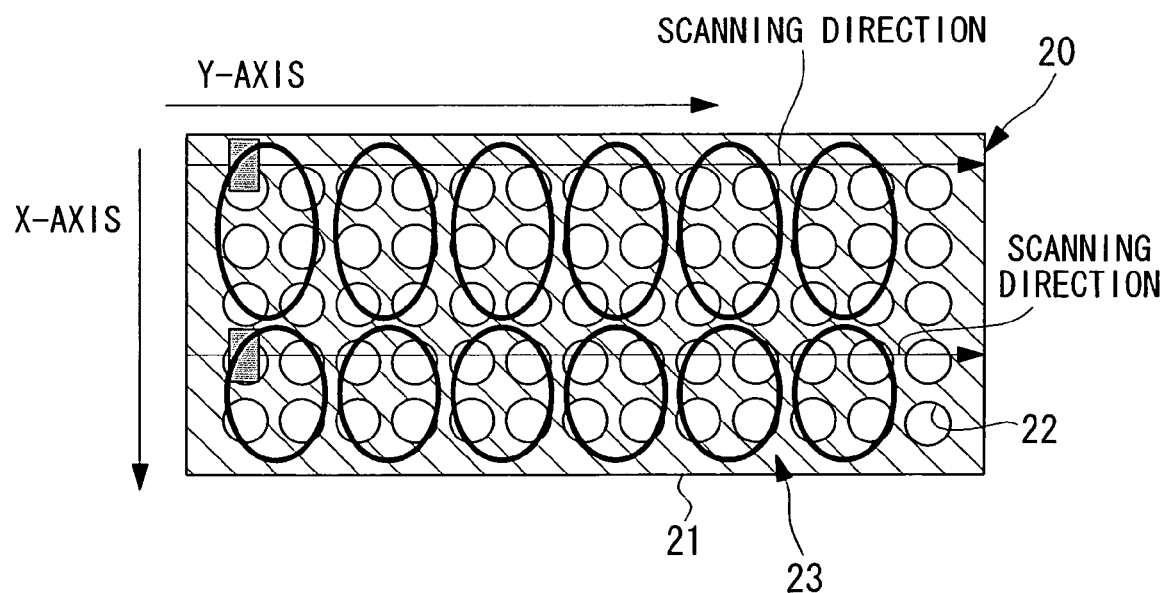

FIGS. 23A and 23B show the configuration of a specimen 20 in this embodiment.

As shown in FIG. 23A, the specimen 20 is disposed so that the brightness in the sample located portions 22 arrayed in the X direction (the sample located portions 22 enclosed by the ellipses in FIG. 23A) is substantially uniform.

With the configuration described above, by performing the prescan in one row in the Y direction in FIG. 23A, it is possible to obtain an appropriate exposure time. Accordingly, the time required for the prescan can be reduced.

The specimen 20 may be arranged as shown in FIG. 23A. Also, as shown in FIG. 23B, sample located portions 22 having substantially uniform brightness may be arranged so as to be grouped in regions formed of two or three rows in the X direction and two rows in the Y direction (the region enclosed by the ellipses in FIG. 23B).

By adopting such an arrangement, as shown in FIG. 23B, it is possible to achieve the appropriate exposure time by performing the prescan in two rows. Therefore, the time required for the prescan can be reduced.

The arrangement of the sample located portions 22 having substantially uniform brightness is not particularly limited; any arrangement is possible so long as the number of prescans can be reduced.

With the microscope imaging apparatus of this embodiment, it is possible to achieve an appropriate exposure time for measuring the object under examination on the basis of the prescan performed before the main measurement. Therefore, a specimen whose brightness varies over time can be accurately measured.

Ninth Embodiment

Figure 24:
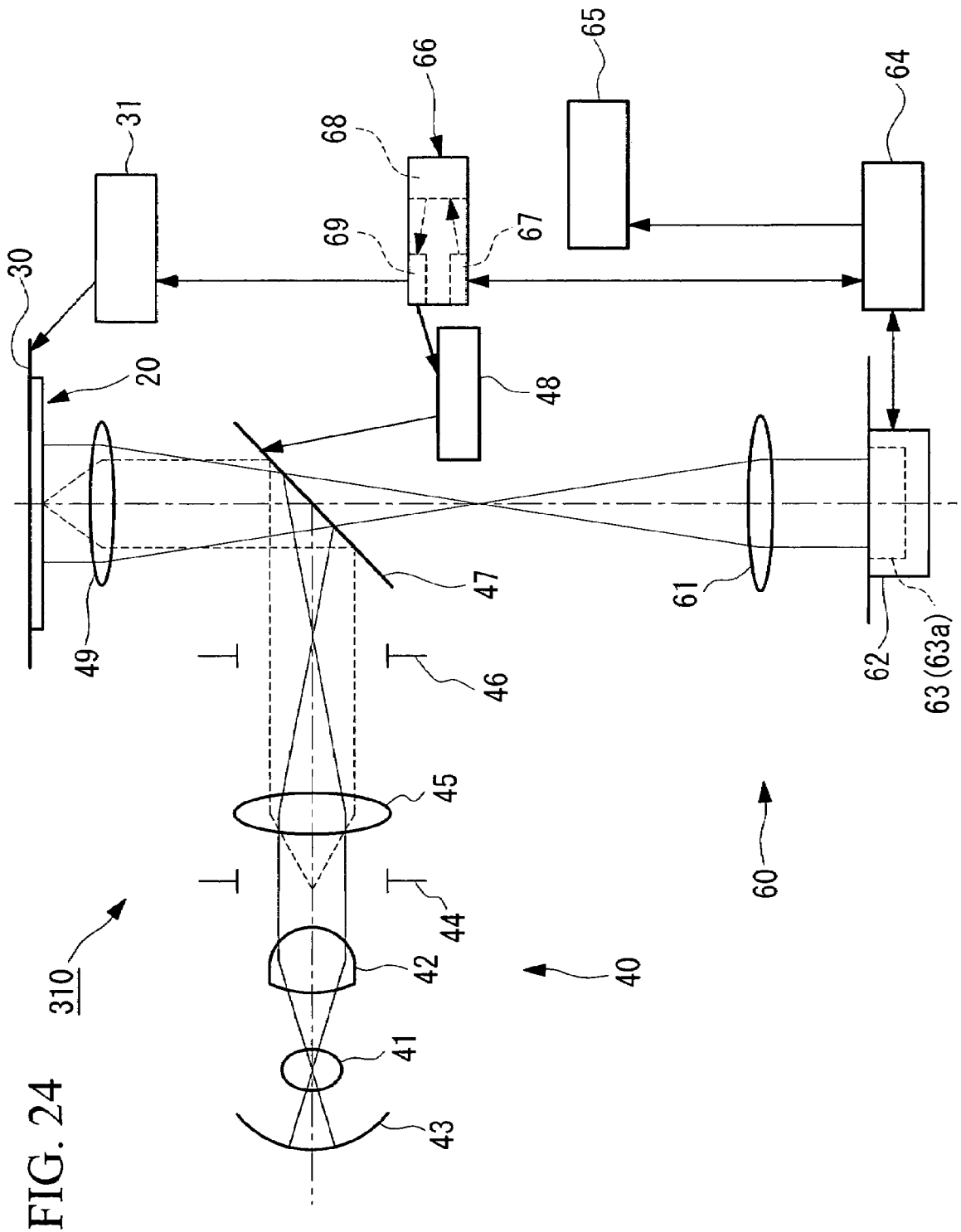
FIG. 24 shows the overall configuration of a microscope imaging apparatus in a ninth embodiment.

A ninth embodiment will now be described. FIG. 24 shows the overall configuration of a microscope imaging apparatus 310 of this embodiment. Components that are the same as those in FIG. 4 are assigned the same reference numeral, and a description thereof shall be omitted.

With the microscope imaging apparatus 310 of this embodiment, it is possible to acquire images by the TDI method and by a two-dimensional imaging method.

An imaging lens 61 and a detector 62 are provided in an image-acquisition unit 60. Return light (fluorescence) from the specimen 20 is incident on the imaging lens 61. The imaging lens 61 focuses (images) the incident light at a predetermined position. The detector 62 is disposed at the predetermined position and detects the return light from the specimen 20. An imaging device 63 that is capable of the TDI method and the two-dimensional imaging method is provided in the detector 62.

The output from the detector 62 is connected to an image processing unit 64 that processes the signal output from the detector 62. A monitor 65 for displaying the processed signal is connected to the image processing unit 64. The image processing unit 64 is connected to a computer 66. A mirror driving mechanism 48 and a stage driving mechanism 31 are also connected to the computer 66.

The computer 66 is provided with a specimen-parameter input unit (examination-object-parameter input unit) 67, a calculating unit 68, and a switching unit 69. The specimen-parameter input unit 67 obtains and inputs information on the specimen 20 in advance. The calculation unit 68 calculates the scanning time for the stage 30 on the basis of the specimen parameters output from the specimen-parameter input unit 67. The switching unit 69 switches between the TDI method and the two-dimensional imaging method on the basis of the calculation results from the calculation unit 68, and output a switching signal to the detector 62.

The calculation unit 68 calculates the scanning time for the stage 30 in the TDI method and the two-dimensional imaging method. Then, by comparing the durations of the scanning times used in each method, it selects the method having the shorter scanning time.

In this way, the measurement carried out by the microscope imaging apparatus 310 is performed while scanning the plurality of sample located portions 22, that is, while scanning the cells in the two-dimensional patterned portion 23. Accordingly, when measuring the two-dimensional patterned portion 23 with the TDI method or the two-dimensional imaging method, the shorter time required for scanning, that is, the shorter measurement time, is employed. The specimen 20 used here has the configuration shown in FIGS. 5A and 5B.

The method of estimating the respective scanning times of the specimen 20 when the specimen 20 is imaged with the TDI method and the two-dimensional imaging method shall be described next.

First, the parameters used in estimating the scanning time of the specimen 20 will be described.

Figure 25A:
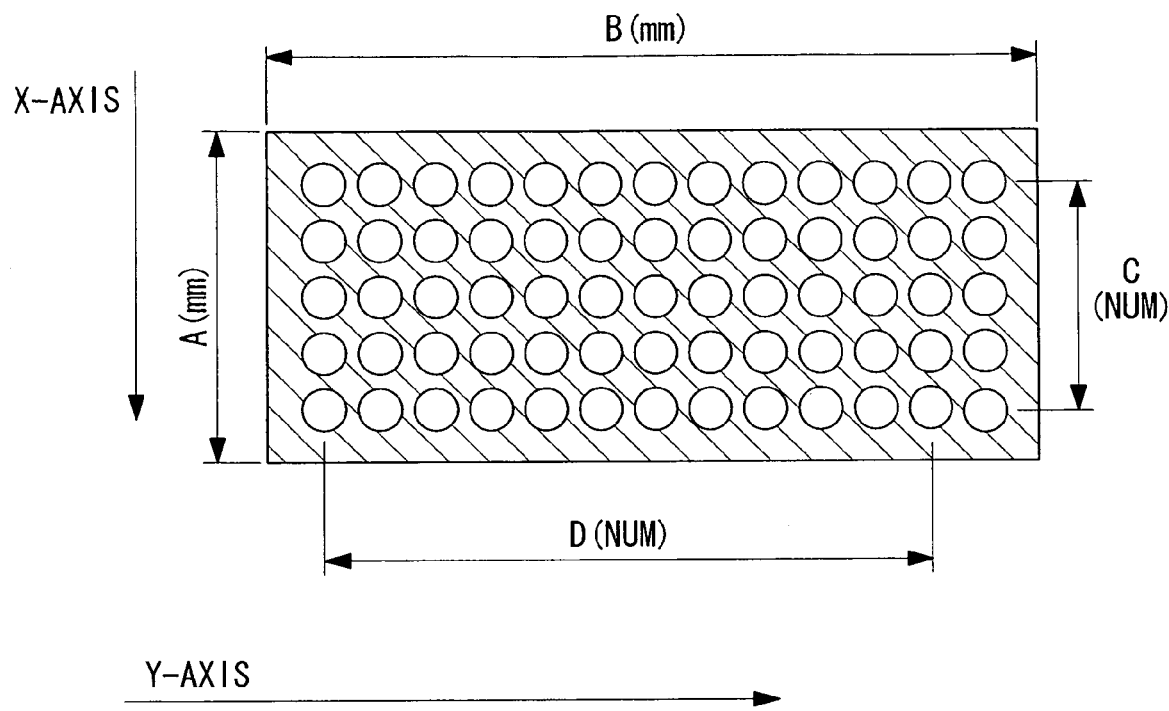
FIGS. 25A and 25B show parameters used in estimating the scanning time.
Figure 25B:
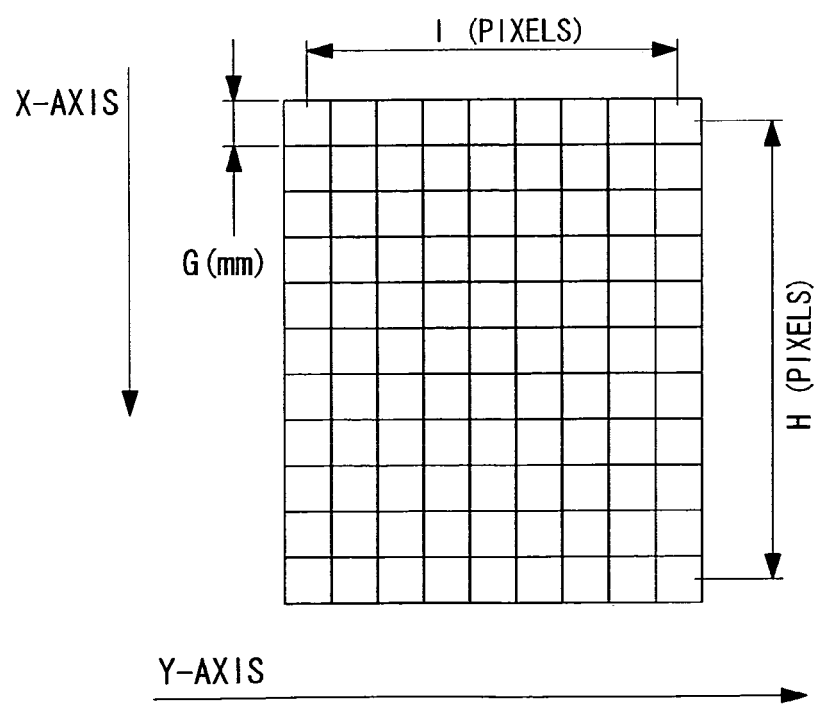

FIG. 25A shows the parameters for the specimen. FIG. 25B shows the parameters for the imaging device 63.

As shown in FIG. 25A, a measurement substrate 21 has a rectangular outer shape. The length in the X direction is A (mm), and the length in the Y direction is B (mm). Also, the sample located portions 22 are arranged in a C×D array, where C is the number in the X direction and D is the number in the Y direction. Therefore, the total number of sample located portions 22 is C×D.

The exposure time for each sample located portion is E (s), and the number of measurement wavelengths is F. For example, when observing two different fluorescence dyes (fluorescence wavelengths), the number of measurement wavelengths F is two.

As shown in FIG. 25B, the pixel pitch of the imaging device 63 is G (mm). The number of pixels disposed in the X direction is H (pixels), and the number of pixels disposed in the Y direction is I (pixels). Furthermore, the magnification of the objective lens is J1, and the projection magnification is J2.

When measuring the specimen 20 with the TDI method, as shown in FIG. 6, the entire surface of the two-dimensional patterned portion 23 is scanned regardless of whether or not the sample located portions 22 exist.

When measuring fluorescence with a plurality of wavelengths, the number of wavelengths that can be observed in one scan is only one. Therefore, the stage must be moved back and forth corresponding to the number of wavelengths. For example, when measuring fluorescence with two wavelengths, to acquire an image of one line, the stage 30 must be moved back and forth twice.

The calculation for estimating the measurement time in the TDI method is described below.

The product of the TDI line transfer rate and the number of pixels in the imaging device 63 in the transfer direction gives the exposure time. Therefore, the transfer rate (Tshift) is given by:

$T\text{shift}=E/I$ (seconds).

The stage speed (Vstage) can be expressed by the ratio of the pixel size on the examination surface to the transfer rate. Therefore, the stage speed is expressed by:

$V\text{stage}=(G/(J1\times J2))/T\text{shift}$ (mm/sec).

The time required for a one-way scan of the measurement substrate 21 (Tsingle) is given by:

$T\text{single}=B/V\text{stage}$ (seconds).

Detection is not performed when returning the stage 30, but it is assumed that the same time is required as for the one-way scan of the stage 30. In such a case, the time required for one reciprocation of the stage 30 (Tdouble) is expressed as:

$T\text{double}=2\times T\text{single}$ (seconds).

When measuring fluorescence with a plurality of wavelengths, the stage is reciprocated according to the number of wavelengths measured. Therefore, the time required to complete acquisition of one line (Tline) is expressed as:

$T\text{line}=F\times T\text{double}$ (seconds).

The number of scans (N) can be expressed as the ratio of the size of the measurement substrate 21 in the X direction to the size of the imaging device 63 in the X direction, on the surface of the object under examination. Therefore, the number of scans is given by:

$N=[A/(H\times G/J)]+1$ (repetitions)

where the square brackets indicate Gauss' symbol, that is, the greatest integer that is not over that value, for example, [2.34]=2.

Therefore, the scanning time in the TDI method (Ttdi) is:

$T\text{tdi}=C\times T\text{line}$ (seconds).

Instead of the imaging device 63 described above, an imaging device 63a having an electronic shutter may be used in this embodiment too. Using such an imaging device 63a is advantageous in that the exposure time can be reduced. The electronic shutter and the mechanical shutter are as described previously.

The timing chart of the electronic shutter in the TDI method is as shown in FIG. 9.

When determining the scanning time of the specimen 20, the maximum TDI transfer rate (t1) is Tshift.

Next, the method of estimating the measurement time in the two-dimensional imaging method will be described.

Figure 26:
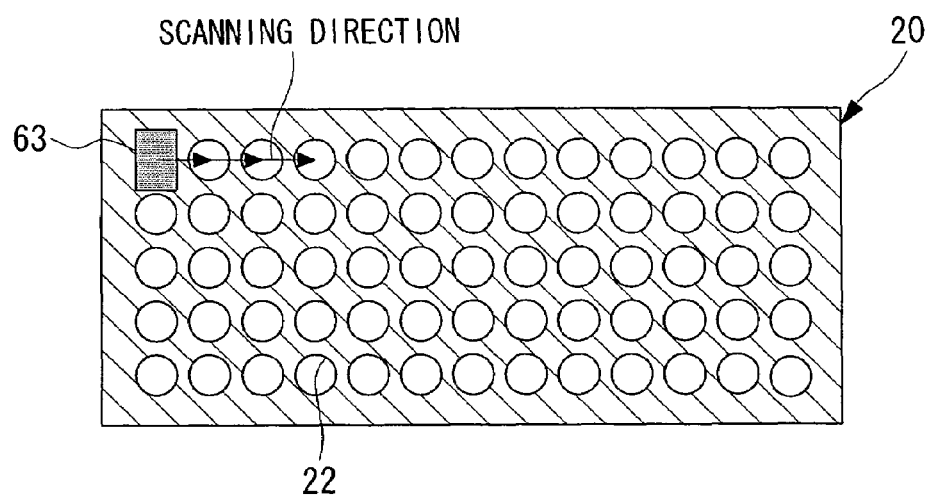
FIG. 26 depicts scanning in a two-dimensional imaging method.

FIG. 26 depicts scanning in the two-dimensional imaging method. In FIG. 26, for the sake of simplifying the illustration, the imaging device 63 is depicted as moving.

As shown in FIG. 26, when carrying out measurement of the specimen 20 with the two-dimensional imaging method, the stage 30 is moved while performing measurement. By moving the stage 30, the measurement point sequentially moves to the next sample located portion 22 in the examination region.

Figure 27:
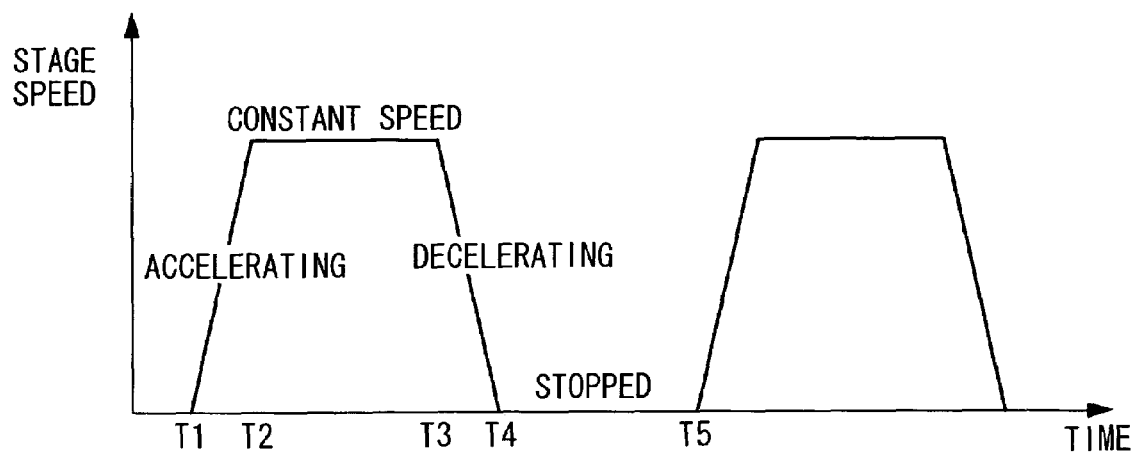
FIG. 27 depicts the operation of a stage in the two-dimensional imaging method.

FIG. 27 is a graph depicting the operation of the stage 30 in the two-dimensional imaging method.

As shown in FIG. 27, the stage 30 is driven while alternating between acceleration and deceleration. The motion of the sample located portions 22 advances in this way. The stage 30 accelerates during the period T1 to T2, moves at constant speed during period T2 to T3, decelerates during period T3 to T4, and stops during period T4 to T5.

Thus, measurement of the sample located portion 22 is carried out during period T4 to T5 where the stage 30 stops.

In the two-dimensional imaging method, charge transfer in the imaging device 63 does not occur, unlike the TDI method. Therefore, in the two-dimensional imaging method, image acquisition can be carried out regardless of the direction of motion of the stage 30.

Next, the method of estimating the measurement time in the two-dimensional imaging method will be described.

Here, the time to move between the sample located portion 22 is K (seconds). In addition, when measuring a plurality of wavelengths, the dichroic mirror in the microscope is changed. Therefore, the time required to change the dichroic mirror is L (seconds). In the microscope, the dichroic mirrors are normally held in a turret, which is rotated by a driving mechanism such as a motor or the like. Thus, changing of the dichroic mirror is carried out electrically.

The measurement time Tmeasure for one sample located portion 22 depends on the exposure time E (seconds), the time for changing the dichroic mirror L (seconds), and the number of measurement wavelengths F, and is given by:

$T\text{measure}=F\times E+(F-1)\times L$ (seconds).

Considering the period for moving between the sample located portions 22, the measurement interval Twell between one sample located portion 22 and another sample located portion 22 is given by:

$T\text{well}=T\text{measure}+K$ (seconds).

Also, because the sample located portions 22 are arranged in a C×D matrix, the scanning time for the two-dimensional imaging method (T2D) is:

$T2D=C\times D\times T\text{well}$ (seconds).

Next, an example of an actual estimation is shown in Tables 1 to 3.

Table 1 shows values of parameters used in the estimation. The values of parameters C, D, E, and F in Table 1 are shown in Table 2. Table 2 shows the estimated results of the measurement time corresponding to the parameters C, D, E, and F. Tables 3 and 4 show intermediate results of the estimation for each parameter.

TABLE 1

| Measurement substrate | | No. wells | | Exposure time | No. measurement wavelengths | Pixel size | No. pixels | | Magnification | | Switching time for two-dimensional imaging method | |
|---|---|---|---|---|---|---|---|---|---|---|---|---|
| | | | | | | | X | Y | Objective lens | Projection lens | Moving | Switching |
| X (mm) A | Y (mm) B | X (no.) C | Y (no.) D | (s) E | Wavelength F | (mm) G | pixels H | pixels I | (magnification) J1 | (magnification) J2 | time (s) K | time (s) L |
| 26 | 76 | | | parameters | | 0.0065 | 1300 | 1000 | 20 | 0.5 | 4 | 1 |

TABLE 2

| Measurement conditions | | | Measurement time (excluding image transfer time) | | |
|---|---|---|---|---|---|
| No. sample located portions C*D (no.) | Exposure time E (s) | No. wavelengths F | TDI method Ttdi (s) | Two-dimensional imaging method T2D (s) | Method used |
| 1000 | 0.1 | 1 | 725 | 4100 | TDI method |
| 100 | 0.1 | 1 | 725 | 410 | Two-dimensional imaging method |
| 1000 | 0.1 | 2 | 1450 | 5200 | TDI method |
| 100 | 0.1 | 2 | 1450 | 520 | Two-dimensional imaging method |

TABLE 3

| | 1 | 2 | 3 | 4 |
|---|---|---|---|---|
| Tshift (s) | 1.00E−04 | 1.00E−04 | 1.00E−04 | 1.00E−04 |
| Vstage (s) | 6.5 | 6.5 | 6.5 | 6.5 |
| Tstage (s) | 11.7 | 11.7 | 11.7 | 11.7 |
| Tdouble (s) | 23.4 | 23.4 | 23.4 | 23.4 |
| Tline (s) | 23.4 | 23.4 | 46.8 | 46.8 |
| N (repetitions) | 31 | 31 | 31 | 31 |
| Ttdi (s) | 725 | 725 | 1450 | 1450 |

TABLE 4

| | 5 | 6 | 7 | 8 |
|---|---|---|---|---|
| Tmeasure (s) | 0.1 | 0.1 | 1.2 | 1.2 |
| Twell (s) | 4.1 | 4.1 | 5.2 | 5.2 |
| T2D (s) | 4100 | 410 | 5200 | 520 |

Figure 28:
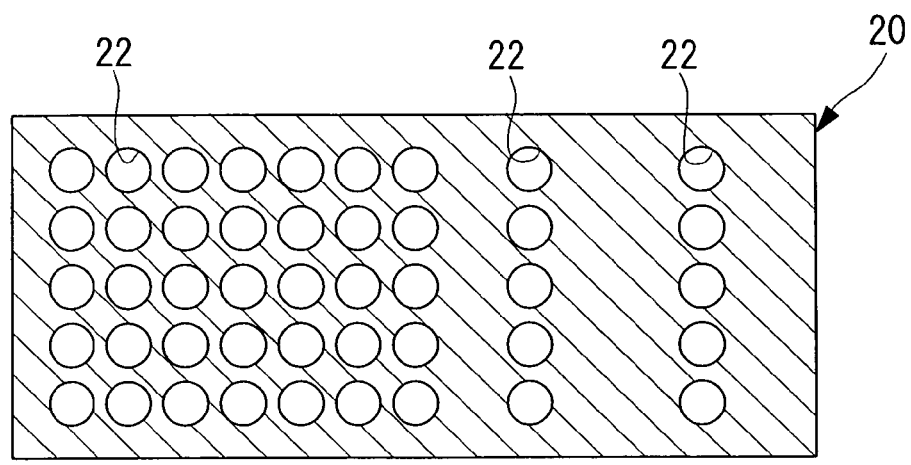
FIG. 28 shows a specimen in which the density of sample located portions is asymmetric.
Figure 29:
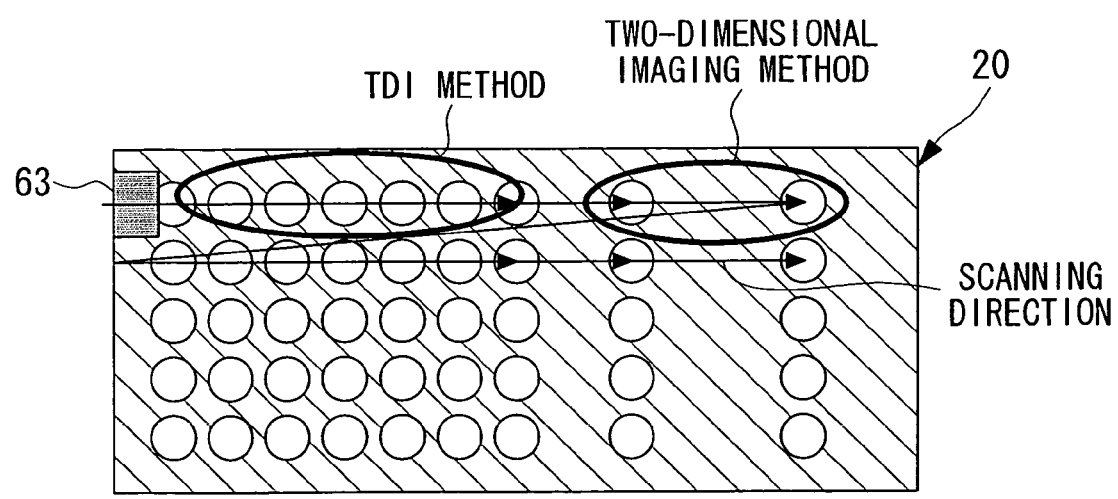
FIG. 29 depicts an example in which scanning is switched between the TDI method and the two-dimensional imaging method.

FIG. 28 shows an arrangement in which the density of sample located portions 22 on the measurement substrate 21 changes depending on position (that is, the density is non-uniform). FIG. 29 depicts an example where the scanning method switches between the TDI method and the two-dimensional imaging method.

As shown in FIG. 28, when the density of the sample located portions 22 is non-uniform, two imaging methods are used. Specifically, as shown in FIG. 29, the region where the density of specimen location portions 22 is high (the region at the left in FIGS. 28 and 29) is measured with the TDI method, and the region where the density is low (the region at the right in FIGS. 28 and 29) is measured with the two-dimensional imaging method. In this way, by switching between the TDI method and the two-dimensional imaging method depending on the distribution of sample located portions 22, it is possible to select the method having the higher scanning speed for carrying out measurement. As a result, the measurement time can be shortened.

In the measurement described above, measurement of the specimen 20 is carried out right after the measurement preparation has been completed. However, a prescan may be carried out to measure the density of sample located portions 22 in the specimen 20 before measuring the specimen 20. Doing so allows the main measurement to be carried out after selecting the TDI method or the two-dimensional imaging method for measuring the specimen 20 on the basis of information about the density obtained in the prescan.

When performing the prescan, it is preferable that the objective lens 49 have low magnification. By doing so, the field of view of the microscope is widened, and therefore, it is possible to complete the prescan in a shorter period of time. Also, user input is not required beforehand.

Furthermore, when the density of sample located portions 22 is non-uniform, as shown in FIG. 28, it requires a substantial effort for the user to input information for changing the imaging method. Conversely, since the imaging method can be changed automatically on the basis of the prescan, no such effort is required.

With the configuration described above, the method having the shorter scanning time among the TDI method and the two-dimensional imaging method is selected as the method used in the measurement. Therefore, compared to the case where the method is not selected, the scanning in the measurement can be carried out more quickly. Also, being able to select the method having the higher scanning speed allows the time required for measuring the specimen 20 to be reduced.

Moreover, it is possible to automatically select either the TDI method or the two-dimensional imaging method, whichever is most appropriate, on the basis of the number of measurement wavelengths, the exposure time, and the density of the specimen 20. Therefore, it is easy to speed up the scanning procedure, which allows the measurement time to be easily reduced.

With the microscope imaging apparatus of this embodiment, the method for measuring the object under examination can be selected from either the TDI method or the two-dimensional imaging method on the basis of the scanning time described above, and it is therefore possible to select the method having the shorter scanning time.

Accordingly, compared to a case where the imaging method is not selected, the scanning during measurement of the object under examination can be made faster, and the time required for measurement can thus be reduced.

Tenth Embodiment

Next, a tenth embodiment will be described with reference to FIGS. 30 to 45. The tenth embodiment is a biological-specimen examination system using one of the microscope imaging apparatuses according to the first to ninth embodiments described above.

Figure 30:
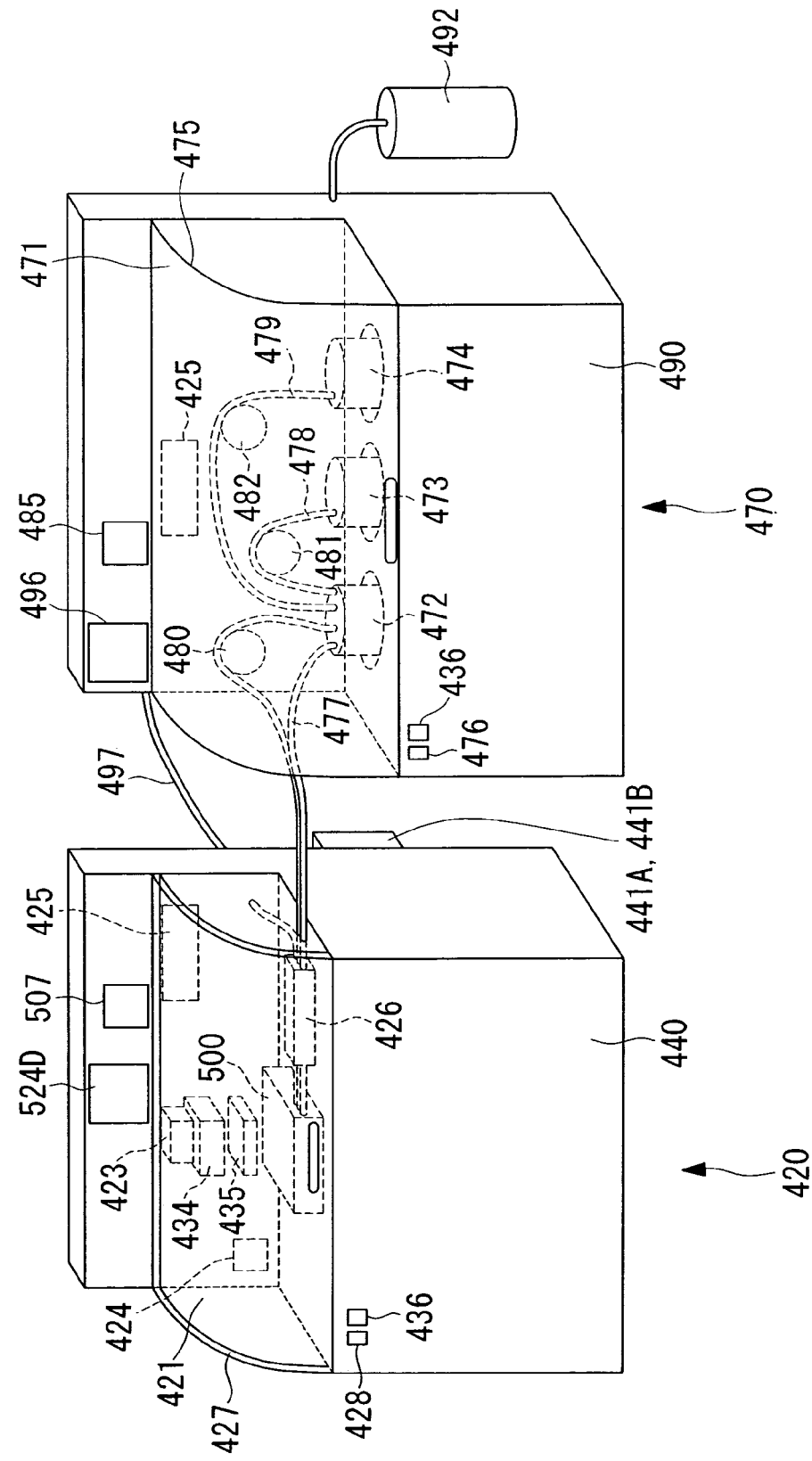
FIG. 30 is a perspective view showing a biological-specimen examination system according to a tenth embodiment of the present invention, which is provided with a microscope imaging apparatus.
Figure 31:
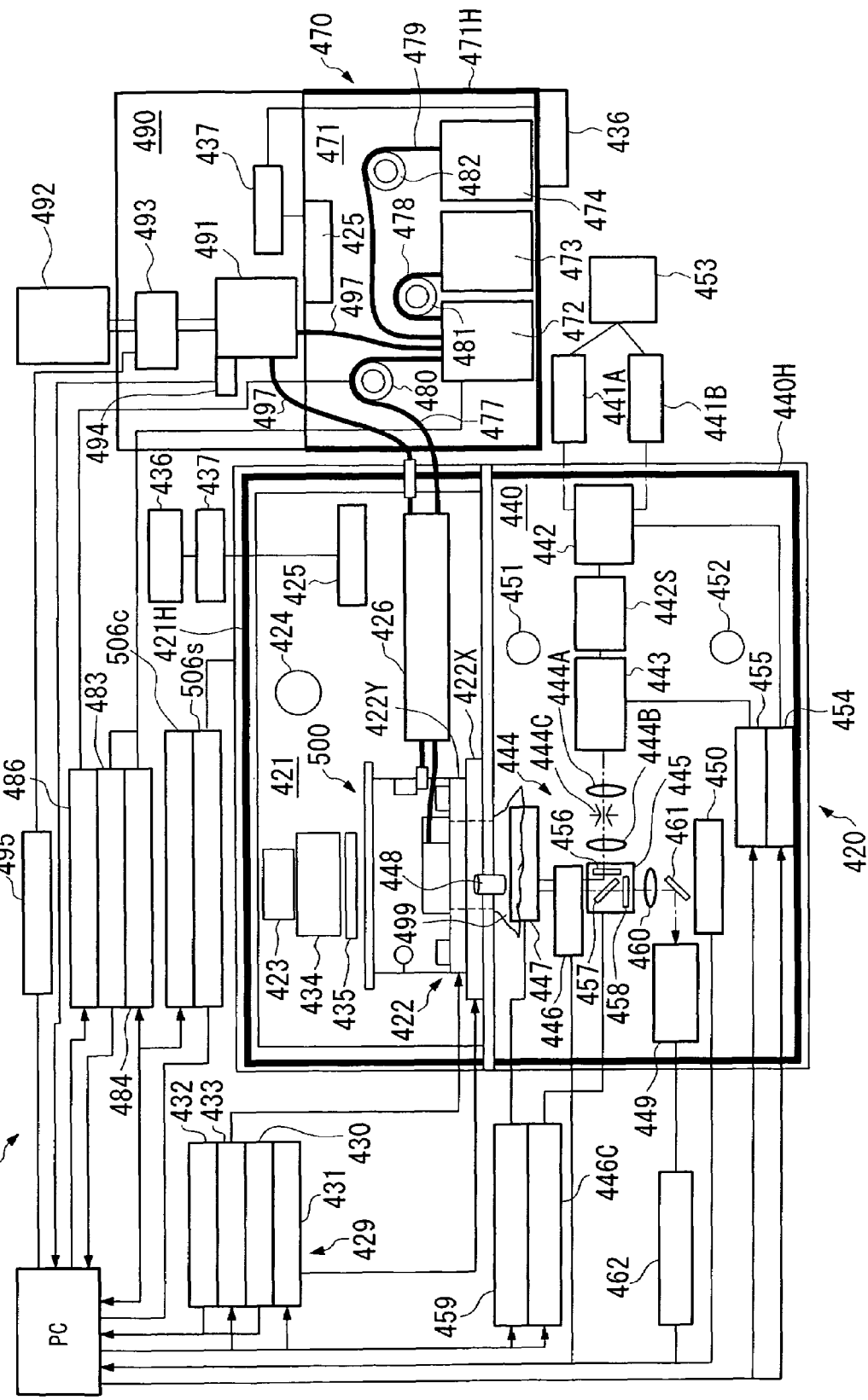
FIG. 31 is a schematic diagram showing the system configuration of the biological-specimen examination system shown in FIG. 30.

FIG. 30 is a perspective view showing an overview of a biological-specimen examination system 410 according to this embodiment. FIG. 31 is a schematic diagram showing the system configuration of the biological-specimen examination system.

As shown in FIGS. 30 and 31, the biological-specimen examination system 410 includes a detection unit 420 and a culture unit 470. The detection unit 420 and the culture unit 470 are preferably disposed adjacent to each other, and more preferably, the units 420 and 470 are disposed in contact with each other.

As shown in FIGS. 30 and 31, the detection unit 420 includes an insulated compartment 421 that contains biological specimens and a detection section (microscope imaging apparatus) 440 that measures cells CE serving as the biological specimens.

The insulated compartment 421 includes a heater 421H for keeping the interior of the insulated compartment 421 at a predetermined temperature; a stage 422 that holds an incubator box 500 (described later); a transmission light source (illuminating unit) 423 that irradiates the cells CE with light; a fan 424 to make the temperature inside the insulated compartment 421 uniform; a UV lamp 425 for sterilizing the interior of the insulated compartment 421; a carrier 426 that covers a culture-fluid circulating tube 477 (described later), a culture-gas supply tube 497, and so on; a door 427 used when putting the incubator box 500 or the like in the insulated compartment 421 or when removing it therefrom; and a main power-supply switch 428 for turning on and off the main power supply of the detection unit 420.

The stage 422 includes an X-axis motion stage 422X and a Y-axis motion stage 422Y that move relative to each other in mutually orthogonal directions, and scanning of the stage 422 is controlled by a stage scanning unit (motion unit) 429.

The stage scanning unit 429 is formed of an X-axis coordinate detection unit 430 that detects the X-axis coordinate value of the X-axis motion stage 422X, an X-axis scanning controller 431 that controls the motion (scanning) of the X-axis motion stage 422X, a Y-axis coordinate detection unit 432 that detects the Y-axis coordinate value of the Y-axis motion stage 422Y, and a Y-axis scanning controller 433 that controls the motion (scanning) of the Y-axis motion stage 422Y.

The X-axis coordinate detection unit 430 and the Y-axis coordinate detection unit 432 are configured so as to output the detected X-coordinate of the X-axis motion stage 422X and the Y-coordinate of the Y-axis motion stage 422Y, respectively, to a computer PC. The X-axis scanning controller 431 and the Y-axis scanning controller 433 are configured so as to control the scanning of the X-axis motion stage 422X and the scanning of the Y-axis motion stage 422Y on the basis of respective instructions from the computer PC.

The mechanism for driving the X-axis motion stage 422X and the Y-axis motion stage 422Y may be, for example, a combination of a motor and a ball screw.

As described above, the computer PC controls the scanning of the X-axis motion stage 422X and the Y-axis motion stage 422Y, and in addition, as described later, it also controls the detection system of the cells CE, performs analysis of the images of the cells CE, and so on and controls the X-axis motion stage 422X, the Y-axis motion stage 422Y, the detection system, and the analysis system in a coordinated fashion.

A condenser lens 434 that focuses the light emitted from the transmission light source 423 onto the cells CE is disposed between the transmission light source 423 and the incubator box 500.

A shutter 435 may be disposed between the condenser lens 434 and the incubator box 500, or the shutter 435 may be omitted.

The fan 424 is disposed on the wall of the insulated compartment 421. Operating this fan 424 causes air convection inside the insulated compartment 421, which enables the temperature inside the insulated compartment 421 to be easily kept uniform and constant.

The UV lamp 425 is connected to a UV-lamp switch 436 disposed on the wall of the detection unit 420, and a control timer 437 that periodically operates the UV lamp 425 is disposed between the UV lamp 425 and the UV-lamp switch 436. Furthermore, a sterilization-in-progress indicator lamp (not shown) for indicating that the UV lamp 425 is turned on is provided.

For example, if the UV-lamp switch 436 is pressed when not measuring the cells CE, the timer 437 commences counting and power is supplied to the UV lamp 425 to irradiate the interior of the insulated compartment 421 with UV light (ultraviolet light). At the same time, the sterilization-in-progress indicator lamp is illuminated. Then, after a predetermined amount of time (for example, 30 minutes), the timer 437 finishes counting, the timer 437 stops supplying power to the UV lamp 425, and the UV irradiation is stopped. Also, the sterilization-in-progress lamp is turned off.

The UV lamp 425 can be controlled independently of the main power-supply switch 428 so that it can be operated even if the main power-supply is off.

The illumination time of the UV lamp 425 may be 30 minutes, as described above. Alternatively, an illumination time less than 30 minutes or more than 30 minutes may also be used so long as contamination and so forth inside the insulated compartment 421 can be completely killed.

The door 427 is formed of a metal such as aluminum or the like that has been subjected to anodizing, or it may be formed of a translucent resin with high opacity.

The door 427 may have a double-layer construction with an air gap, or the inside may be formed of metal and the outside formed of resin. Using resin on the outside of the door 427 can prevent heat from inside the insulated compartment 421 from escaping through the door 427. Also, forming the inside of the door 427 of anodized metal can prevent deterioration of the lifetime of the door 427 due to the UV lamp 425.

If the door 427 has a double-layer construction of metal or metal and resin, since light is completely blocked, it is preferable to provide an inspection window at a position where the incubator box 500 can be viewed. The inspection window is preferably formed of transparent resin or glass, and an openable/closable cover is preferably disposed at the outer side thereof.

As shown in FIGS. 16 and 17, a detection section 440 includes a heater 440H for keeping the interior of the detection section 440 at a predetermined temperature; incident light sources 441A and 441B that irradiate the cells CE from the detection section 440 side; a light-path switching unit 442 that switches the light path from the incident light sources 441A and 441B; a light-intensity adjusting mechanism 443 that adjusts the intensity of the irradiated light; a lens system 444 that focuses the irradiated light towards the cells CE; a filter unit 445 that controls the wavelength of the irradiated light and the wavelength of the detection light; an autofocus (AF) unit 446 that performs a focusing operation with respect to the cells CE; a revolver 447 provided with a plurality of objective lenses 448 having different magnifications and properties; a detector (imaging unit) 449 that detects detection light from the cells CE; a light-intensity monitor 450 that measures the intensity of the detection light; a fan 451 that makes the temperature inside the detection section 440 uniform; and a cooling fan 452 that cools the interior of the detection section 440.

The incident light sources (illumination unit) 441A and 441B, which are formed of mercury lamps, for example, are disposed outside the detection section 440 and are connected to a power supply 453 that supplies power thereto.

Normally, a single incident light source, for example, the incident light source 441A, is used; however, if the intensity of the incident light source 441A falls below a certain prescribed value, light is irradiated from the other incident light source 441B and the power supply to the first incident light source 441A is turned off.

The light-path switching unit 442 is configured to guide illumination light from either the incident light source 441A or the incident light source 441B to the light-intensity adjusting mechanism 443. Also, the light-path switching unit 442 is provided with a light-path control unit 454, which is connected to the computer PC (described later) for controlling the light-path switching unit 442 on the basis of an instruction from the computer PC.

At the emitting side of the light-path switching unit 442 where the illumination light is emitted, a shutter 442S that controls the transmission and blocking of the illumination light is provided.

The light-intensity adjusting mechanism 443, which is disposed at the emission side of the shutter 442S where the illumination light is emitted, adjusts the intensity of the illumination light passing through the shutter 442S. A known aperture mechanism, for example, may be used, or any other known mechanism or technique that can adjust the light intensity may be used.

The light-intensity adjusting mechanism 443 is provided with a light-intensity control unit 455, which is connected to the computer PC (described later) for controlling the light-intensity adjusting mechanism 443 on the basis of an instruction from the computer PC.

The lens system 444 is disposed at the emission side of the light-intensity adjusting-mechanism 443 where the illumination light is emitted. The lens system 444 includes a pair of lenses 444A and 444B and a stop 444C disposed between the lens 444A and the lens 444B.

The filter unit 445 includes an excitation filter 456, a dichroic mirror 457, and an absorption filter 458. The excitation filter 456 is a filter that transmits wavelengths which contribute to the generation of fluorescence in the cells CE (excitation light) from among the illumination light and is disposed so that the illumination light emitted from the lens system 444 is incident on the excitation filter 456. The dichroic mirror 457 is an optical element that splits excitation light and fluorescence. More specifically, the dichroic mirror 457 is disposed so as to reflect excitation light transmitted through the excitation filter 456 towards the cells CE and to transmit fluorescence from the cells CE. The absorption filter 458 is an optical element that separates fluorescence from the cells CE from other unwanted scattered light. The absorption filter 458 is disposed so that light transmitted through the dichroic mirror 457 is incident thereon.

The filter unit 445 is provided with a filter control unit 446C that controls the wavelengths of the excitation light emitted from the filter unit 445 and the detection light (fluorescence) on the basis of instructions from the computer PC (described later).

One excitation filter 456, one dichroic mirror 457, and one absorption filter 458 may be used, or alternatively, a plurality of each may be used.

The AF unit 446 is disposed at the emission side of the filter unit 445 where the excitation light is emitted and is disposed so that the excitation light is focused onto the cells CE via one of the objective lenses 448, on the basis of an instruction from the computer PC (described later).

The revolver 447 is disposed at the emission side of the AF unit 446 where the excitation light is emitted and is provided with the plurality of objective lenses 448 having different magnifications. The revolver 447 is provided with an objective-lens control unit 459 which selects and controls the objective lens 448 on which the excitation light is incident, on the basis of an instruction from the computer PC (described later).

The objective lenses 448 are configured to allow examination, from the detection section 440, of the interior of the incubator box inside the insulated compartment 421 via holes provided in the X-axis motion stage 422X and the Y-axis motion stage 422Y.

The holes in the X-axis motion stage 422X and the Y-axis motion stage 422Y are large enough to allow viewing over the operating region of the stage, with some additional margin.

Therefore, although the ambient air inside the insulated compartment 421 should be kept at a humidity suitable for culturing cells, the ambient air may escape to the detection section 440 through the holes, which makes it impossible to maintain the temperature suitable for culturing cells, and therefore, there is a risk of bringing about a reduction in cell activity.

Thus, a containment mechanism 449 for suppressing the passage of such ambient air, which is at a temperature suitable for cell culturing, between the insulated compartment 421 and the detection section 440.

The containment mechanism 449 should be capable of suppressing the flow of air while not interfering with the operation of the revolver 447 and the objective lenses 448. For example, it may be a sheet-like mechanism in which, for example, a sheet formed of a flexible material, such as a film or transparent sheet, is attached to the perimeter of a hole provided at the boundary between the insulated compartment 421 and the detection section 440 and in such a manner that it is draped around the perimeter of the revolver.

A focusing lens 460 that focuses the detection light onto the detector 449 and the light-intensity monitor 450 is provided at the emission side of the filter unit 445 where the detection light is emitted.

A half-mirror 461 that reflects some of the detection light towards the detector 449 and that transmits the remaining detection light towards the light-intensity monitor 450 is provided at the emission side of the focusing lens 460 where the detection light is emitted.

The detector 449 is disposed at a position where the detection light reflected from the half mirror 461 is incident thereon. Also, a detector calculation unit 462 that calculates a detection signal from the detector 449 and outputs it to the computer PC (described later) is connected to the detector 449.

The detector 449 is not particularly limited and may use a line sensor, an area sensor, or both a line sensor and an area sensor.

The light-intensity monitor 450 measures the detection light transmitted through the half-mirror 461 and is configured so as to output the measured value to the computer PC.

The intensity of the detection light may be measured using the light-intensity monitor 450, as described above, or alternatively, the intensity of the detection light may be measured using an illuminance meter or a power meter.

The heater 440H controls the temperature inside the detection section 440 to be from 30° C. to 37° C. The fan 451 is disposed to cause air convection inside the detection section 440 to make the temperature inside the detection section 440 uniform. Therefore, the temperature inside the detection section 440 can be maintained close to the temperature in the insulated compartment 421, and the temperature in the insulated compartment 421 can thus be more easily stabilized.

The cooling fan 452 is operated to reduce the temperature inside the detection section 440 on the basis of the output from a temperature sensor (not shown) provided inside the detection section 440. Therefore, it is possible to prevent an abnormal rise in temperature inside the detection section 440 due to heating by, for example, the motors and so forth.

FIG. 32 is a perspective view of the incubator box according to this embodiment, and FIG. 33 is a cross-sectional view of a chamber according to this embodiment.

As shown in FIGS. 32 and 33, the incubator box 500 includes a frame 501, containing a chamber (object under examination) 510, and a cover 502 that forms a sealed space together with the frame 501. The frame 501 and the cover 502 are subjected to magnetic-shielding treatment for blocking external magnetic fields and anti-static treatment for eliminating the build-up of static electricity in the incubator box 500.

The frame 501 is formed of a base plate 503 and side walls 504, and a region corresponding to the measurement area of the base plate 503 is formed of a transparent material, such as glass. The other regions of the base plate 503 and the side walls 504 are preferably formed of an anti-corrosive material having high opacity, such as anodized aluminum or stainless steel, like SUS316. More preferably, from the viewpoint of maintaining the temperature, a material having a low thermal conductivity may be selected.

An adaptor 505 for holding the chamber 510 and a temperature sensor 506 for measuring the temperature of the chamber 510 are provided on the base plate 503. The chamber 510 may be held using the adaptor 505, as described above, or the chamber 510 may be held without using the adaptor 505.

The output from the temperature sensor 506 is input to the computer PC via an incubator-temperature detection unit 506S and is also input to a temperature-display unit 507 disposed on the wall of the detection unit 420. The computer PC controls the heater 421H and so on via an incubator-temperature control unit 506C shown in FIG. 17 to control the temperature inside the incubator box 500 in order to keep it constant.

The cover 502 includes a glass plate 517 that transmits the illumination light and a support portion 517A that supports the glass plate 517. An anti-reflection film may be formed on both sides of the glass plate 517 in a region corresponding to the measurement area. Forming such an anti-reflection film on both sides allows prevention of reflection by the glass plate 517 during transmission examination and incidence examination.

The area of the glass plate 517 may be substantially the same as that of the base plate 503 of the incubator box 500, or it may be the minimum necessary area that does not cause any problem during measurement.

As shown in FIG. 33, the chamber 510 is formed of a lower glass member 511 for observation with the objective lens 448, an upper glass member 512 for transmitting light from the transmission light source 423, and a frame member 513 that supports the lower glass member 511 and the upper glass member 512.

Joints 514 having channels formed therein for circulating culture fluid are formed at opposing sides of the frame member 513. A culture-fluid circulating tube 477 (described later) is connected to the joints 514, for allowing culture fluid to circulate between the culture unit 470 and the detection unit 420.

A pair of flow smoothers 515 for making the flow of culture fluid uniform are disposed in the frame member 513 so as to be substantially orthogonal to the flow of culture fluid. The flow smoothers 515 are formed of sheet members in which, for example, small holes are formed in a matrix, and by splitting the culture fluid and flowing it through the plurality of small holes, the flow becomes uniform. A slide glass 516 on which the cells CE are disposed is provided between the two flow smoothers 515.

Figure 34A:
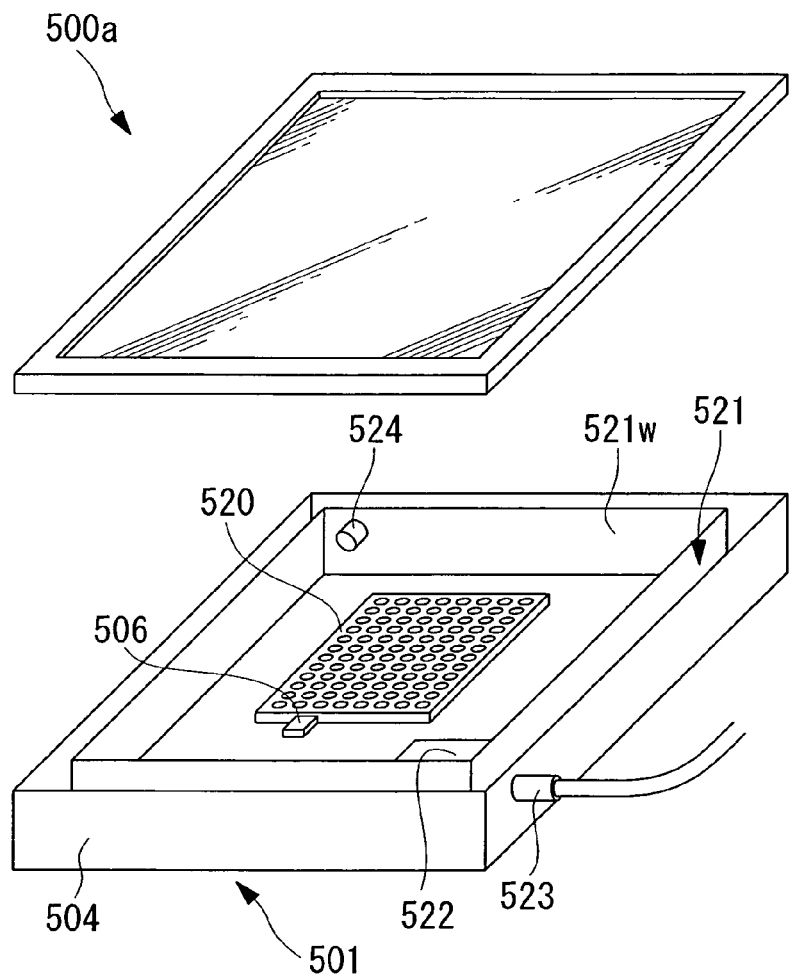
FIGS. 34A and 34B are perspective views showing other examples of the incubator box shown in FIG. 33.

As described above, the incubator box 500 may be provided with the chamber 510 inside, or, as shown in FIG. 34A, a microplate (object under examination) 520 (or a well plate) may be disposed inside.

In this configuration, as shown in FIG. 34A, the frame 501 of an incubator box 500a is provided with a square-shaped reservoir 521 surrounding the microplate 520, an internal fan 522 disposed at the inner side of the reservoir 521, a connector 523 for supplying culture gas, and a culture-gas concentration sensor 524 for detecting the concentration of carbon dioxide in the culture gas.

The temperature sensor 506 is disposed so as to measure the temperature of the microplate 520. The microplate temperature input to the computer PC from the temperature sensor 506 is collected in the form of text data in a memory and can be subjected to data processing in the computer PC.

The culture-gas concentration sensor 524 outputs the carbon-dioxide concentration to the computer PC and to a culture-gas concentration display unit 524D.

The height of side walls 521W of the reservoir 521 is formed to be lower than the height of the side walls of the frame 501. Also, the positional relationship with respect to the connector 523 is adjusted so that the supplied culture gas blows against the side walls 521W. Sterilized water is stored in the reservoir 521, and the humidity inside the incubator box 500a is regulated at about 100%.

The internal fan 522 is disposed so that the microplate 520 is not positioned in the blowing direction thereof and so that it blows along the side walls 521W of the reservoir 521.

The culture-gas concentration sensor 524 may be disposed on the inner surface of one of the side walls 521W of the reservoir 521. Alternatively, the tubes from the incubator box 500a' may be disposed outside and the culture gas inside the incubator box 500a may be evacuated with a suction pump to detect the concentration thereof with the culture-gas concentration sensor 524.

When using this kind of incubator box 500a, the destination of the culture gas supplied from a culture-gas mixing tank 491 (described later) is changed from a culture fluid vessel 472 to the incubator box 500a, and because it is not necessary to supply culture fluid from the culture unit 470, the operation of a culture-fluid pump 480 or the like can be stopped.

With such a construction, since the humidity environment and culture-gas concentration in the incubator box 500a are maintained so that little damage is caused to the cells CE by changes and non-uniformity in the humidity and culture-gas concentration, damage to the cells CE can be reduced compared to a thermal environment.

Also, because the humidity and culture-gas concentration in the incubator box 500a, which is not directly in contact with the detection section 440, are maintained, it is possible to prevent contamination during examination.

Furthermore, since it is not necessary to maintain the proper humidity and culture-gas concentration when culturing the cells CE in the insulated compartment 421, the performance of the objective lenses 448 and so on disposed in the insulated compartment 421 can be prevented from deteriorating. Thus, a reduction in lifetime of the objective lenses 448 and so on can be prevented.

The chamber 510 may be a sealed enclosure, as described above, or it may be an open chamber that is not sealed. Such an open chamber is formed with the same construction as the chamber 510 except for the provision of the upper glass member 512.

When using such an open chamber, using the incubator box 500 described above, the incubator box 500a is filled with the culture gas and the open chamber is supplied with culture liquid.

Figure 34B:
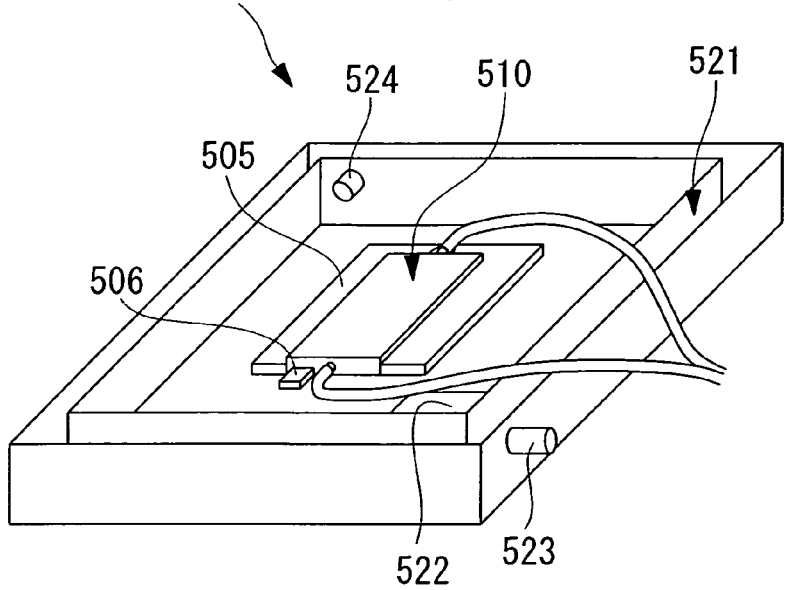

As shown in FIG. 34B, the chamber 510 described above may also be used in the incubator box 500a. In such a case, the connector 523 for supplying culture gas is blocked off, and the culture-gas concentration sensor 524 is not used. If the size of the chamber 510 is different from that of the microplate 520, the chamber 510 may be placed in the incubator box 500a using an adaptor 505. Sterilized water need not be placed in the reservoir 521; in fact, the reservoir 521 itself may be eliminated from the incubator box 500a. Also, the temperature sensor 506 measures the temperature in the chamber 510.

The connector 523 may be blocked off, as described above, or it may be left connected to the culture-gas supply tube 497 and the supply of culture gas to the incubator box 500a simply stopped.

As shown in FIGS. 16 and 17, the culture unit 470 includes a sterilized compartment 471 containing the culture fluid and a mixing section 490 for producing the culture gas.

The sterile compartment 471 includes a heater 471H for keeping the interior of the sterile compartment 471 at a predetermined temperature; a culture-fluid vessel 472 for storing the culture fluid; an auxiliary tank 473 for storing spare culture fluid; a waste tank 474 into which used culture fluid is discharged; a UV lamp 425 for sterilizing the interior of the sterile compartment 471; a door 475 used when putting the culture-liquid vessel 472 into the sterile compartment 471 and when removing it therefrom; and a main power-supply switch 476 for turning on and off the main power supply for the culture unit 470.

The culture-fluid vessel 472 is provided with a culture-fluid circulating tube 477 for circulating culture fluid between the culture-fluid vessel 472 and the incubator box 500; a supply tube 478 for supplying spare culture fluid from the auxiliary tank 473; and a waste tube 479 for discharging used culture fluid from the culture-fluid vessel 472 to the waste tank 474.

A culture-fluid pump 480 for delivering culture fluid from the culture-fluid vessel 472 to the incubator box 500 and circulating the culture fluid is provided for the culture-fluid circulating tube 477. Using the culture-fluid pump 480, it is possible to replace the culture fluid in the chamber 510 with fresh culture fluid, and therefore, the cells CE can be cultured for a longer period of time compared to a case where the culture fluid is not replaced.

A supply pump 481 for transferring culture fluid from the auxiliary tank 473 to the culture-fluid vessel 472 is provided for the supply tube 478. In addition, a waste pump 482 for transferring the used culture fluid from the culture-fluid vessel 472 to the waste tank 474 is provided for the waste tube 479.

As described above, the waste tank 474 for storing the used culture fluid may be used. Alternatively, instead of using the waste tank 474, a discharge port for directly discharging the used culture fluid may be provided.

A culture-fluid temperature sensor (not shown) for detecting the culture-fluid temperature is provided in the culture-fluid vessel 472, and the output from the culture-fluid temperature sensor is input to the computer PC via a culture-fluid temperature detector 483. Data concerning the culture-fluid temperature input to the computer PC is collected in a memory in the form of text data and is used when comparing and verifying the detection results of the cells CE.

The heater 471H is provided with a culture-fluid temperature controller 484 that controls the temperature of the culture fluid via the temperature inside the sterilized compartment 471, on the basis of an instruction from the computer PC. The temperature of the culture fluid supplied from the culture-fluid vessel 472 is held at about 37° C. by the culture-fluid temperature controller 484, which prevents the activity of the cells CE from dropping due to temperature changes of the culture fluid. Also, a temperature display unit 485 for displaying the culture-fluid temperature detected by the culture-fluid temperature sensor is provided on the wall of the culture unit 470.

The culture-fluid pump 480 is provided with a culture-fluid-pump controller 486 for controlling the circulation of the culture fluid on the basis of an instruction from the computer PC. The operation of the supply pump 481 and the waste pump 482 is also controlled on the basis of instructions from the computer PC.

The UV lamp 425 is connected to a UV-lamp switch 436 disposed on the wall of the culture unit 470, and a timer 437 for periodically controlling the operation of the UV lamp 425 is provided between the UV lamp 425 and the UV-lamp switch 436. Furthermore, a sterilization-in-progress indicator lamp (not shown) for indicating that the UV lamp 425 is illuminated is also provided.

The UV lamp 425 is controlled independently of the main power-supply switch 476 and can be operated even when the main power-supply switch 476 is off.

As shown in FIGS. 16 and 17, the mixing section 490 includes a heater (not shown) for keeping the interior of the mixing section 490 at a predetermined temperature; a culture-gas mixing tank 491 for adjusting the carbon-dioxide concentration in the culture gas supplied to the incubator box 500; and a $CO_2$-pump 493 for supplying carbon dioxide from a $CO_2$ tank 492 provided outside the culture unit 470 to the culture-gas mixing tank 491.

A $CO_2$-concentration detector 494 is provided in the culture-gas mixing tank 491 for detecting the concentration of carbon dioxide therein, and the output from the $CO_2$-concentration detector 494 is input to the computer PC. The $CO_2$ pump 493 is provided with a $CO_2$-concentration controller 495 for controlling the amount of carbon dioxide supplied to the culture-gas mixing tank 491 on the basis of an instruction from the computer PC. Also, a $CO_2$-concentration display unit 496 for displaying the carbon-dioxide concentration inside the culture-gas mixing tank 491, which is detected by the $CO_2$-concentration detector 494, is provided on the wall of the culture unit 470.

Furthermore, a culture-gas supply tube 497 is provided between the culture-gas mixing tank 491 and the culture-fluid vessel 472. Accordingly, culture gas is supplied to the culture fluid via the culture-gas supply tube 497, which allows a sufficient level of culture gas to be dissolved in the culture fluid. In this way, by producing culture fluid in which culture gas having a 5% concentration of carbon dioxide is dissolved inside the culture-fluid vessel 472, culture fluid including culture gas and nutrients necessary for nourishing the cells CE is supplied to the chamber 510. Also, by dissolving the culture gas in the culture fluid, the pH and so forth of the culture fluid can be regulated.

The carbon-dioxide concentration input to the computer PC from the $CO_2$-concentration detector 494 is collected in the memory in the form of text data, and data processing can be carried out in the computer PC.

Next, an examination method used in the biological-specimen examination system 410 having the above-described configuration will be described.

First, the scanning method and selection of a detection region in this embodiment will be described with reference to FIGS. 35A to 35D.

FIGS. 35A to 35D depict examples of the scanning method and selection of the detection areas in this embodiment.

Figure 35A:
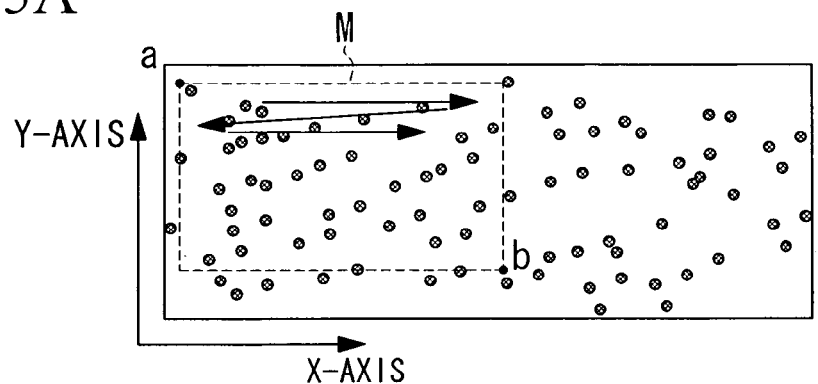
FIGS. 35A to 35D show examples of selecting the scanning method and the detection regions in the biological-specimen examination system.

In the example shown in FIG. 35A, a measurement region M (the region surrounded by the dashed line in the figure) is set by specifying an upper-left point a and a lower-right point b defining the measurement region M in the displayed image. More concretely, the measurement region M may be set by dragging a device like a mouse from point a to point b, or it may be specified by inputting the coordinates of the points a and b.

As indicated by the arrows in the figure, regarding the part to be measured by the detector 449, the specified measurement region M is scanned from left to right. That is, when scanning from the left to the right in the figure, scanning is performed parallel to the X direction, and when scanning from the right to the left, scanning is performed downward and to the left at an angle. While scanning from left to right, image acquisition of the cells CE is carried out.

Figure 35B:
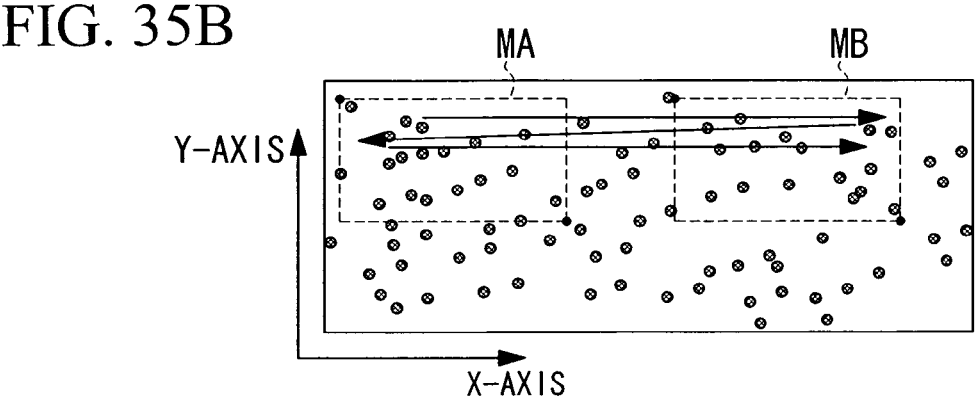

FIG. 35B is an example in which two measurement regions M are specified by the method described above. First, the two measurement regions MA and MB are specified using the method described above. The measurement region MA and the measurement region MB are arranged with a certain gap therebetween in the X direction in the figure, and they are disposed so as to completely overlap in the Y direction.

As indicated by the arrows, the part to be measured by the detector 449 in this example is scanned so as to measure the measurement regions MA and MB in parallel. That is, when scanning from the left to the right in the figure, scanning is performed from the measurement region MA to the measurement region MB, and when scanning from the right to the left, scanning is performed from the measurement region MB to the measurement region MA.

Figure 35C:
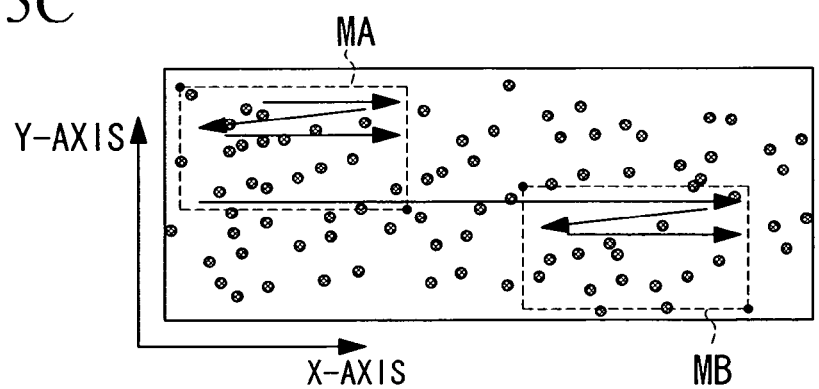

FIG. 35C is an example in which two measurement regions are set using the method described above. The two measurement regions MA and MB are disposed at different positions. Here, the measurement region MA and the measurement region MB are arranged with a gap therebetween in the X direction in the figure, and they are disposed so that they partially overlap in the Y direction in the figure.

As indicated by the arrows in the figure, regarding the parts to be measured by the detector 449 in this example, only the portions of the measurement regions MA and MB that overlap in the Y direction are sequentially scanned. That is, first the non-overlapping portion of the measurement region MA is scanned. Next, the overlapping portions of the measurement regions MA and MB are sequentially scanned. Then, the non-overlapping portion of the measurement region MB is scanned.

Figure 35D:
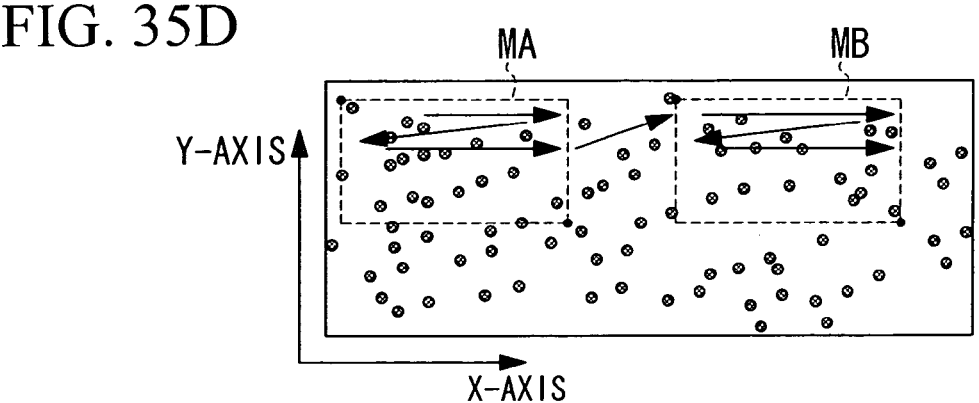

FIG. 35D is an example in which two measurement regions M are set by the method described above. In this example, the two measurement regions MA and MB are the same as those in FIG. 35B, but the scanning method is different.

As indicated by the arrows in the figure, regarding the parts to be measured by the detector 449 in this example, the measurement regions MA and MB are scanned independently. That is, after first scanning the entire measurement region MA, the entire measurement region MB is scanned.

Among the scanning methods shown in FIGS. 35A to 35D described above, the method with the shortest total distance moved or shortest scanning time is automatically selected by the computer PC on the basis of specified parameters and a measurement mode, which are described later.

When acquiring images of the region where the cells are cultured, it is possible to carry out image acquisition only in the required parts, as necessary, if that region is formed of a plurality of divided regions (detection regions) by, for example, specifying measurement regions M that can be imaged.

For example, if the settings of the computer PC are changed to alternately scan the entire region and predetermined parts of the object to be scanned, it is possible to observe phenomena unique to biological specimens which occur only for a short time. As one example, in a case where scanning of the entire region of an object is normally performed every 30 minutes, so long as scanning is performed in a predetermined measurement region M where cells of interest exist, it is possible to determine the occurrence of a specific phenomenon that is exhibited only every 15 minutes in those cells of interest.

In order to scan the desired measurement region M in the required time, the scanning time can be reduced, and the time required to irradiate other cells with light can be reduced.

Next, the procedure for measuring the cells CE will be described using a flowchart.

First, before measuring the cells CE, measurement parameters are set. Therefore, the procedure for setting the measurement parameters will be described with reference to FIG. 36.

Figure 36:
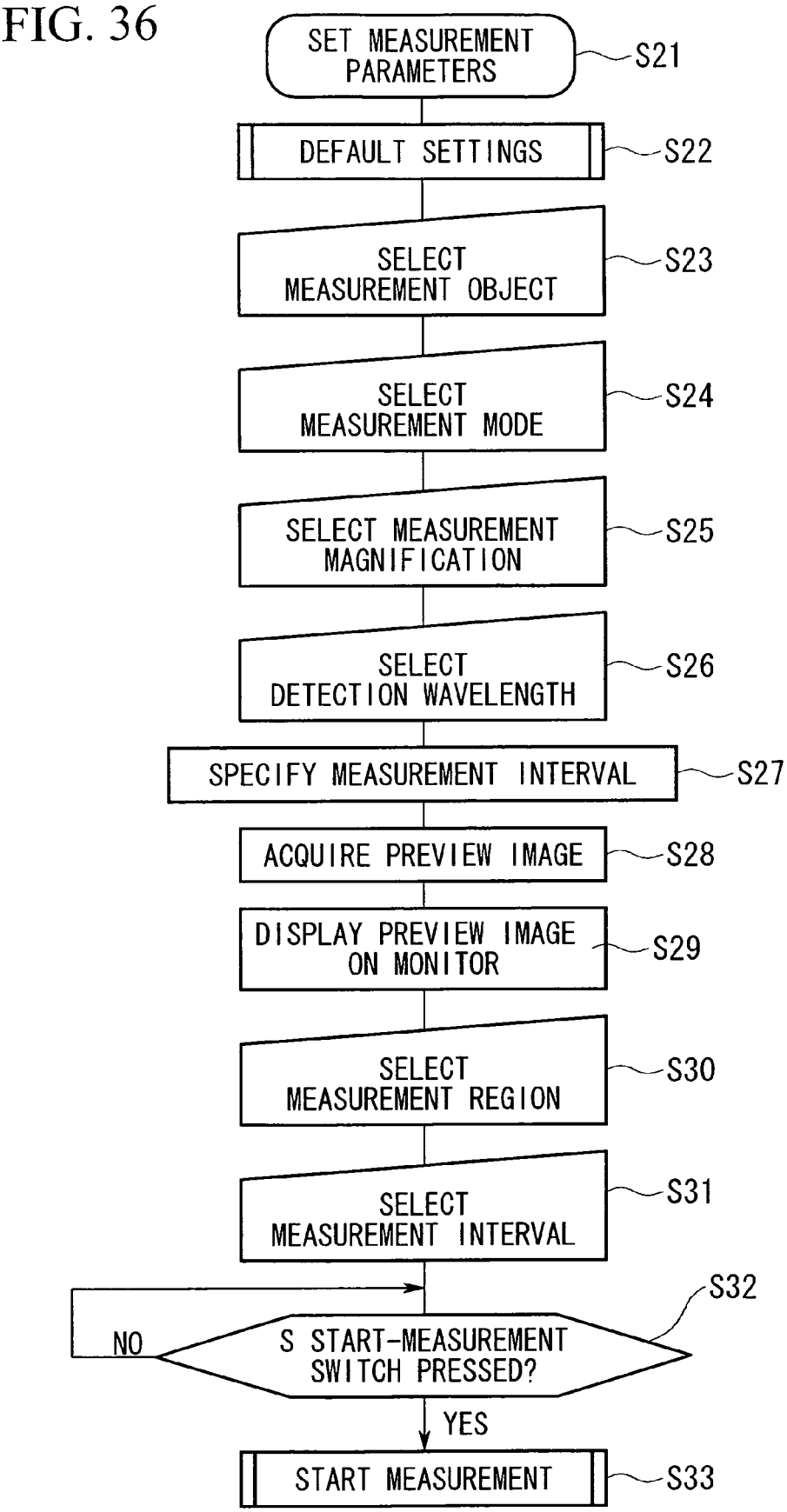
FIG. 36 is a flowchart showing a procedure for setting measurement parameters used in the biological-specimen examination system.

FIG. 36 is a flowchart showing the procedure for setting the measurement parameters.

First, the measurement parameters are set (step S21).

Then, default conditions are set (step S22). Here, the conditions set are the culturing conditions and the measurement conditions, for example, a $CO_2$ concentration of 5%, a temperature of 37° C., and so forth. These conditions can be changed to predetermined conditions by the user.

Next, the measurement object is selected (step S23). Measurement object means the container of the cells CE, for example, the microplate 520 or the slide glass 516.

Next, the measurement mode is selected (step S24). Possible measurement modes include an area acquisition mode, a line acquisition mode, an automatic mode, and so on. In the automatic mode, the measurement mode having the shortest measurement time is automatically selected from among the other modes.

Next, the measurement magnification is selected (step S25), and after that, the detection wavelength is selected (step S26). The measurement magnification and the detection wavelength can each be automatically selected from among two or more options.

Here, as the method of selecting the detection wavelength, a list of fluorescent proteins used, for example, GFP, HC-Red, and so on, is stored in advance in the computer PC, and one of them is selected from the stored list. The computer PC automatically selects the most appropriate excitation filter 456, absorption filter 458, and so on for examination, on the basis of the selected fluorescent protein. In this way, specific fluorescence from the cells CE can be detected.

The excitation filter 456, the absorption filter 458, the objective lens 448 and so on used for measurement are automatically changed in synchronization with the driving of the X-axis motion stage 422X and the Y-axis motion stage 422Y.

Next, the measurement interval is set (step S27).

Then, a preview image is acquired (step S28), and the preview image is displayed on the monitor (step S29). In the latter step, the preview image is displayed on the monitor when the user issues an instruction using a preview button or the like for instructing display of the preview image on the monitor. Thus, the user can confirm the preview image displayed on the monitor.

Next, the measurement region is selected (step S30). After selecting the measurement region, the preview image may be displayed on the monitor again to confirm whether the measurement region has been correctly selected.

Next, a predetermined measurement interval is selected from a plurality of specified measurement intervals (step S31).

Then, upon pressing a start-measurement switch (not shown; step S32), measurement of the cells CE commences (step S33). If the start-measurement switch is not pressed, the process stands by until the start-measurement switch is pressed (step S32).

If the start-measurement switch is not pressed in step S32, the process may jump back to any predetermined step to allow the measurement parameters to be set again.

After the measurement parameters have been set, measurement of the cells CE is carried out. Therefore, the procedure for measuring the cells CE will be described with reference to FIGS. 37 and 38.

Figure 37:
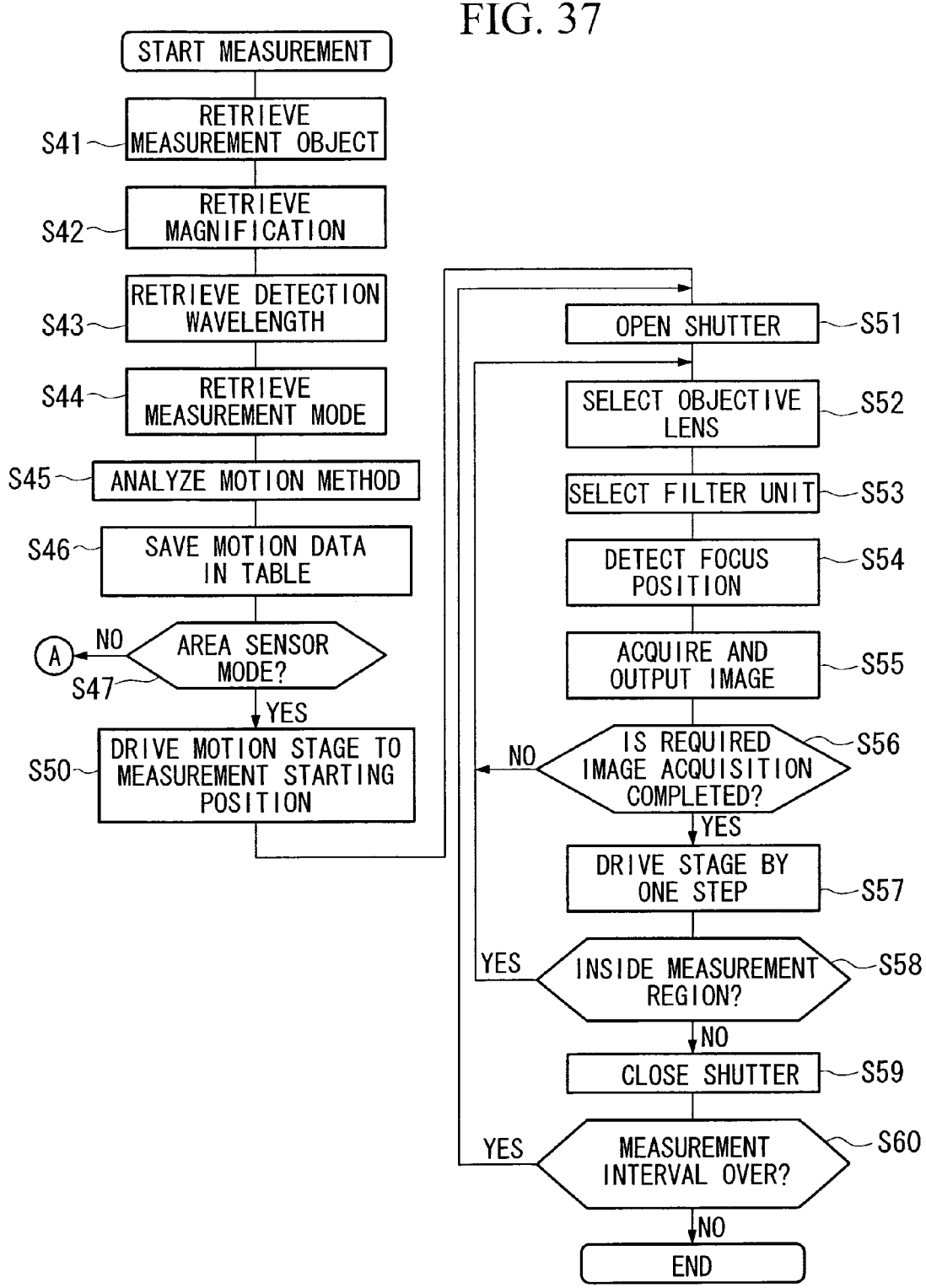
FIGS. 37 and 38 are flowcharts showing a measurement procedure in the biological-specimen examination system.
Figure 38:
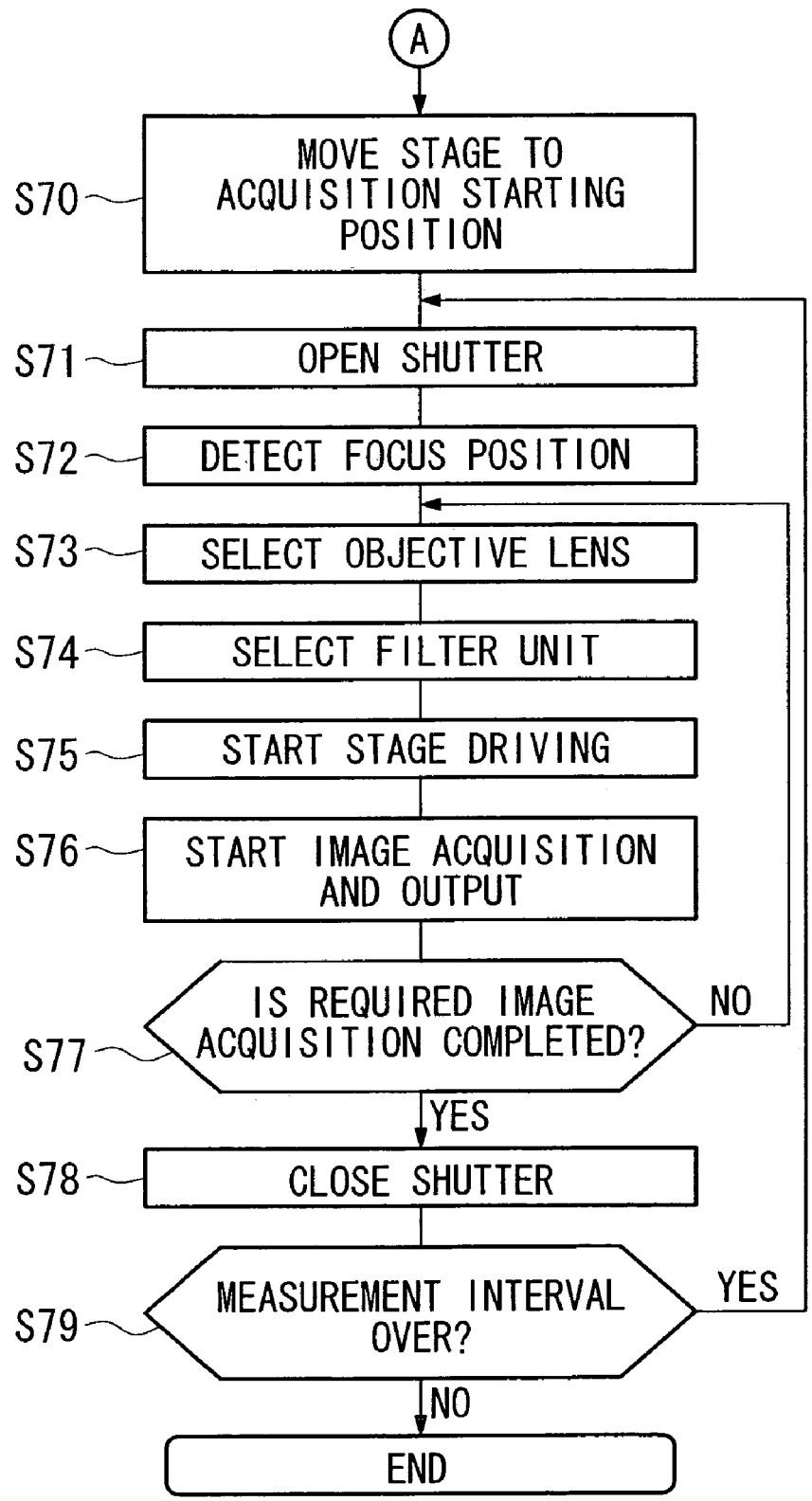

FIGS. 37 and 38 are flowcharts showing the measurement procedure.

First, when measurement starts, the measurement region is retrieved (step S41). Then, the magnification is retrieved (step S42), and the detection wavelength is retrieved (step S43).

Next, the measurement mode is retrieved (step S44). Here, the appropriate stage scanning method is determined on the basis of the retrieved measurement region, magnification, detection wavelength (fluorescence wavelength), and so on. If the measurement mode is set to the automatic mode, the image acquisition mode is also determined at this point.

Next, the method of operating the X-axis motion stage 422X and the Y-axis motion stage 422Y in accordance with the determined stage scanning mode is analyzed (step S45), and data for the analyzed operating method (operating data) is saved in a table in the computer PC (step S46).

Thereafter, measurement is carried out using a different measurement method depending on whether or not the area sensor mode is selected (step S47).

First, a description will be given in the case where the area sensor mode is selected.

When the start-measurement switch is pressed, the X-axis motion stage 422X and the Y-axis motion stage 422Y are moved to a measurement starting position (S50). In this step, the computer PC retrieves the measurement starting position which has been input and moves the X-axis motion stage 422X and the Y-axis motion stage 422Y to the measurement starting position, and the cells CE are thus moved to a position within the imaging field of the objective lens 448.

Then, the shutter 435 is opened (step S51) and the objective lens 448 is selected (step S52). Here, the computer PC drives the revolver 447 to select an objective lens 448 having a predetermined magnification on the basis of the specified measurement magnification.

Next, the filter unit 445 is selected (step S53). Here, the filter control unit 446C selects the excitation filter 456, the absorption filter 458, and so on that are most appropriate for the measurement on the basis of the fluorescent protein specified in the computer PC.

The operations carried out from when the start-measurement switch described above is pressed up to this point (steps S50 to S53) are automatically selected and executed according to the measurement mode.

After that, the focus position is detected (step S54), and then image acquisition is performed and the image data is output to an image memory in the computer PC (step S55).

Then, if the required image acquisition has not yet been completed, the operations from selection of the objective lens 448 (step S52) to image acquisition and output of the image data to the image memory in the computer PC (step S55) are repeated until the required image acquisition is completed (step S56).

When the required image acquisition has been completed, the X-axis motion stage 422X or the Y-axis motion stage 422Y is driven by one step (step S57). Then, if the position to which the X-axis motion stage 422X or the Y-axis motion stage 422Y has been moved is within the measurement region, the operations from selection of the objective lens 448 (step S52) to driving the motion stage by one step (step S57) are repeated. These operations are repeated until the position to which the X-axis motion stage 422X or the Y-axis motion stage 422Y has been moved is outside the measurement region (step S58).

When the position of the X-axis motion stage 422X or the Y-axis motion stage 422Y is outside the measurement region, the shutter 435 is closed (step S59).

Thereafter, once the predetermined measurement time interval is over, the operations from opening of the shutter 435 (step S51) to closing of the shutter 435 (step S59) are repeated until the end of the measurement time (step S60).

Next, a case where the area sensor mode is not selected shall be described.

When the start-measurement switch is pressed, the x-axis motion stage 422X and the Y-axis motion stage 422Y are moved to the measurement starting position (step S70). Here, the computer retrieves the measurement start position that was input and moves the X-axis motion stage 422X and the Y-axis motion stage 422Y to the measurement starting position to move the cells CE to a position within the imaging field of the objective lens 448.

Then, the shutter 435 is opened (step S71), and the focus position is detected (step S72).

Next, the objective lens 448 is selected (step S73). Here, the computer PC drives the revolver 447 to select an objective lens 448 having a predetermined magnification, on the basis of the specified measurement magnification.

Next, the filter unit 445 is selected (step S74). Here, the filter control unit 446C selects the excitation filter 456, the absorption filter 458, and so on that are most appropriate for the measurement on the basis of the fluorescent protein specified in the computer PC. The operations carried out from when the start-measurement switch is pressed up to this point (steps S70 to S74) are automatically selected and executed according to the measurement mode.

After that, driving of the X-axis motion stage 422X and the Y-axis stage 422Y commences (step S75), and then image acquisition is performed and the image data is output to an image memory in the computer PC (step S76).

Then, if the required image acquisition has not yet been completed, the operations from selection of the objective lens 448 (step S73) to image acquisition and output of the image data to the memory in the computer PC (step S76) are repeated until the required image acquisition is completed (step S77).

When the required image acquisition has been completed, the shutter 435 is closed (step S78).

Thereafter, once the predetermined measurement time interval is over, the operations from opening of the shutter 435 (step S71) to closing of the shutter 435 (step S78) are repeated until the end of the measurement time (step S79).

When image acquisition of the cells CE has been completed, the acquired images are then processed. Therefore, the method of processing the acquired images will be explained with reference to FIG. 39.

Figure 39:
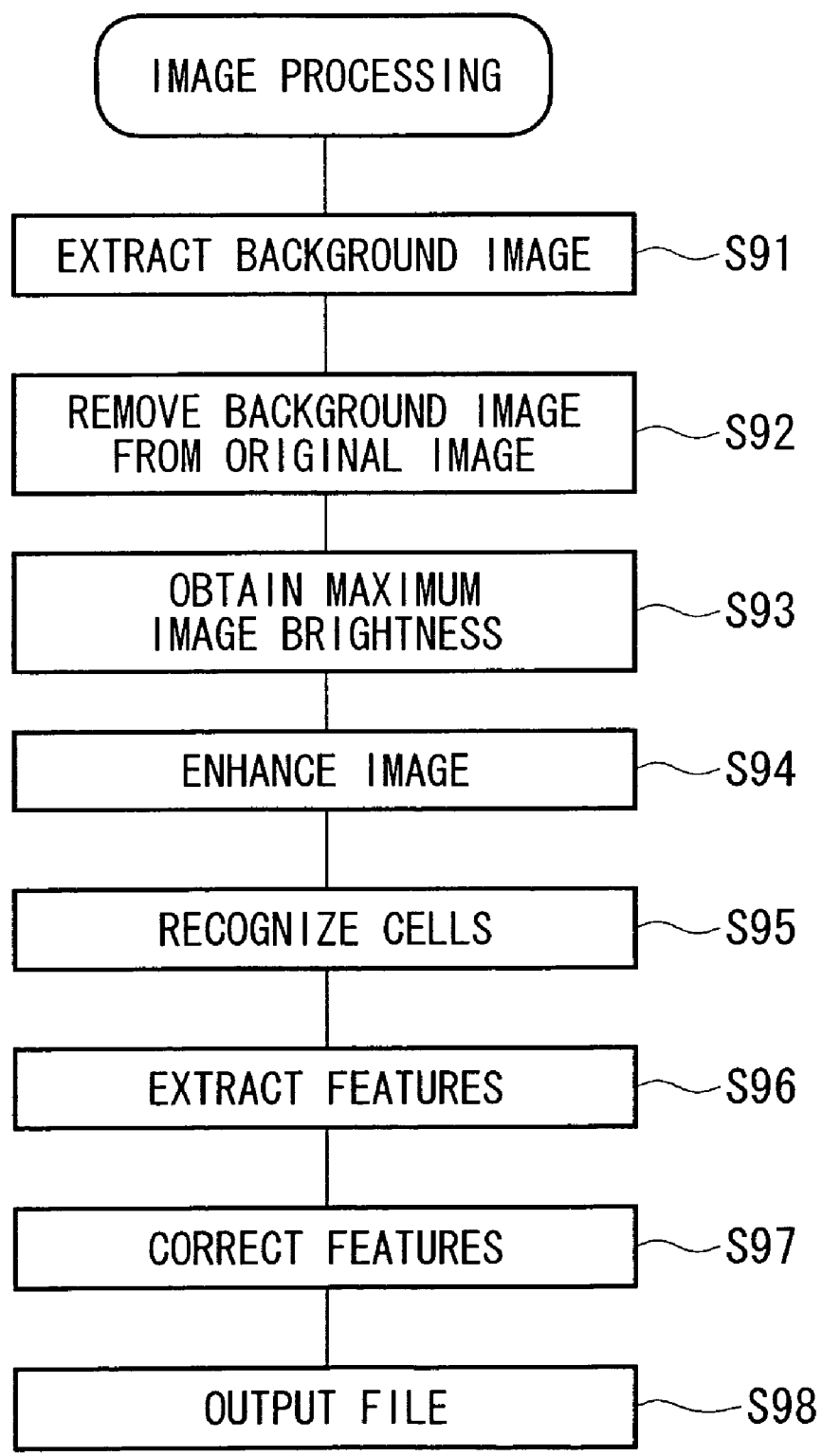
FIG. 39 is a flowchart showing an image processing method in the biological-specimen examination system.

FIG. 39 is a flowchart showing the image processing method.

First, the image processing unit of the computer PC extracts the background image from the acquired images collected in the memory (step S91), and removes the background image from the acquired images (step S92).

Next, the maximum brightness region of the image, which can be enhanced, is read out (step S93) and multiplied by, for example, a predetermined coefficient to enhance the image (step S94). With this processing, the image is enhanced so that the individual cells CE can easily be recognized as spots in the image from which the background is removed.

Then, by extracting portions having a brightness higher than, for example, a predetermined threshold from the enhanced image, the bright cells CE can be clearly recognized as individual spots (step S95).

Next, geometrical features, such as the center of gravity and the area, chemical features, and optical features, such as the fluorescence intensity, of the cells CE are more accurately determined, and positional information of the cells CE is determined and extracted (step S96). Extracting these features allows the individual cells CE to be distinguished.

After extracting the features of the cells CE, correction (step S97) of the enhancement (S94) carried out for recognizing the cells CE is carried out. With this correction, the effect of the predetermined coefficient used for enhancing the image is removed.

Next, after correction, the features are output to a file, for example, and are stored in that file (step S98).

Accordingly, the image processing unit of the computer PC can convert the fluorescence distribution of the cells CE at each position on the entire surface of the slide glass, microplate, or the like into an image. Also, since the image processing unit can accurately track the individual cells CE, it can target a predetermined number of cells CE, which allows localized, long-term measurement of the fluorescence distribution of the cells CE while performing culturing. Furthermore, while culturing the cells CE, the entire surface of the slide glass, microplate, or the like is measured at fixed time intervals, for example, and the fluorescence intensity of the cells CE over time can be automatically measured.

Next, data processing carried out after extracting data about the features of the cells CE from the acquired images will be described with reference to FIG. 40.

Figure 40:
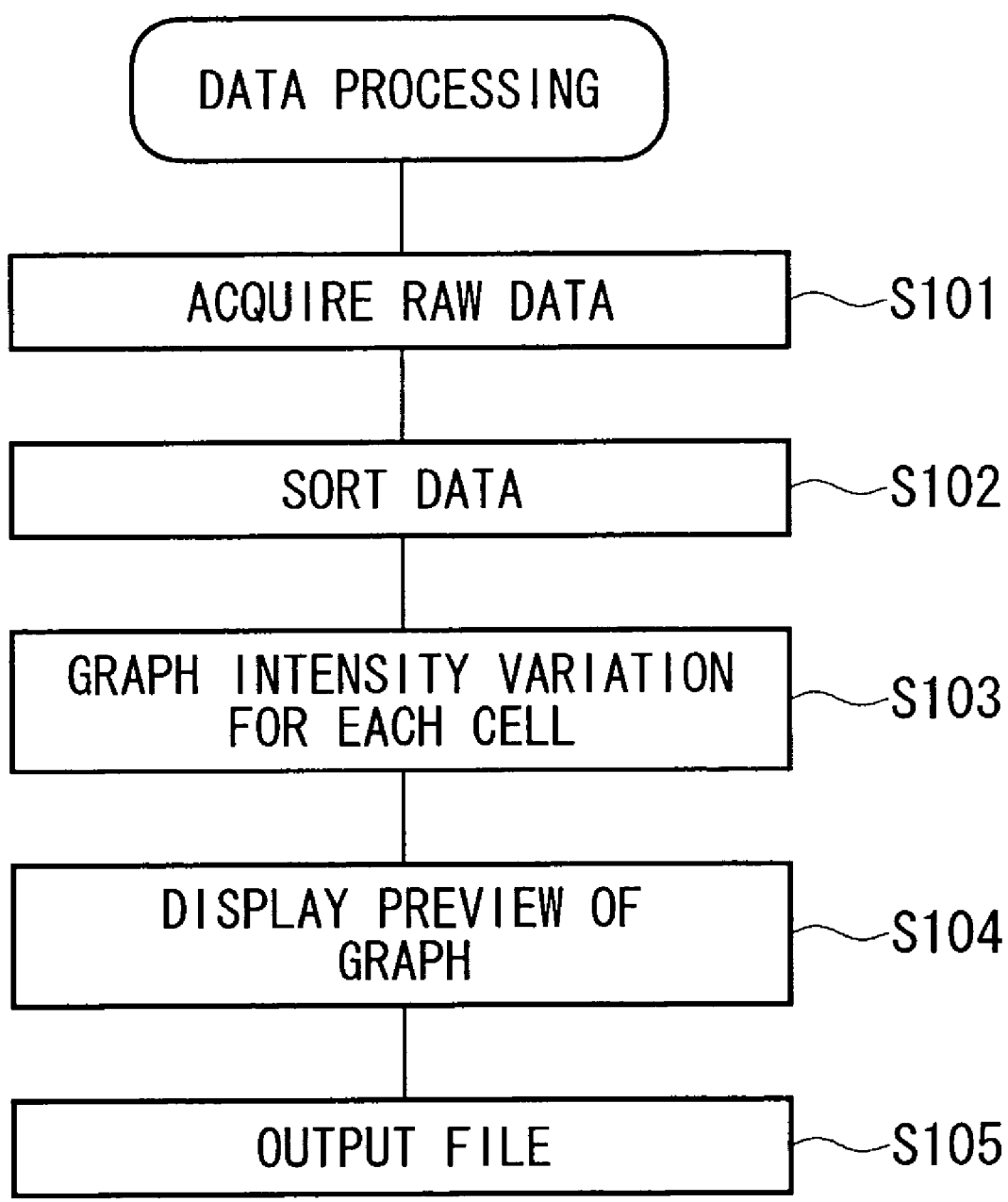
FIG. 40 is a flowchart showing a data processing procedure in the biological-specimen examination system.

FIG. 40 is a flowchart depicting the data processing procedure.

Here, processing of the cell data (features) stored in the file is carried performed by a data processing unit of the computer PC.

First, the data processing unit reads out (step S101) raw data (features) of the cells CE, which is stored in the file, and sorts the data to arrange it time-sequentially for each cell CE (step S102). When the data has been sorted, the data processing unit graphs the variation in brightness of each cell CE, that is, the level of expression, with time (step S103).

When the graphing has been completed, the data processing unit displays a preview of the graph (step S104), and outputs the graph data to a file (step S105).

By performing this processing, when cells CE are cultured for an extended period of time, the variation of a single cell with time can be easily examined. Therefore, during culturing, the variation in the level of expression of the cells CE with time can be accurately and easily measured.

Next, adjustment of the irradiation intensity carried out during measurement of the cells CE will be explained with reference to FIG. 41.

Figure 41:
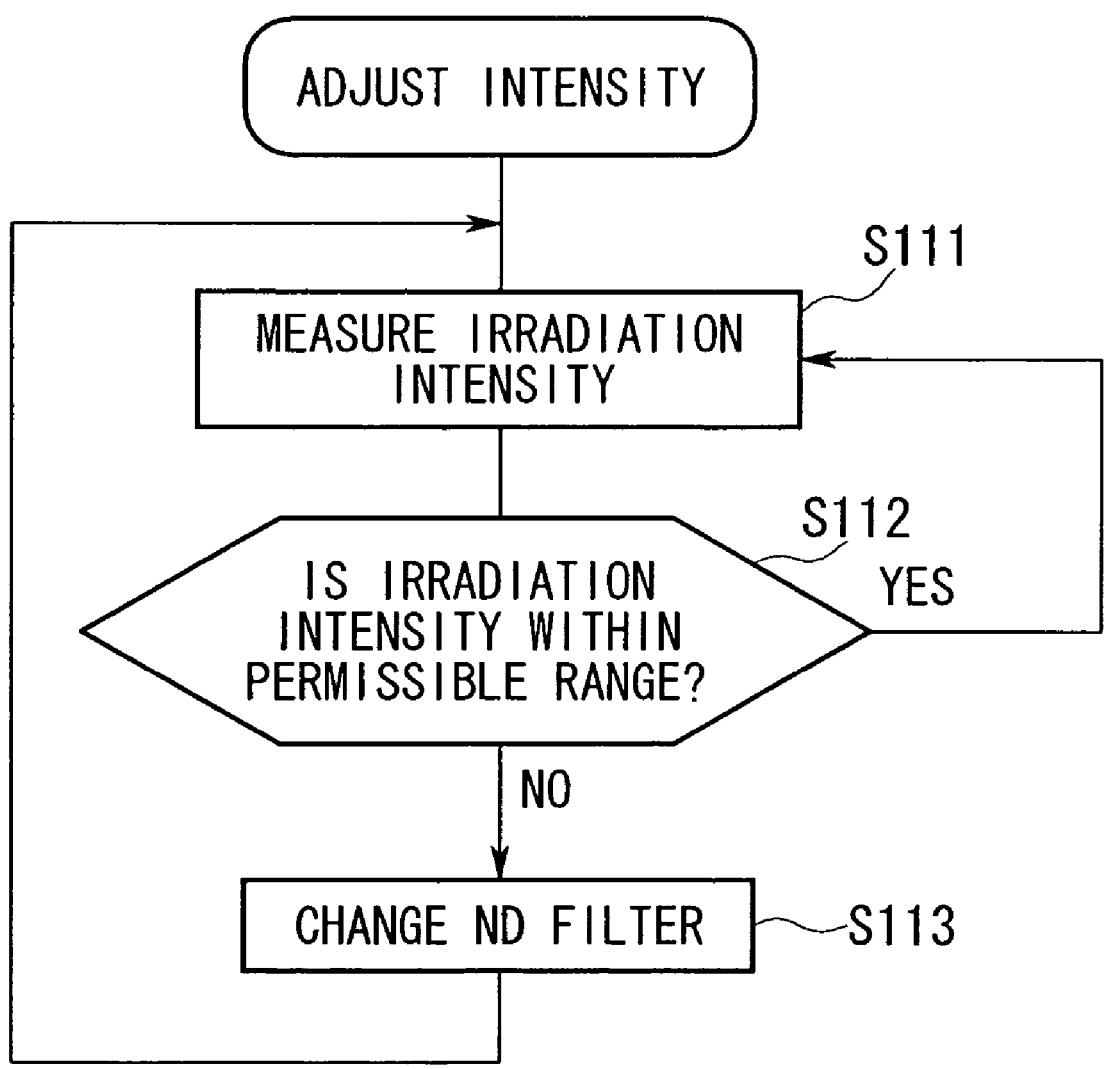
FIG. 41 is a flowchart showing a procedure for adjusting intensity in the biological-specimen examination system.

FIG. 41 is a flowchart showing the procedure for adjusting the intensity.

First, the intensity of light irradiated onto the cells CE is measured (step S111). The irradiation intensity may be calculated from the output of the light-intensity monitor 450, by providing an irradiance meter for measuring the intensity, or by providing a power meter and calculating the intensity from the output of the power meter.

If the measured irradiation intensity is within a permissible range, the process returns to measurement of the irradiation intensity (step S111) and repeats this until the irradiation intensity is outside the permissible range (step S112).

Once the irradiation intensity is outside the permissible range, the ND filter (not shown) included in the light-intensity adjusting mechanism 443 is changed (step S113) to adjust the irradiation intensity so that it falls within the permissible range. Thereafter, the process returns to measurement of the irradiation intensity (step S111), and repeats the adjustment of the irradiation intensity.

Next, a control method for supplying and replacing the culture fluid in the chamber 510 is described with reference to FIG. 42.

Figure 42:
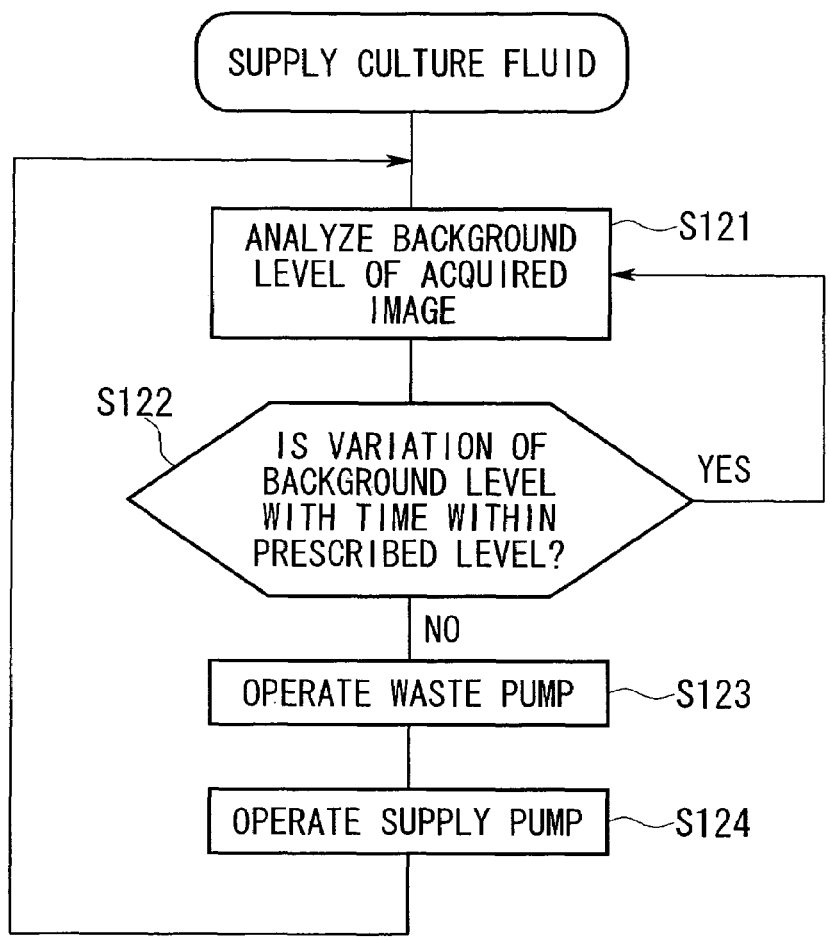
FIG. 42 is a flowchart showing the method of supplying and replacing culture fluid in the biological-specimen examination system.
Figure 43:
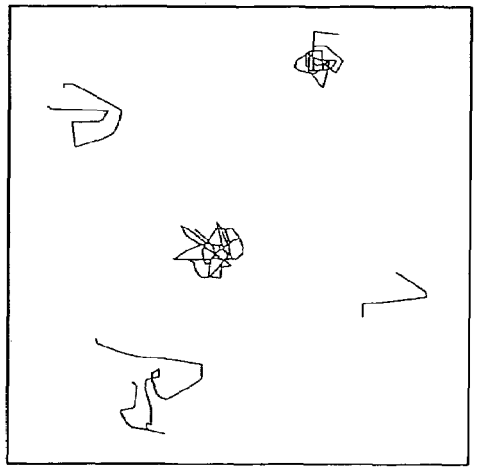
FIG. 43 shows a cell-tracking image representing the motion of cells over time.

FIG. 42 is a flowchart showing the method for supplying and replacing the culture fluid.

First, the background level of the acquired image is analyzed (step S121). The autofluorescence of the culture fluid in the background of the acquired image is acquired, and the brightness of this autofluorescence is analyzed.

Here, since the brightness of this autofluorescence increases as the culture fluid ages, the point at which the culture fluid should be replaced can be detected by measuring the brightness of this autofluorescence.

Then, if the temporal variation in the analyzed background level is within a predetermined level, the process returns to analysis of the background level (step S121) and repeats this until the temporal variation of the background level exceeds the predetermined level (step S122).

Once the temporal variation of the background level exceeds the predetermined value, the waste pump 482 for the culture fluid is operated (step S123), and then, the supply pump 481 for the culture fluid is operated (step S124).

The intervals at which the culture fluid should be supplied and replaced may be determined on the basis of the autofluorescence of the culture fluid, as described above. Alternatively, the culture fluid may be supplied/replaced continuously, or automatically at intervals specified in advance by the user. Alternatively, the point at which the culture fluid should be replaced can be specified at will by selecting the type of cells CE from a table that is registered in advance. In addition, the amount of culture fluid to be replaced may be specified by the user or may be determined on the basis of the autofluorescence of the culture fluid. Alternatively, the amount of culture fluid to be replaced can be specified at will by selecting the type of cells CE from a table that is registered in advance.

The amount of culture fluid to be replaced may be calculated and determined automatically using the weight and so on.

In this embodiment, the level of autofluorescence in the background is detected using the acquired image; however, it may be detected from an acquired image of a location where cells CE do not exist. Alternatively, it may be detected by providing an optical detector in the vicinity of the culture-fluid vessel 472.

According to the measurement procedure described above, as shown in FIG. 43, a cell-tracking image showing the change in position of individual cells over time can be obtained.

Next, the culturing and measurement procedures when using the microplate 520 will be described with reference to FIGS. 44 and 45.

Figure 44:
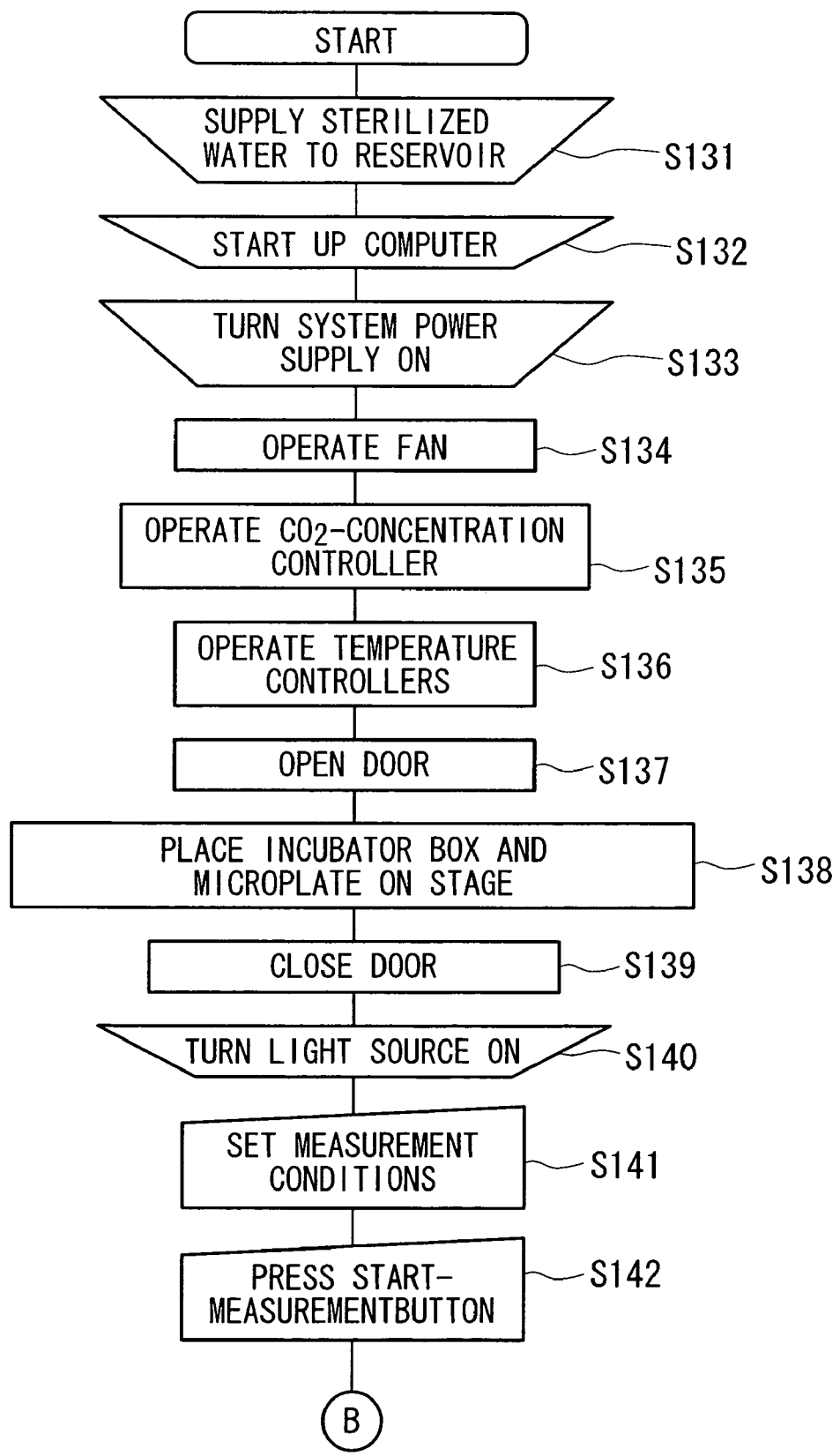
FIGS. 44 and 45 are flowcharts showing culturing and measurement using a microplate.
Figure 45:
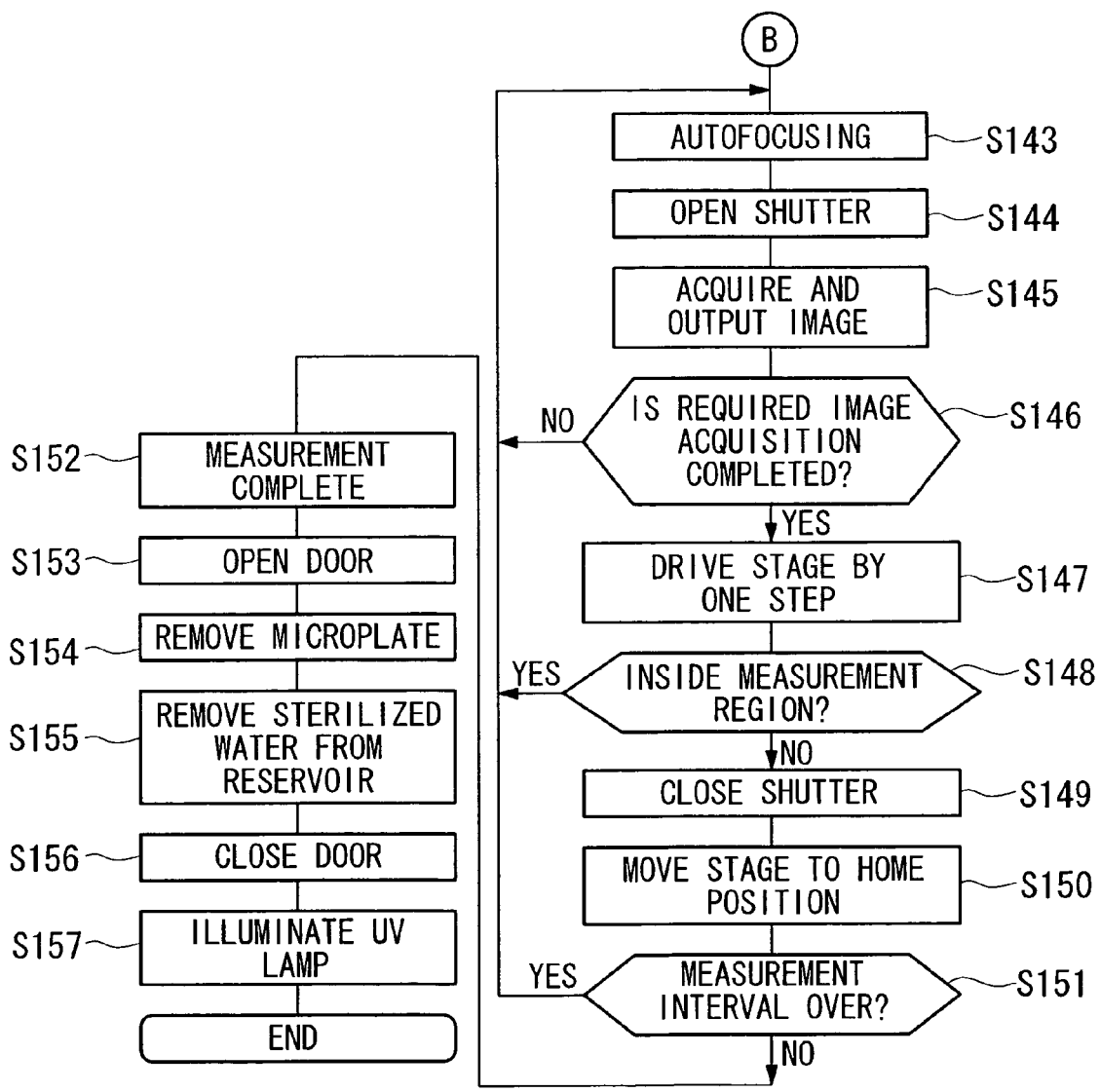

FIGS. 44 and 45 are flowcharts showing the culturing and measurement when using the microplate 520.

First, sterilized water is supplied to the reservoir 521 in the incubator box 500*a* (step S131).

Next, the PC is started up (step S132), and the main power supplies for the detection unit 420 and the culture unit 470 are turned on (step S133).

After that, the internal fan 522 inside the incubator box 500*a* is operated (step S134) to circulate the air inside the incubator box 500*a*. Then, the $CO_2$-concentration controller 495 is operated (step S135) to regulate the carbon dioxide concentration in the culture gas supplied to the incubator box 500*a* at 5%. Thereafter, the temperature controllers are operated (step S136) to regulate the culture-fluid temperature, the culture-gas temperature, and the temperature inside the insulated compartment 421 at about 37° C.

After that, the door 427 of the detection unit 420 is opened (step S137), the incubator box 500*a* is placed on the stage 422 (step S138), and the door 427 is closed (step S139).

Next, the transmission light source 423 is turned on (step S140) to irradiate the cells CE with transmission light, and the measurement conditions are set (step S141).

Then, by pressing the start-measurement button (step S142), measurement of the cells CE commences.

First, scanning is carried out beforehand on predetermined cells CE to perform autofocusing (step S143), and once the focus position of each part has been determined, the shutter 435 is opened (step S144).

Next, an image of the cells CE is acquired and output (step S145). Here, the acquired image data is output to the memory of the computer PC.

Then, if the required image acquisition has not yet been completed, the operations from the autofocusing (step S143) to the image acquisition and outputting (step S145) are repeated until the required image acquisition has been completed (step S146). Here, the required images are, for example, the images acquired using the selected wavelength, the images acquired using the selected magnification, and so forth.

Once the required image acquisition has been completed, the X-axis motion stage 422X or the Y-axis motion stage 422Y is driven by one step (step S147). Then, if the position to which the X-axis motion stage 422X or the Y-axis motion stage 422Y has moved is within the measurement region, the operations from the autofocusing (step S143) to driving of the motion stage by a single step (step S147) are repeated. These operations are repeated until the position to which the X-axis motion stage 422X or the Y-axis motion stage 422Y has moved is outside of the measurement region.

When the position to which the X-axis motion stage 422X or the Y-axis motion stage 422Y has moved is outside the measurement region, the shutter 435 is closed (step S149), and the X-axis motion stage 422X and the Y-axis motion stage 422Y are moved to their home positions (step S150).

Thereafter, after a predetermined measurement interval, the operations from the autofocusing (step S143) to moving the stages to their home positions (step S150) are repeated until the end of the measurement time (step S151).

Once the measurement time ends (step S152), the door 427 is opened (step S153), and the microplate 520 is removed from the incubator box 500*a* (step S154). Then, the sterilized water is removed from the reservoir 521 (step S155), and the door 427 is closed (S156).

After that, the UV lamp 425 inside the insulated compartment 421 is illuminated (step S157) to sterilize the interior of the insulated compartment 421, and the measurement is thus completed.

As described above, the sterilization may be carried out at the end of the measurement procedure, or alternatively, it may be carried out at the beginning of the measurement procedure to sterilize the insulated compartment 421 before measurement actually takes place.

The autofocusing may be carried out for each measurement of the cells CE, as described above, but it need not be carried out for each measurement.

With the configuration described above, since the thermal environment is maintained by the insulated compartment 421 and the humidity environment and the culture-fluid environment are maintained by the chamber 510 disposed inside the insulated compartment 421, the humidity environment and the culture-fluid environment are influenced by the thermal environment, and therefore the thermal environment inside the chamber 510 is also maintained.

Accordingly, sudden changes and non-uniformities in the thermal environment, which might cause damage to the cells CE, are moderated via the humidity environment and the culture-fluid environment, and therefore, it is possible to reduce damage caused to the cells CE.

Also, since the dimensions of the chamber 510 are small compared to the insulated compartment 421, it is easier to maintain and control the humidity environment and the culture-fluid environment, thus making it relatively difficult to cause damage to the cells CE.

Since the cells CE can be examined through the insulated compartment 421, the incubator box 500, and the chamber 510, it is possible to carry out examination while culturing the cells CE, without causing any damage to the cells CE. Accordingly, behavior that the cells exhibit during culturing can be accurately measured over time.

It is possible to measure in real time the reaction of the cells CE in the object under examination while changing the culture conditions. For example, the existence and level of expression of proteins can be measured, and changes in the level of expression with time can be accurately measured.

Furthermore, deterioration of the activity of the cells CE by handling them in a first examination can be prevented, which enables multiple examinations of the same cells CE. Also, since multiple examinations of the same cells CE can be carried out at intervals, it is not necessary to control the experimental protocol.

Since the detection section 440 examines the cells CE in the chamber 510 via the insulated compartment 421 and the incubator 500, it is not necessary to insert and remove the cells CE from the chamber 510 during examination, and therefore, the cells CE can remain inside the chamber 510 during examination. Accordingly, it is possible to accurately examine the same position in each examination. Also, contamination can be prevented during examination, which can prevent the cells from being stressed.

Furthermore, by controlling the environmental conditions inside the chamber 510 (for example, the combination of carbon dioxide concentration and humidity), it is possible to prevent the performance of the detection section 440 from deteriorating.

Moreover, since the cells CE are contained inside the chamber 510, which is disposed inside the insulated compartment 421 and the incubator box 500, a certain distance can be maintained between the cells CE and the environment outside the incubator box 500 compared to a case where chamber 510 is not provided. Therefore, it is possible to reduce the effects of electric and magnetic fields from outside the incubator box 500, such as those from the driving motors of the X-axis motion stage 422X and the Y-axis motions stage 422Y and magnets provided in the door 427.

Eleventh Embodiment

Next, an eleventh embodiment will be described with reference to FIGS. 46A to 48.

The basic construction of the biological-specimen examination system of this embodiment is the same as the tenth embodiment, but the constructions of the detection unit and the culture unit are different from those in the tenth embodiment. Therefore, in this embodiment, only the detection unit and the culture unit will be described using FIGS. 46A to 48, and a description of the chamber and so on will be omitted.

Figure 46A:
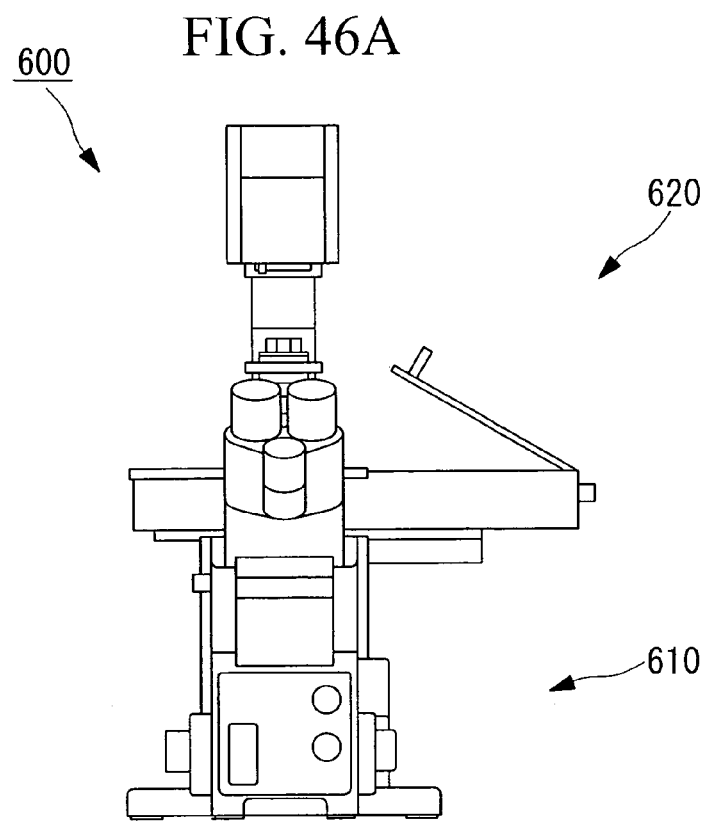
FIGS. 46A and 46B are, respectively, an elevational view and a side view of a biological-specimen examination system according to an eleventh embodiment, in which a microscope imaging apparatus is provided.
Figure 46B:
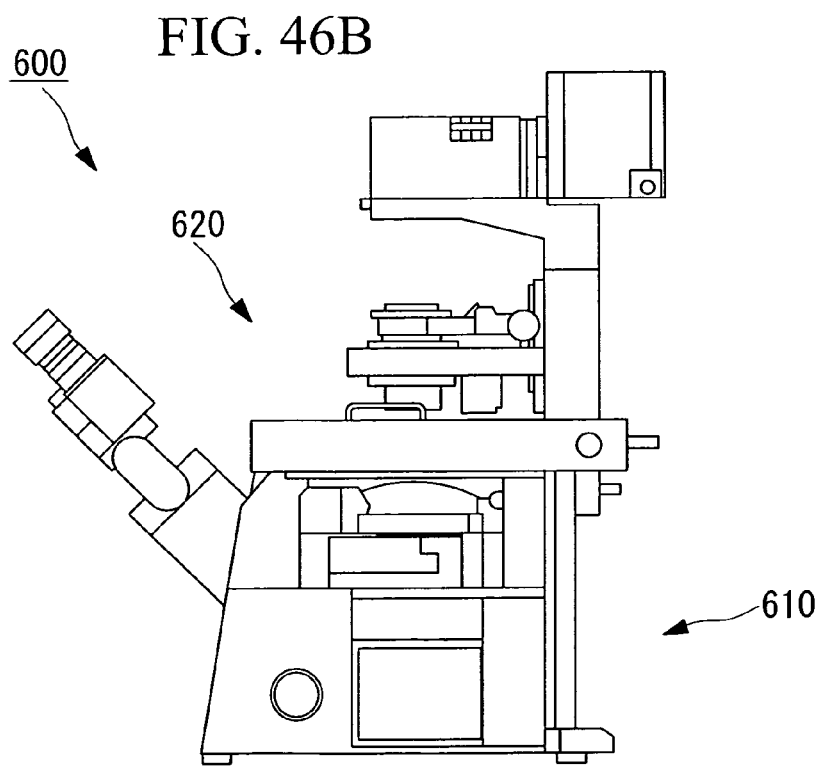

FIG. 46A is an elevational view of a biological-specimen examination system 600 of this embodiment, and FIG. 46B is a side view thereof.

As shown in FIGS. 46A and 46B, the biological-specimen examination system 600 includes an inverted microscope (microscope imaging apparatus) 610 and a culture stage 620. The inverted microscope 610 and the culture stage 620 may be integrated or they may be constructed so as to be detachable from each other.

If the culture system 620 can be attached to and detached from the inverted microscope 610, an existing inverted microscope can also be used. In such a case, even though a stage driving motor is disposed in the vicinity of the cells CE due to constraints on the shape and the construction involved with attaching the culture stage 620, for example, the effect of electric and magnetic fields on the cells CE can be suppressed.

Also, when examining the cells CE using the inverted microscope 610, for example, the culture stage 620 can be attached to the inverted microscope 610; at other times (for example, when culturing the cells CE), the inverted microscope 610 can be removed from the microscope.

Figure 47:
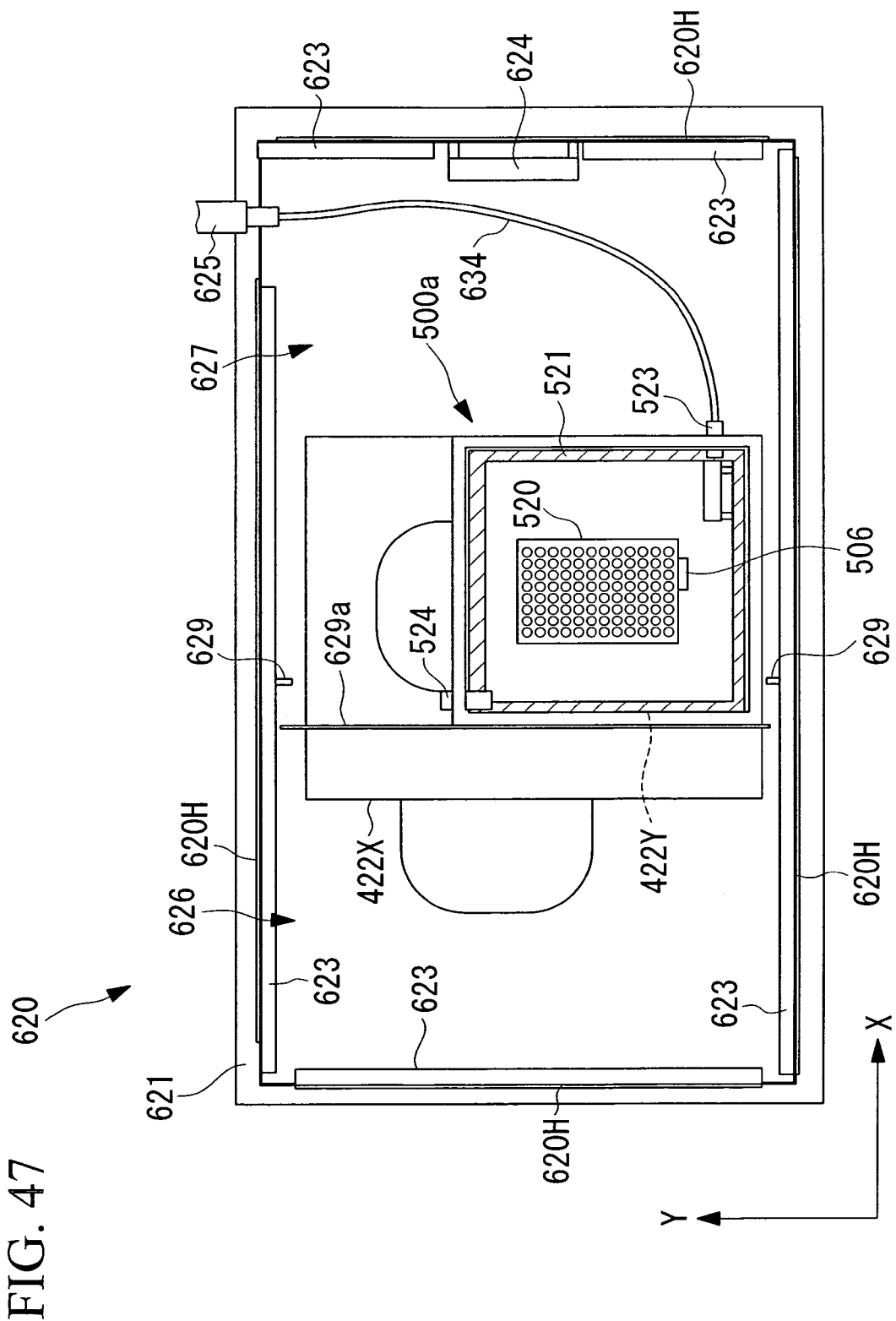
FIG. 47 is a plane view of a culture stage in the biological-specimen examination system shown in FIGS. 46A and 46B.
Figure 48:
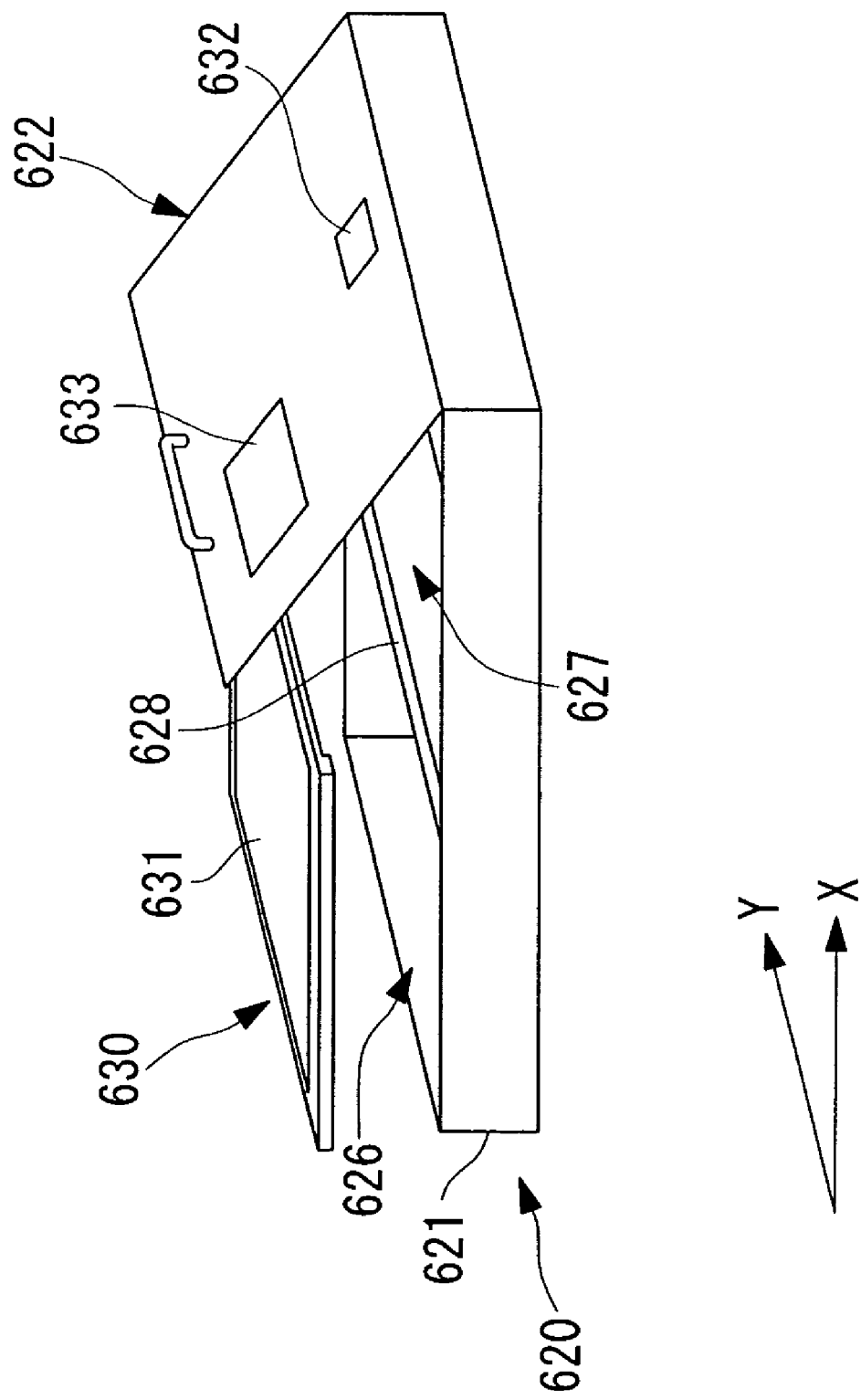
FIG. 48 is a perspective view of the culture stage in the biological-specimen examination system shown in FIGS. 46A and 46B.

FIG. 47 is a plane view of the culture stage 620, and FIG. 48 is a perspective view of the culture stage 620.

As shown in FIGS. 46A, 46B, and 47, the culture stage 620 includes a frame 621, openable/closable lid 622 provided on the upper surface of the frame 621, an X-axis motion stage 422X, a Y-axis motion stage 422Y, a small or strip-shaped heater 620H, a heatsink 623, a fan 624, and culture-gas supply connector 625.

The frame 621 is preferably formed of a highly opaque, corrosion-resistant material, such as anodized aluminum or stainless steel, like SUS 316. More preferably, from the viewpoint of thermal insulation, a material having a low thermal conductivity is selected.

The interior of the frame 621 is divided into a measurement area 626 for performing examination of cultured cells and a non-measurement area 627 only for culturing cells. Thus, cell culturing is performed in the culture stage 620. A microplate 520 that holds the cells is accommodated inside the culture stage 620, and the culture stage 620 is configured so as to allow examination of the cells in the microplate 520 from outside the culture stage 620. In the description given here, the microplate 520 is used as a culture vessel, as shown in FIGS. 47 and 48, but a dish or flask may also be used.

The fan 624 and the culture-gas supply connector 625 are disposed in a side wall in the non-measurement area 627 in the frame 621. Also, the heater 620H and the heatsink 623 for dissipating heat from the heater 620H are disposed in an area where the fan 624 and the culture-gas supply connector 625 are not disposed (including the measurement area 626).

The fan 624 causes convection of the air inside the culture stage 620 and is arranged so as not to blow directly onto the incubator box 500a.

The temperature inside the culture stage 620 is raised by means of the heater 620H and is regulated at 36.5° C.±0.5° C.

As shown in FIGS. 47 and 48, the X-axis motion stage 422X and the Y-axis motion stage 422Y are provided on the bottom surface of the frame 621. The X-axis motion stage 422X and the Y-axis motion stage 422Y are driven by, for example, motors and ball screws.

A small or strip-shaped heater (not shown) is attached to the Y-axis motion stage 422Y. The heater is disposed at a position such that the microplate 520 is uniformly heated.

The measurement area 626 and the non-measurement area 627 are formed by dividing the interior of the culture stage 620 in the X-direction by means of a top plate 628 and a pair of partition seats 629, which are fixed to the frame 621. The region to the left of the partition seats 629 in FIG. 47 constitutes the measurement area 626, and the region to the right constitutes the non-measurement area 627.

A partition plate 629a that is formed in substantially the same shape as the cross-sectional shape of the frame 621 is attached to the X-axis motion stage 422X.

By moving the X-axis motion stage 422X towards the non-measurement area 627, side faces at both ends (the ends in the Y-direction) of the partition plate 629a come into contact with the partition seats 629, and the partition plate 629a is thus positioned so as to divide the space inside the frame 621 into two portions in the left-to-right (X-axis) direction.

Furthermore, since the edge of the partition plate 629a at the top plate 628 is positioned in contact with the lower surface of the top plate 628, the measurement area 626 and the non-measurement area 627 can define two spaces that are separated from each other.

At the upper opening of the measurement area 626, a glass lid 630 is removably attached to the frame 621 and is disposed so as to cover the upper opening of the measurement area 626. The glass lid 630 can be attached by, for example, screwing the glass lid 630 to the frame 621, or by means of a lock mechanism, a hook, a magnet, and so forth.

The glass lid 630 may be constructed such that the entire surface or substantially the entire surface except for the peripheral frame portion is formed of the glass plate 631, or it may be formed with a minimum possible area so long as it does not obstruct measurement. In order to suppress the reflection of light during transmission examination and incidence examination, it is preferable to use an optical glass material having an anti-reflection film (AR coat) coated on both sides thereof as the glass plate 631.

The anti-reflection film may be coated on both sides of the glass plate 631, as described above, or it may be coated on only one side of the glass plate 631.

The glass lid 630 may be removed as required when carrying out various tasks, for example, when changing the objective lens of the inverted microscope 610, when cleaning the inside of the measurement area 626, and so forth.

The glass lid 630 may be provided with an observation hole into which the objective lens of the inverted microscope 610 is inserted. Also, a rubber sheet may be disposed in the observation hole to occupy a gap between the objective lens and the observation hole. The sheet is preferably disposed so as to prevent relative motion between the objective lens and the culture stage 620.

At the upper opening of the non-measurement area 627, the openable/closable lid 622 is attached so that it can be opened and closed by means of a hinge or the like. When closed, one edge of the openable/closable lid 622 is in contact with the top plate 628 so as to be supported.

The openable/closable lid 622 is entirely formed of an opaque material (for example, the same material as the frame 621) and is provided with an observation-hole cover 632 that blocks the observation hole or a UV-irradiation-hole cover 633 that blocks a UV irradiation hole, as required.

The observation hole is an opening (window) formed in the openable/closable lid 622. The observation-hole cover 632 is formed, for example, of a glass plate, a resin plate, or the like having low transmittance and is inserted in the observation hole. Also, the observation-hole cover 632 is formed of the same opaque material as the openable/closable lid 622 and may be attached in such a manner that it can be either detached or opened and closed.

The UV-irradiation-hole is an opening (window) formed in the openable/closable lid 622. The UV-irradiation-hole cover 633 is formed, for example, of the same opaque material as the openable/closable lid 622 and is attached in such a manner that it can be opened and closed, or detached from the UV irradiation hole.

The UV-irradiation-hole cover 633 is removed when irradiating the interior of the non-measurement area 627 with ultraviolet (UV) light to sterilize it. A handheld UV lamp can be used for the UV irradiation.

The incubator box 500a, which contains the microplate 520, is held on the Y-axis motion stage 422Y. Since the incubator box 500a is the same as that described in the tenth embodiment, the same components are assigned the same reference numerals, and a description thereof shall be omitted.

Culture gas is supplied to the connector 523 of the incubator box 500a via a culture-gas supply tube 634 from a culture-gas supply connector 625 of the culture stage 620.

With the configuration described above, since the biological-specimen examination system 600 according to the present invention includes the integrated inverted microscope 610, a biological specimen can be examined using the inverted microscope 610. Therefore, more detailed examination can be carried out compared to a case where the inverted microscope 610 is not provided.

When measuring and culturing the cells, in order that the cells are not affected by ambient light, the entire biological-specimen examination system 600 may be surrounded with a blackout curtain.

Also, instead of cells, the biological specimen to be measured may be various other types of biological specimen, such as bacteria, microorganisms, ova, and so forth.

With the biological-specimen examination system of this embodiment, since it is possible to reduce the image acquisition time, special phenomena that occur in the biological specimen only for a short time can be observed, and the accuracy of the examination results of the biological specimen can be improved.

Furthermore, with the biological-specimen examination system of this embodiment, an advantage is afforded in that, even when the brightness of the biological specimen changes over time, it is possible to effectively observe such changes in the biological specimen over time. Also, it is possible to accurately examine a wide range of biological specimens, from specimens having low brightness to specimens having high brightness.

Moreover, with the biological-specimen examination system of this embodiment, since the time required for measuring the measurement region once can be shortened, the motion of the biological specimen in part of the measurement region does not vary substantially over time. Thus, the accuracy of the examination results when examining the biological specimen over time can be improved.

What is claimed is:

1. A microscope imaging apparatus comprising:
a stage that holds an object under examination;
an illumination unit that illuminates the object under examination;
an image-acquisition unit that acquires images of the object under examination;
a motion unit that moves the stage and the image-acquisition unit relative to each other; and
a control unit that controls the image-acquisition unit and the motion unit,
wherein the image-acquisition unit includes an imaging device that is capable of image acquisition using two methods;
the control unit includes:
an examination-object-parameter input unit for inputting information about the object under examination as an examination-object parameter;
a calculation unit that calculates a time required for the relative motion on the basis of the examination-object parameter which has been input; and a switching unit that changes the image-acquisition method of the imaging device on the basis of the calculation result; and the two image-acquisition methods are a time delay integration method and a two-dimensional imaging method in which accumulated charge is produced by a single exposure.

2. A microscope imaging apparatus according to claim 1, wherein the examination-object parameter is the wavelength used in the image acquisition.

3. A microscope imaging apparatus according to claim 1, wherein the examination-object parameter is the exposure time used in the image acquisition.

4. A microscope imaging apparatus according to claim 1, wherein the examination-object parameter is the density of the object under examination.

* * * * *